US010017774B2

(12) United States Patent
Ye et al.

(10) Patent No.: US 10,017,774 B2
(45) Date of Patent: Jul. 10, 2018

(54) CONTROL OF PESTS IN PLANTS

(75) Inventors: Jian Ye, Singapore (SG); Nam-Hai Chua, Singapore (SG); Jing Qu, Singapore (SG); Shi-Qiang Gao, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 547 days.

(21) Appl. No.: 13/497,729

(22) PCT Filed: Sep. 15, 2010

(86) PCT No.: PCT/SG2010/000339

§ 371 (c)(1),
(2), (4) Date: Mar. 22, 2012

(87) PCT Pub. No.: WO2011/040880

PCT Pub. Date: Apr. 7, 2011

(65) Prior Publication Data

US 2012/0240288 A1 Sep. 20, 2012

Related U.S. Application Data

(60) Provisional application No. 61/246,597, filed on Sep. 29, 2009.

(51) Int. Cl.
*C12N 15/82* (2006.01)

(52) U.S. Cl.
CPC ..... *C12N 15/8218* (2013.01); *C12N 15/8285* (2013.01); *C12N 15/8286* (2013.01); *Y02A 40/162* (2018.01); *Y02A 40/164* (2018.01)

(58) Field of Classification Search
None
See application file for complete search history.

(56) References Cited

U.S. PATENT DOCUMENTS

2002/0048814 A1 4/2002 Oeller

FOREIGN PATENT DOCUMENTS

WO 2001037654 A2 5/2001
WO WO 0137654 A2 * 5/2001
WO 2007141790 A2 12/2007
WO 2008063203 A2 5/2008
WO 2008067759 A1 6/2008
WO 2008152008 A2 12/2008

OTHER PUBLICATIONS

Valentine et al (2007) Plant Biotechnol. J. 5: 827-834.*
Deleris et al (2006) Science 313: 68-71.*
Harris et al (Development (2001) 128: 2823-2832.*
Mathews et al (1993) Development 117: 977-991.*
Valentine et al (2004) Plant Physiol. 136:3999-4009.*
Liu et al (2002, The Plant Journal, 30 (4): 415-429).*
Mao, Ying-Bo, "Silencing a Cotton Bollworm P450 Monooxygenase Gene by Plant-Mediated RNAi Impairs Larval Tolerance of Gossypol," Nature Biotechnology, vol. 25, No. 11, Nov. 2007, pp. 1307-1313, © 2007 Nature Publishing Group.
Second Chinese Office Action dated Dec. 9, 2013, Application No. 201080053979.9, Applicant: Temasek Life Sciences Laboratory, 13 pages.
Golenberg, Edward M., "Development of a Gene Silencing DNA Vector Derived from a Broad Host Range Geminivirus," Plant Methods, vol. 5 (p. 9), No. 1, Jul. 2009, BioMed Central, London, GB, 14 pages, © 2009 Golenberg et al.; licensee BioMed Central.
Voinnet, Olivier, "Induction and Suppression of RNA Silencing: Insights from Viral Infections," Nature Reviews Genetics, vol. 6, No. 3, Feb. 2005, pp. 206-220 and online summary page, © 2005 Nature Publishing Group.
Extended European Search Report dated Mar. 27, 2014, Application No. 14153986.6-1406, Reference SHD/P43169EP-D1, Applicant: Temasek Life Sciences Laboratory, 9 pages.
Extended European Search Report—Application No. 10820916.4-1406 / 2483410 PCT/SG2010000339; dated Jul. 25, 2013; Reference: RDO/P43169EP; Applicant: Temasek Life Sciences Laboratory Limited, 14 pages.
Dong, Y. et al., "A Ligation-Independent Cloning Tobacco Rattle Virus Vector for High-Throughput Virus-Induced Gene Silencing Identifies Roles for NbMADS4-1 and -2 in Floral Development," Plant Physiology, Dec. 2007, vol. 145, pp. 1161-1170 plus 19 supplemental pages, © 2007 American Society of Plant Biologists.
Saedler, R. et al., "Virus-Induced Gene Silencing of Jasmonate-Induced Direct Defences, Nicotine and Trypsin Proteinase-Inhibitors in Nicotiana Attenuata," Journal of Experimental Botany, Crosstalk in Plant Signal Transduction Special Issue, Jan. 2004, vol. 55, No. 395, pp. 151-157, © 2004 Society for Experimental Biology.
AU Search Report and Written Opinion, dated Jul. 11, 2013; AU Application No. 201201683-8; Filing Date: Sep. 15, 2010: Applicant: Temasek Life Sciences Laboratory Limited, 17 pages.

(Continued)

*Primary Examiner* — Stuart F Baum
(74) *Attorney, Agent, or Firm* — Rothwell, Figg, Ernst & Manbeck, P.C.

(57) ABSTRACT

The present invention relates to the field of controlling pests, such as insects, using a virus to express pest genes in hosts. More specifically, the present invention relates to a method for rapidly screening for pest genes which can lead to mortality of the pest when the pest has ingested host tissues expressing virus-linked pest gene sequences. The present invention also relates to a method for controlling pests by viral expression of target pest sequences to modify endogenous expression of pest genes in cells or tissues of the pest.

22 Claims, 6 Drawing Sheets

(56) References Cited

OTHER PUBLICATIONS

Dubreuil, G. et al., "Tobacco Rattle Virus Mediates Gene Silencing in a Plant Parasitic Root-Knot Nematode," Journal of Experimental Botany 2009, vol. 60, pp. 4041-4050, Advance Access Published Jul. 22, 2009.

Valentine, T.A. et al., "Delivery of Macromolecules to Plant Parasitic Nematodes Using a Tobacco Rattle Virus Vector," Plant Biotechnology Journal 2007, vol. 5, pp. 827-834.

* cited by examiner

Mortality of CBM groups feed with cotton leaves (%)

0 10 20 30 40 50 60 70 80 90 100

| Group | Mortality (%) |
|---|---|
| JcCurcin | 15.5 |
| GhDCS | 8.3 |
| GhCYP 6AE14 | 25.0 |
| HaGST1 | 36.8 |
| HaVATP | 31.7 |
| HaCHT | 28.3 |
| HaTub | 41.8 |
| HaTub+Ha CG4572 | 46.7 |
| HaTub+ HaDCR1 | 73.3 |

Mortality of CBM groups feed with *N. benthamiana* leaves (%)

100
90
80
70
60
50
40
30
20
10
0

| | |
|---|---|
| *JcCurcin* | 16.6 |
| *HaGST1* | 60.6 |
| *HaVATP* | 46.0 |
| *HaCHT* | 52.8 |
| *HaTub* | 64.7 |
| *HaTub+HaCG4572* | 62.5 |
| *HaTub+HaDCR1* | 79.4 |
| *HaTub+NbDCL4* | 84.2 |

Mortality of CBM groups feed with *N. benthamiana* leaves (%)

0 10 20 30 40 50 60 70 80 90

| | JcCurcin | Sense-HaTub | Antisese-HaTub | Hairpin-HaTub |
|---|---|---|---|---|
| Mortality (%) | 15 | 72.5 | 60 | 50 |

CONTROL OF PESTS IN PLANTS

CROSS-REFERENCE TO RELATED APPLICATION

The present application is a national stage filing under 35 U.S.C. § 371 of PCT/SG2010/000339, filed on 15 Sep. 2010 which in turn claims priority to U.S. provisional patent application Ser. No. 61/246,597 filed 29 Sep. 2009, each application is incorporated herein by reference.

SEQUENCE SUBMISSION

The present application is being filed along with a Sequence Listing in electronic format. The Sequence Listing is entitled 2577_197PCT_Sequence_Listing.txt, created on 25 Aug. 2010. The information in the electronic format of the Sequence Listing is part of the present application and is incorporated herein by reference in its entirety.

BACKGROUND OF THE INVENTION

The present invention relates to the field of controlling pests, such as insects, using a virus to express pest genes in hosts. More specifically, the present invention relates to a method for rapidly screening for pest genes which can lead to mortality of the pest when the pest has ingested host tissues expressing virus-linked pest gene sequences. The present invention also relates to a method for controlling pests by viral expression of target pest sequences to modify endogenous expression of pest genes in cells or tissues of the pest.

The publications and other materials used herein to illuminate the background of the invention or provide additional details respecting the practice, are incorporated by reference, and for convenience are respectively grouped in the Bibliography.

The earth is full of diverse pest problems and a larger number of methods have been utilized for attempting to control infestations by these pests. Compositions for controlling infestations by microscopic pests such as bacteria, fungi and viruses have been provide in the form of antibiotic compositions, antiviral compositions, and antifungal compositions. Compositions for controlling infestations by larger pests such as nematodes, flatworm, roundworms, pinworms, heartworms, tapeworms, trypanosomes, schistosomes, and the like have typically been in the form of chemical compositions which can either be applied to the surfaces of substrates on which pests are known to infest, or to be ingested by an infested animal in the form of pellets, powders, tablets, pastes, or capsules and the like.

Commercial crops are often the targets of insect attack. Chemical pesticides have been very effective in eradicating pest infestations. However, it is well known that there are several disadvantages to using chemical pesticidal agents. First of all, chemical pesticidal agents are not selective, therefore, on the same time of controlling target insect, because of the lack of selectivity, they also exert their effects on non-target fauna, often effectively sterilizing a field for a period of time over which the pesticidal agents have been applied. Second, chemical pesticidal agents persist in the environment and generally are slow to be metabolized, if at all. They accumulate in the food chain, and finally in the high predator species, such as human being, where these pesticidal agents act as a mutagens and/or carcinogens, to cause irreversible and deleterious genetic modifications. This kind of accumulation causes to higher predator pest resistance. Thus there has been a long felt need for environmentally friendly methods for controlling or eradicating insect infestation on or in plants, i.e., methods which are selective, environmental inset, non-persistent, and biodegradable, and that fit well into pest resistance management schemes. These environmental safe compositions, including *Bacillus thuringiensis* (Bt) bacteria and transgenic plants expressing one or more genes encoding insecticidal Bt protein, have been remarkably efficient in controlling insect pest infestation. However, with the increased use of Bt crops, such as corn and cotton, comes the threat that target pests may develop resistance to these toxins. Although Bt-resistant insect populations have not yet been observed in the field, resistant strains have been developed in the laboratory by selection with toxin-impregnated diet (McGaughy, 1985). Thus, beside to work out ways to delay Bt resistance development, it is greatly valuable to find a different mode of action to control pest infestations by single use or combined use with Bt expression strategy.

Double stranded RNA (dsRNA) mediated inhibition of specific genes in eukaryotic organisms, has been used to silence genes and study gene function in few insect such as coleopteran *Tribolium castaneum* (Bucher et al., 2002) previously. Normal delivery of dsRNA to mediate dsRNA-involved genetic control includes generating transgenic insects that express double stranded RNA molecules or injecting dsRNA solutions into the insect body or within the egg sac prior to or during embryonic development. It is widely believed this method of transgenic expression in insect for controlling insect on field crop would be impractical to provide dsRNA molecules in the diet of most invertebrate pest species or to inject compositions containing dsRNA into the bodies of invertebrate pest. Recently, methods using transgenic plants to generate dsRNA have shown that transgenically expressed dsRNA can enhanced resistance to the economically important agricultural pests cotton bollworm (*Helicoverpa armigera*; Lepidoptera) and Western corn rootworm (WCR; *Diabrotica virgifera virgifera* LeConte; Coleoptera) (Baum et al., 2007; Mao et al., 2007; U.S. published patent application No 2006/0021087). These references have shown the possibility of using dsRNA in the protection of crops against insect infestation. This approach holds great promise for the future because it allows a wide range of potential targets for suppression of gene expression in the insect to be exploited. However, at this moment, these identified genes are still not as effective as transgenic maize engineered to produce a modified Cry3Bb *Bacillus thuringiensis* (Bt) toxin.

Therefore the key to compete or even to replace Bt transgenic plant technology is to identify one or more suitable insect genes by feeding expressed dsRNA in vivo in specific plant-insect pair in the content of huge gene number for each agriculturally important pest (for example, 16,404 gene for the model beetle and pest *Tribolium castaneum*). Previously, one essential technology to evaluate these candidate genes is stable transformation of plants. However, the inefficient production of transgenic plants in some important crops such as cotton limits gene identification on a large scale. Moreover, such procedure is laborious, expensive, time consuming and not suitable for high throughput analysis on a genomic scale.

RNA silencing in plant first was found as a virus resistance as early as 1928 (Wingard, 1928). Wingard described tobacco plants infected with tobacco ringspot virus. The upper leaves had become immune to the virus and consequently were asymptomatic and resistant to secondary infection (Wingard, 1928). Cross protection is therefore widely-used to artificial intervention severe strain virus infection after pre-treated crops with a mild strain in all over the world (Prins et al., 2008). Good examples of diseases control by cross protection were successfully in citrus tristeza and barley yellow dwarf, respectively (Prins et al., 2008).

Infection of plants with both RNA and DNA viruses produces virus-related small interfering RNAs (siRNAs). dsRNA, either derived from a replication intermediate or a secondary-structure characters of some single-stranded viral RNA region, can be accumulated to high levels in virus-infected plant cells. In the case of plant DNA viruses, the dsRNA may be formed by annealing of overlapping complementary transcripts (Baulcombe, 2004). Virus-induced gene silencing for plant gene (VIGS) (Ruiz et al., 1998; Burch-Smith et al., 2004) offers an attractive alternative as it allows the investigation of gene functions without plant transformation in plant gene functional analysis. Recombinant viruses can be constructed carrying an inserted partial sequence of a candidate gene. Such recombinant viruses can move systemically in plants, producing dsRNA (further siRNA) including the inserted fragment of candidate gene that can mediate degradation of the endogenous gene transcripts (Brigneti et al., 2004; Burch-Smith et al., 2004), resulting in silencing of the candidate gene expression in inoculated plants. Depending on the plant species, the effects on endogenous gene expression can usually be assayed 1-2 weeks after virus infection. VIGS can be used as an efficient reverse genetics tool for gene/gene family knock-down in a rapid and high-throughout fashion (Nasir et al., 2005). Because the knock-down phenotype is transient and reversible, this method can be used to access functions of genes whose deficiency may cause embryo lethality (Burch-Smith et al., 2004). Using different injection methods, VIGS has been shown to function in different organs, such as leaves (Liu et al., 2002; Burch-Smith et al., 2006), roots (Valentine et al., 2004; Bhattarai et al., 2007), flowers (Liu et al., 2004; Chen et al., 2005) and even fruits (Fu et al., 2005).

VIGS systems have been successfully applied to assay for gene functions in plants such as Tobacco Rattle Virus in tobacco (Ratcliff et al., 2001), pepper (Chung et al., 2004), tomato (Liu et al., 2002), *Jatropha* (U.S. Provisional Patent Application No. 61/143,484), cotton (U.S. Provisional Patent Application No. 61/185,631) and poppy (Hileman et al., 2005); Tobacco mosaic virus in tobacco (Hiriart et al., 2003) and pepper (Kim et al., 2007); Potato virus X (PVX) in tobacco (Saitoh and Terauchi, 2002) and potato (Faivre-Rampant et al., 2004); Brome mosaic virus (BMV) in rice, barley and maize (Ding et al., 2006); Barley stripe mosaic virus (BSMV) in barley and wheat (Holzberg et al., 2002); Cucumber mosaic virus in soybean (Nagamatsu et al., 2007); Apple latent spherical virus in tobacco, tomato and soybean (Igarashi et al., 2009; Yamagishi and Yoshikawa, 2009); Bean pod mottle virus in soybean (Zhang and Ghabrial, 2006); Pea early browning virus in *Pisum sativum* (Constantin et al., 2008), *Medicago truncatula* and *Lathyrus odoratus* (Grønlund, et al., 2008); plant DNA virus such as Beet curly top virus (Golenberg et al., 2009) and Tomato yellow leaf curl China virus (Huang et al., 2009). For a general review, see Unver and Budak (2009).

Thus, it is desired to provide alternative and selective means for controlling pest infestation. It is also desired to develop a method for the transient and high-throughput functional analysis of pest genes on a genomic scale to identify pest genes to target for pest control. The present invention provides a method for identifying target pest genes and also provides alternative and selective means for controlling pest infestations.

SUMMARY OF THE INVENTION

The present invention relates to the field of controlling pests, such as insects, using a virus to express pest genes in hosts. More specifically, the present invention relates to a method for rapidly screening for pest genes which can lead to mortality of the pest when the pest has ingested host tissues expressing virus-linked pest gene sequences. The present invention also relates to a method for controlling pests by viral expression of target pest sequences to modify endogenous expression of pest genes in cells or tissues of the pest.

Thus in a first aspect, the present invention provides a method of screening pest genes to identify pest genes which can lead to mortality of the pest when expression of the pest gene is silenced in the pest. In accordance with this aspect, the method comprises:

(a) inserting a nucleic acid comprising a sequence of a pest gene to be screened into a virus-induced gene silencing (VIGS) vector of a virus that can infect a desired host to produce a modified VIGS vector;

(b) inoculating the host with the modified VIGS vector to produce infected host;

(c) growing the infected host under conditions in which the modified VIGS vector is replicated to produce RNA which accumulates in tissue of the host;

(d) feeding the host tissue with RNA to pests; and (e) determining whether the RNA is toxic to the pest, wherein pest toxicity identifies the pest gene as a pest gene that leads to mortality of the pest when the pest gene expression is silenced in the pest.

In one embodiment, the pest is an insect. In another embodiment, the host is a plant. In an additional embodiment, the VIGS vector is derived from a virus that can infect a desired host, such as a plant. In some embodiments, the modified VIGS vector comprises a single vector that includes the nucleic acid. In other embodiments, the VIGS vector comprises two vectors, one of which is modified to include the nucleic acid. In some embodiments, the virus is a DNA virus. In other embodiments, the virus is an RNA virus. In one embodiment, the host, such as a plant, is inoculated with the modified VIGS vector by inoculation with virus particles. In another embodiment, the host is inoculated by *Agrobacterium* infiltration, such as by syringe infiltration or vacuum infiltration or agro-drench or other inoculation methods to generate virus particles through *agrobacterium* infection as an intermediate step. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission or by other natural methods of transmission.

In one embodiment, the RNA is double stranded RNA (dsRNA). In another embodiment, the RNA is small interfering RNA (siRNA), which may be in the form of a short hairpin RNA (shRNA). In a further embodiment, the RNA is single stranded RNA (ssRNA). The RNA may be produced in the host from the modified VIGS vector as described herein.

In another aspect, the present invention provides a method of controlling pests by viral expression of target pest sequences in a host to modify endogenous expression of pest genes in cells or tissues of the pest. In accordance with this aspect, the method comprises:

(a) inserting a nucleic acid comprising a sequence of a desired pest gene to be silenced, in the sense or antisense orientation or as an inverted repeat, into a virus-induced gene silencing (VIGS) vector of a virus that can infect a desired host to produce a modified VIGS vector;

(b) inoculating the host with the modified VIGS vector to produce infected host; and (c) growing the infected host under conditions in which the modified VIGS vector is replicated to produce RNA which accumulates in tissue of the host, wherein the RNA causes gene silencing in the pest upon ingestion of the RNA produced in the host, whereby pests are controlled.

In one embodiment, the pest is an insect. In another embodiment, the host is a plant. In an additional embodiment, the VIGS vector is derived from a virus that can infect a desired host, such as a plant. In some embodiments, the modified VIGS vector comprises a single vector that includes the nucleic acid. In other embodiments, the VIGS vector comprises two vectors, one of which is modified to include the nucleic acid. In some embodiments, the virus is a DNA virus. In other embodiments, the virus is an RNA virus. In one embodiment, the host, such as a plant, is inoculated with the modified VIGS vector by inoculation with virus particles. In another embodiment, the host is inoculated by *Agrobacterium* infiltration, such as by syringe infiltration or vacuum infiltration. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission or by other natural methods of transmission.

In one embodiment, the RNA is double stranded RNA (dsRNA). In another embodiment, the RNA is small interfering RNA (siRNA), which may be in the form of a short hairpin RNA (shRNA). In a further embodiment, the RNA is single stranded RNA (ssRNA). The RNA may be produced in the host from the modified VIGS vector as described herein.

In one embodiment, the present invention uses a recombinant plant virus RNA sequence expressed in host plants to effect heterologous silencing in insect pests which ingest these RNA sequences. The invention is not restricted to the use of any single virus, such as TRV, but also includes the use of any plant DNA or RNA virus as described hereing, (e.g., Geminivirus, BSMV, BMV, PVX, CMV, etc) in those crops (such as monocot plants, including rice, wheat, barley, maize, etc. and dicot plants including cotton, *Jatropha*, tobacco, tomato, potato, soybean etc.) and other plants which may be infected by plant viruses.

In still another embodiment, non-pathogenic, attenuated strains of microorganisms may be used as a carrier for the insect control agents and, in this perspective, the microorganisms carrying such agents are also referred to as insect control agents. The microorganisms may be engineered to express a recombinant plant virus nucleotide sequence with an insect target gene to produce RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the RNA molecules or fragments or derivatives thereof.

In a further embodiment, there are mild strains of viruses which do not elicit any symptoms on host plants but can protect the hosts from subsequent infection by a severe virus strain. Such mild virus strains which are said to be attenuated and can confer cross protection have been used in field experiments in several countries for virus resistance. In accordance with the present invention, it is possible to use such mild virus strains to produce pest sequences in host plants. Infected host plants would be resistant to subsequent infection by the severe strain of virus and also tolerant to pests (insect). These mild strains usually produce a weak suppressor of gene silencing so that viral RNAs are not completely degraded by the host machinery. In one embodiment, the present invention utilizes a synthetic TRV to demonstate that a mild strain of TRV infection induces no obvious morphological phentoypes in cotton and weak phenotypes in tobacco. In a further embodiment, the present invention utilizes recombinant virus to produce pest sequences in host plants by inoculation with virus particles. In another embodiment, the host is inoculated by *Agrobacterium* infiltration, such as by sprayer inoculation, syringe infiltration or vacuum infiltration, or agro-drench or other inoculation methods to generate virus particles through *agrobacterium* infection as an intermediate step. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission or by other natural methods of transmission. In another embodiment, recombinant virus RNA embedded with target insect gene can be in vitro transcribed and were further used to infected plants to confer plants with insect resistance. In additional embodiment, a transgenic event that produces recombinant virus provides protection from invertebrate pest infestation that is within the preferred effectiveness range against a target pest. In addition, it is well known to the skilled artisan that there are situations where it is advantageous to have such transgenic events within the preferred range of effectiveness.

It is envisioned that the compositions of the present invention can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event.

The present invention also includes seeds and plants having more that one transgenic event. Such combinations are referred to as "stacked" transgenic events. These stacked transgenic events can be events that are directed at the same target pest, or they can be directed at different target pests. In one preferred method, a seed having the ability to express a Cry3 protein or insecticidal variant thereof also has the ability to express at least one other insecticidal agent including but not limited to a protein that is different from a Cry3 protein and/or an RNA molecule the sequence of which is derived from the sequence of an recombinant virus RNA expressed in a target plant and that forms silencing upon expressing, in the seed or cells of a plant grown from the seed, wherein the ingestion of one or more cells of the plant by the target pest results in the suppression of expression of the RNA in the cells of the target pest.

DETAILED DESCRIPTION OF THE INVENTION

Figure 1:
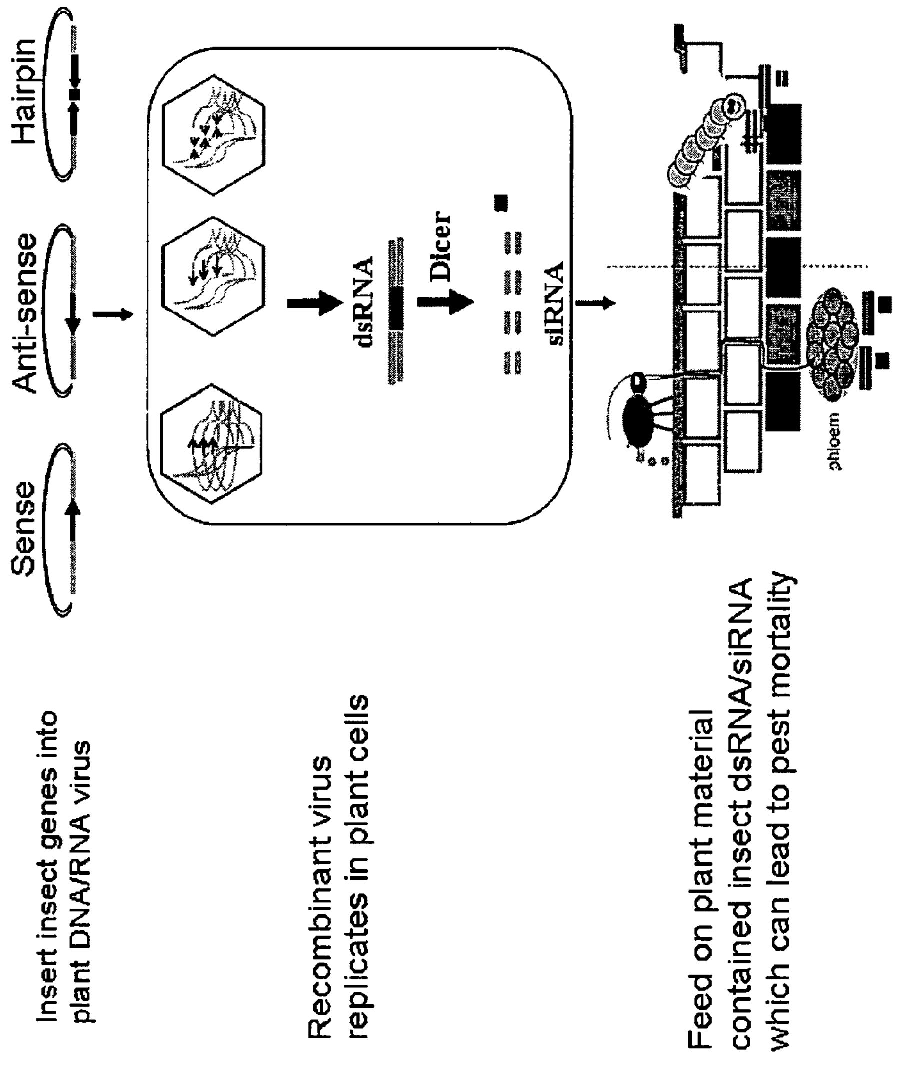
FIG. 1 illustrates a rapid recombinant virus method to screen for insect genes which can lead to mortality when expression is silenced.

The present invention relates to the field of controlling pests, such as insects, using a virus to express pest genes in hosts. More specifically, the present invention relates to a method for rapidly screening for pest genes which can lead to mortality of the pest when the pest has ingested host tissues expressing virus-linked pest gene sequences. The present invention also relates to a method for controlling pests by viral expression of target pest sequences to modify endogenous expression of pest genes in cells or tissues of the pest.

The present invention utilizes recombinant DNA technologies to silence or inhibit expression of a target sequences in the cell of a pest, by feeding to the pest one or more viral RNA sequences carrying (a) a portion (part) of a target coding sequence, (b) a portion of a target 5' UTR sequence, (c) a portion of a target 3' UTR sequence, (d) a protion of a target 5' UTR and a portion of a target coding sequence or (e) a portion of a target coding sequence and a portion of a target 4' UTR sequence in (i) sense, (ii) antisense, or (iii) hairpin double stranded structure, thereby controlling the pest. In one embodiment, the length of the target sequences is in the range of about 50 nucleotides to about 2000 nucleotides and higher. In another embodiment, the length of the target sequences is in the range of about 150 to about 1500 nucleotides. In a further embodiment, the length of the target sequences is about 200 to about 1200 nucleotides. In another embodiment, the length of the target sequences is about 300 to about 1000 nucleotides. In a further embodiment, the length of the target sequences is about 300 to about 800 nucleotides. It is preferred to use a length of the target sequences of about 300 to about 1000 nucleotides. Further specifically, using a recombinant plant DNA or RNA virus sequence expressed in host plants to effect heterologous silencing in insect pests which ingest these corresponding RNA sequences. Compositions containing the RNA nucleotide sequences of the present invention for use in topical applications onto plants or onto animals or into the environment of an animal to achieve the elimination or reduction of a pest is also described. The present invention also utilizes a virus as an expression vector to transiently transcribe RNA in order to quickly evaluate one or more nucleic acid molecules and recombinant DNA sequences for controlling pests. Using this method, several insect genes that can lead to mortality when silenced are also described.

The present invention relates to the use of heterologous virus-induced gene silencing (VIGS) to evaluate genes or target sequences in killing insects reliably and rapidly, and in a high-throughput manner. The present invention provides an efficient and reproducible system and procedure for VIGS in insect. In one embodiment, the present invention provides for the co-silencing of two genes to enhance the efficiency of controlling insects.

The present invention comprises a method of inhibiting expression of a target gene in an invertebrate pest. Inhibition of expression is also referred to herein as gene silencing. Specifically, the present invention comprises a method of modulating or inhibiting expression of one or more target genes in an invertebrate pest, such as an insect, that cause cessation of feeding, growth, development, reproduction and infectivity and eventually result in the death of the pest. Briefly, this method involves the expression in a host, such as a host plant, of a pest-related sequence contained within a viral RNA sequence (dsRNA or siRNA specific for a pest target sequence). In one embodiment, the pest RNA sequence (dsRNA or siRNA) is produced as a result of the replication of a virus containing a nucleic acid comprising a pest target sequence. When host plants are inoculated with a recombinant virus containing a target pest sequence, the virus will replicate and the pest sequence linked to the viral RNA (dsRNA or siRNA) will accumulate in systemic leaves. The host plant can be inoculated by *agrobacterium* infiltration (such as syringe infiltration or vacuum infiltration), particle bombardment, virus particles directly, vector transmission (such as Bacteria, Fungi, Nematodes, Arthropods and Arachnids), mechanical transmission (such as rubbing virus-containing preparations into the plant parts such as leaves) or other natural methods of transmission. These leaves are then used as a diet to feed insects. If the viral RNA-linked pest sequence (insect dsRNA or siRNA) is toxic, it would cause mortality when ingested. Therefore, this is a rapid and high-throughput method to screen for insect genes that may lead to mortality when silenced.

The method comprises introduction of recombinant virus carrying pest sequences (expressed dsRNA or its modified forms such as small interfering RNAs (siRNA)) sequences, into the cells or into the extracellular environment of a pest, such as the midgut of an insect, within an invertebrate pest body wherein the viral RNA-pest sequences (dsRNA or siRNA) enters the cells and inhibits expression of at least one or more target genes and wherein inhibition of the one or more target genes causes cessation of feeding, growth, development, reproduction and infectivity and eventually results in the death of the invertebrate pest. It is specifically contemplated that the methods and compositions of the present will be useful in rapid screening genes useful for limiting or eliminating invertebrate pest infestation in or on any pest host plants, which is also a plant virus host.

The present invention also relates to a method that, instead of using dsRNA, uses single stranded RNA (ssRNA) (in sense or antisense orientation) in the virus. Although the exact mechanism is not known, it is possible, because of the plant virus, that the ssRNA can have a replication intermediate or a secondary-structure characteristics of some single-stranded viral RNA region to form dsRNA. However, the key is that the sequence is not presented as a dsRNA construct but as an ssRNA construct in a sense orientation or an antisense orientation. RNA silencing in plants can be derived directly from the ssRNA of viral genome or via the action of host-encoded RNA-dependent RNA polymerases (RDRs) to mediate degradation of homologous RNA sequences including the virus genome. As shown herein, the incorporation of ssRNA in the viral RNA is a potent antipest defense mechanism. The exact mechanism of this potent antipest defense mechanism is not known.

Thus in a first aspect, the present invention provides a method of screening pest genes to identify pest genes which can lead to mortality of the pest when expression of the pest gene is silenced in the pest. A method in accordance with one embodiment of this aspect of the present invention is shown in FIG. 1. In accordance with this aspect, the method comprises:

(a) inserting a nucleic acid comprising a sequence of a pest gene to be screened into a virus-induced gene silencing (VIGS) vector of a virus that can infect a desired host to produce a modified VIGS vector;

(b) inoculating the host with the modified VIGS vector to produce infected host;

(c) growing the infected host under conditions in which the modified VIGS vector is replicated to produce RNA which accumulates in tissue of the host;

(d) feeding the host tissue with RNA to pests; and (e) determining whether the RNA is toxic to the pest, wherein pest toxicity identifies the pest gene as a pest gene that leads to mortality of the pest when the pest gene expression is silenced in the pest.

In one embodiment, the RNA is double stranded RNA (dsRNA). In another embodiment, the RNA is small interfering RNA (siRNA), which may be in the form of a short hairpin RNA (shRNA). In a further embodiment, the RNA is single stranded RNA (ssRNA). The RNA may be produced in the host from the modified VIGS vector as described herein. In this aspect of the invention, it is preferred that the RNA is dsRNA.

In one embodiment, the pest is an insect. In another embodiment, the host is a plant. In an additional embodiment, the VIGS vector is derived from a virus that can infect a desired host, such as a plant. In some embodiments, the modified VIGS vector comprises a single vector that includes the nucleic acid. In other embodiments, the VIGS vector comprises two vectors, one of which is modified to include the nucleic acid. In some embodiments, the virus is a DNA virus. In other embodiments, the virus is an RNA virus. In one embodiment, the host, such as a plant, is inoculated with the modified VIGS vector by inoculation with virus particles. In another embodiment, the host is inoculated by *Agrobacterium* infiltration, such as by syringe infiltration or vacuum infiltration. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission, such as by rubbing virus containing preparations into host tissue or by other natural methods of transmission.

Potential pest genes for screening include those that encode an essential protein, such as one involved in development regulation, physiological or metabolic aspects of the pest. The predicted function of potential pest genes can be selected from the group consisting metabolic pathways such as energy metabolism and detoxification protein, organ or tissue differentiation and development regulation including small RNA biosynthesis, molting processing, and cytoskeleton protein.

Figure 2:
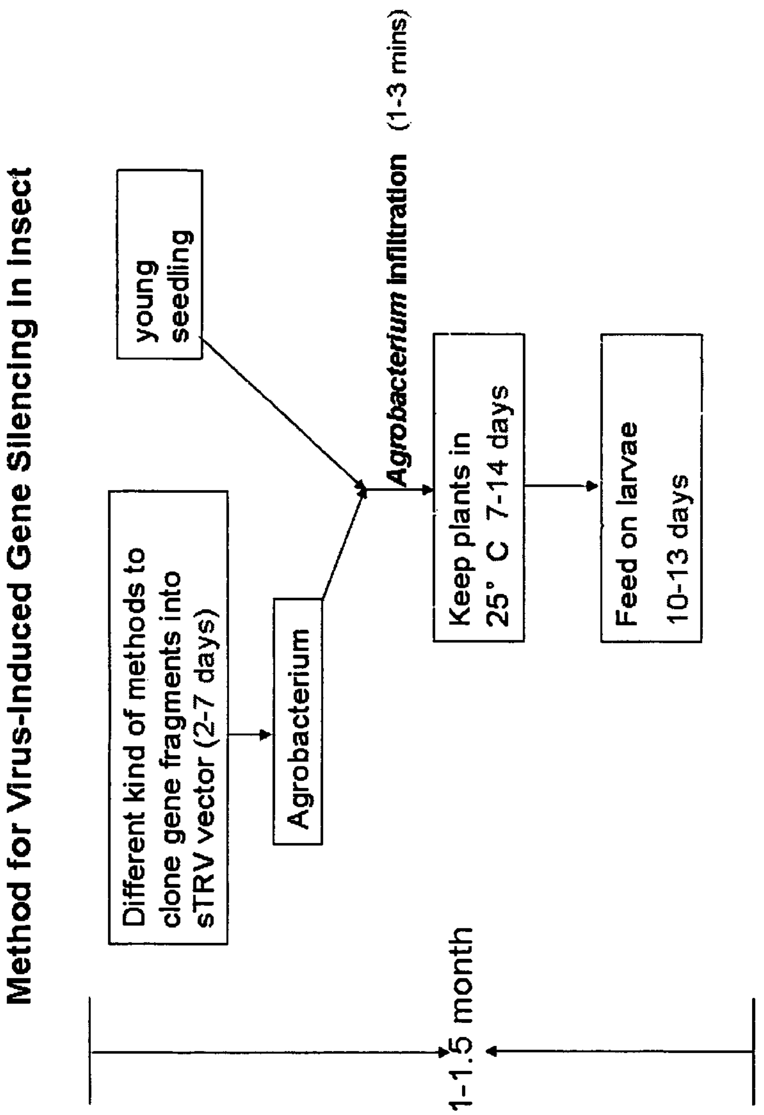
FIG. 2 illustrates a transient VIGS method for controlling insects in accordance with one embodiment of the present invention.

In a second aspect, the present invention provides a method of controlling pests by viral expression of target pest sequences in a host to modify endogenous expression of pest genes in cells or tissues of the pest. A method in accordance with one embodiment of this aspect of the present invention is shown in FIG. 2. In accordance with this aspect, the method comprises:

(a) inserting a nucleic acid comprising a sequence of a desired pest gene to be silenced into a virus-induced gene silencing (VIGS) vector of a virus that can infect a desired host to produce a modified VIGS vector;

(b) inoculating the host with the modified VIGS vector to produce infected host; and (c) growing the infected host under conditions in which the modified VIGS vector is replicated to produce RNA which accumulates in tissue of the host, wherein the RNA causes gene silencing in the pest upon ingestion of the dsRNA produced in the host, whereby pests are controlled.

In one embodiment, the pest is an insect. In another embodiment, the host is a plant. In an additional embodiment, the VIGS vector is derived from a virus that can infect a desired host, such as a plant. In some embodiments, the modified VIGS vector comprises a single vector that includes the nucleic acid. In other embodiments, the VIGS vector comprises two vectors, one of which is modified to include the nucleic acid. In some embodiments, the virus is a DNA virus. In other embodiments, the virus is an RNA virus. In one embodiment, the host, such as a plant, is inoculated with the modified VIGS vector by inoculation with virus particles. In another embodiment, the host is inoculated by *Agrobacterium* infiltration, such as by syringe infiltration or vacuum infiltration. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission, such as by rubbing virus containing preparations into host tissue or by other natural methods of transmission. In one embodiment, the pest target gene is as described above.

In one embodiment, the RNA is double stranded RNA (dsRNA). In another embodiment, the RNA is small interfering RNA (siRNA), which may be in the form of a short hairpin RNA (shRNA). In a further embodiment, the RNA is single stranded RNA (ssRNA). The RNA may be produced in the host from the modified VIGS vector as described herein.

In one embodiment, the present invention uses a recombinant plant virus RNA sequence expressed in host plants to effect heterologous silencing in insect pests which ingest these RNA sequences. The invention is not restricted to the use of any single virus, such as TRV, but also includes the use of any plant DNA or RNA virus as described hereing, (e.g., Geminivirus, BSMV, BMV, PVX, CMV, etc) in those crops (such as monocot plants, including rice, wheat, barley, maize, etc. and dicot plants including cotton, *Jatropha*, tobacco, tomato, potato, soybean etc.) and other plants which may be infected by plant viruses.

In still another embodiment, non-pathogenic, attenuated strains of microorganisms may be used as a carrier for the insect control agents and, in this perspective, the microorganisms carrying such agents are also referred to as insect control agents. The microorganisms may be engineered to express a recombinant plant virus nucleotide sequence with an insect target gene to produce RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the RNA molecules or fragments or derivatives thereof.

In a further embodiment, there are mild strains of viruses which do not elicit any symptoms on host plants but can protect the hosts from subsequent infection by a severe virus strain. Such mild virus strains which are said to be attenuated and can confer cross protection have been used in field experiments in several countries for virus resistance. In accordance with the present invention, it is possible to use such mild virus strains to produce pest sequences in host plants. Infected host plants would be resistant to subsequent infection by the severe strain of virus and also tolerant to pests (insect). These mild strains usually produce a weak suppressor of gene silencing so that viral RNAs are not completely degraded by the host machinery. In one embodiment, the present invention utilizes a synthetic TRV to demonstate that a mild strain of TRV infection induces no obvious morphological phentoypes in cotton and weak phenotypes in tobacco. In a further embodiment, the present invention utilizes recombinant virus to produce pest sequences in host plants by inoculation with virus particles. In another embodiment, the host is inoculated by *Agrobacterium* infiltration, such as by sprayer inoculation, syringe infiltration or vacuum infiltration, or agro-drench or other inoculation methods to generate virus particles through *agrobacterium* infection as an intermediate step. In a further embodiment, the host is inoculated by particle bombardment. In an additional embodiment, the host is inoculated by vector transmission, such as by Bacteria, Fungi, Nematodes, Arthropods and Arachnids. In another embodiment, the host is inoculated by mechanical transmission or by other natural methods of transmission. In another embodiment, recombinant virus RNA embedded with target insect gene can be in vitro transcribed and were further used to infected plants to confer plants with insect resistance. In additional embodiment, a transgenic event that produces recombinant virus provides protection from invertebrate pest infestation that is within the preferred effectiveness range against a target pest. In addition, it is well known to the skilled artisan that there are situations where it is advantageous to have such transgenic events within the preferred range of effectiveness.

In one embodiment of the present invention, the VIGS vector is a tobacco rattle virus (TRV). In this embodiment, the nucleic acid is inserted to a TRV RNA2 sequence to produce a modified TRV RNA2 vector. A mixed *Agrobacterium* culture of *Agrobacterium* containing a TRV RNA1 vector and *Agrobacterium* containing the modified TRV RNA2 vector is prepared and used to inoculate the host plant. In one embodiment, the vector comprising TRV RNA2 and the vector comprising TRV RNA1 are synthetic plant vectors. In another embodiment, the sequence of the first desired gene is the sequence of a sense strand of the gene. In an additional embodiment, the sequence of the first desired gene is the sequence of an antisense strand of the gene. In an additional embodiment, the sequence of the first desired gene is the sequence of hairpin structure of the gene. In a further embodiment, the nucleic acid further comprises a sequence of a second desired gene to be silenced. In one embodiment, the second desired gene is host plant virus resistance gene. In another embodiment, the plant virus resistance gene is selected from the group consisting of RNase III Dicer-like 4 (DCL4) gene, RNase III Dicer-like 2 (DCL2) gene, RNase III Dicer-like 3 (DCL3) gene, ARGONAUTE1 (AGO1), ARGONAUTE71 (AGO7), RNA-dependent RNA polymerase 1 (RDR1), RNA-dependent RNA polymerase 6 (RDR6), Suppressor of gene silencing 1 (SGS1), Suppressor of gene silencing 3 (SGS3), and Silencing defective 3 (SDE3). In a further embodiment, the second desired gene is insect small RNA biosynthesis gene. In another embodiment, the small RNA biosynthesis gene is selected from the group consisting of Dicer-1 (DCR1) gene, Pasha gene, Loquacious gene (Loqs), ARGONAUTE1 gene (AGO1), ARGONAUTE2 gene (AGO2), ARGONAUTE3 gene (AGO3), Piwi gene, Stellate gene, Aubergine gene (Aub). In a further embodiment, the nucleic acid comprises sequences of more than two desired genes to be silenced.

As described herein, the present invention relates to a method of inhibiting expression of a target gene in an invertebrate pest. Specifically, the present invention comprises a method of modulating or inhibiting expression of one or more target genes in an invertebrate pest that cause cessation of feeding, growth, development, reproduction and infectivity and eventually result in the death of the insect. The method comprises introduction of virus expressed partial single-stranded RNA (ssRNA) or its modified forms such as small interfering RNAs (siRNA) sequences, into the cells or into the extracellular environment, such as the midgut, within an invertebrate pest body wherein the dsRNA or siRNA enters the cells and inhibits expression of at least one or more target genes and wherein inhibition of the one or more target genes exerts a deleterious effect upon the invertebrates pest. In addition to controlling pests, the present invention is useful in rapidly screening genes to identify those useful for limiting or eliminating invertebrate pest infestation in or on any host, such as a plant. The present invention is illustrated herein with reference to cotton bollworm (*Helicoverpa armigera*; Lepidoptera) as the pest. However, it is understood that the invention is applicable to any pest, such as those disclosed herein. The present invention is also illustrated using cotton or tobacco as the host plant. However, it is understood that the invention is applicable to any host plant, such as those disclosed herein. The present invention is further illustrated using TRV as the VIGS system. However, it is understood that the invention can use any VIGS system, such as those disclosed herein.

Infection of plants with both RNA and DNA viruses produces virus-related small interfering RNAs (siRNAs). dsRNA, either derived from a replication intermediate or a secondary-structure characters of some single-stranded viral RNA region, can be accumulated to high level in virus-infected plant cells. In the case of plant DNA viruses, the dsRNA may be formed by annealing of overlapping complementary transcripts (Baulcombe, 2004). Virus-induced gene silencing (VIGS) (Ruiz et al., 1998; Burch-Smith et al., 2004) offers an attractive alternative as it allows the investigation of gene functions without plant transformation. Recombinant viruses can be constructed carrying an inserted partial sequence of a candidate gene. Such recombinant viruses can move systemically in plants, producing dsRNA (which can be modified to siRNA) including the inserted fragment of candidate gene that can mediate degradation of the endogenous gene transcripts (Brigneti et al., 2004; Burch-Smith et al., 2004), resulting in silencing of the candidate gene expression in inoculated plants. Depending on the plant species, the effects on endogenous gene expression can usually be assayed 1-2 weeks after virus infection. VIGS can be used as an efficient reverse genetics tool for gene/gene family knock-down in a rapid and high-throughout fashion (Nasir et al., 2005). Because the knock-down phenotype is transient and reversible, this method can be used to access functions of genes whose deficiency may cause embryo lethality (Burch-Smith et al., 2004). Using different injection methods, VIGS has been shown to function in different organs, such as leaves (Liu et al., 2002; Burch-Smith et al., 2006), roots (Valentine et al., 2004; Bhattarai et al., 2007), flowers (Liu et al., 2004; Chen et al., 2005) and even fruits (Fu et al., 2005).

The TRV VIGS system has been successfully applied to assay for gene functions in herbaceous plants. such as Tobacco Rattle Virus in tobacco (Ratcliff et al., 2001), pepper (Chung et al., 2004), tomato (Liu et al., 2002), barley (Holzberg et al., 2002), soybean (Fu et al., 2006; Nagamatsu et al., 2007), *Medicago truncatula* (Constantin et al., 2008) and poppy (Hileman et al., 2005), as well as others.

The TRV VIGS system has been successfully applied in some plants such as *Arabidopsis* (Burch-Smith et al., 2006), *Capsicum annuum* (Chung et al., 2004), *Lycopersicon esculentum* (Liu et al., 2002; Dinesh Kumar et al., 2007), *Petunia hybrida* (Chen et al., 2005), *Nicotiana benthamian* (Liu et al., 2002), *Solanum tuberosum* (Brigneti et al., 2004), *Jatropha curcas* (U.S. Provisional Patent Application No. 61/143,484), cotton species (U.S. Provisional Patent Application No. 61/185,631), as well as other putative plants listed in Plant Virus Online (http colon backslash backslash image dot fs dot uidaho dot edu backslash vide backslash descr808 dot htm).

Thus, VIGS systems that can be used in accordance with the present invention include, but are not limited to, Tobacco Rattle Virus in tobacco (Ratcliff et al., 2001), pepper (Chung et al., 2004), tomato (Liu et al., 2002), *Jatropha* (U.S. Provisional Patent Application No. 61/143,484), cotton (U.S. Provisional Patent Application No. 61/185,631) and poppy (Hileman et al., 2005); Tobacco mosaic virus in tobacco (Hiriart et al., 2003) and pepper (Kim et al., 2007); PVX in tobacco (Saitoh and Terauchi, 2002) and potato (Faivre-Rampant et al., 2004); BMV in rice, barley and maize (Ding et al., 2006); BSMV in barley and wheat (Holzberg et al., 2002); Cucumber mosaic virus in soybean (Nagamatsu et al., 2007); Apple latent spherical virus in tobacco, tomato and soybean (Igarashi et al., 2009; Yamagishi and Yoshikawa, 2009); Bean pod mottle virus in soybean (Zhang and Ghabrial, 2006); Pea early browning virus in *Pisum sativum* (Constantin et al., 2008), *Medicago truncatula* and *Lathyrus odoratus* (Grønlund, et al., 2008); plant DNA virus such as Beet curly top virus (Golenberg et al., 2009) and Tomato yellow leaf curl China virus (Huang et al., 2009). For a general review, see Unver and Budak (2009).

Insects that may cause damage in plants generally belong to three categories based upon their methods of feeding and these three categories are, respectively, chewing, sucking and boring insects that belong to the Orders Coleoptera, Lepidoptera, Diptera, Orthoptera, Heteroptera, Ctenophalides, Arachnidiae, and Hymenoptera. It has been found that the present method is useful to protect seeds and plants against a wide array of agricultural insect pests.

When an insect is the target pest for the present invention, such pests include but are not limited to: from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp, *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia Nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia* ni and *Yponomeuta* spp.;

from the order Coleoptera, for example, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Oycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.;

from the order Orthoptera, for example, *latta* spp., *Blattella* spp., *Gryllotalpa* spp., *Leucophaea maderae, Locusta* spp., *Periplaneta* ssp., and *Schistocerca* spp.;

from the order Isoptera, for example, *Reticulitemes* ssp; from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Mallophaga, for example, *Damalinea* spp. and *Trichodectes* spp.;

from the order Thysanoptera, for example, *Franklinella* spp., *Hercinothrips* spp., *Taeniothrips* spp., *Thrips palmi, Thrips tabaci* and *Scirtothrips aurantii;* from the order Heteroptera, for example, *Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp., *Triatoma* spp., Miridae family spp. such as *Lygus hesperus* and *Lygus lineoloris*, Lygaeidae family spp. such as *Blissus leucopterus*, and Pentatomidae family spp.;

from the order Homoptera, for example, *Aleurothrixus floccosus, Aleyrodes brassicae, Aonidiella* spp., Aphididae, *Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lacanium corni, Lepidosaphes* spp., *Macrosiphus* spp., *Myzus* spp., *Nehotettix* spp., *Nilaparvata* spp., *Paratoria* spp., *Pemphigus* spp., *Planococcus* spp., *Pseudaulacaspis* spp., *Pseudococcus* spp., *Psylla* ssp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Triozae treae* and *Unaspis citri;* from the order Hymenoptera, for example, *Acromyrmex, Atta* spp., *Cephus* spp., *Diprion* spp., Diprionidae, *Gilpinia polytoma, Hoplocampa* spp., *Lasius* spp., *Monomorium pharaonis, Neodiprion* spp, *Solenopsis* spp. and *Vespa* ssp.;

from the order Diptera, for example, *Aedes* spp., *Antherigona soccata, Bibio hortulanus, Calliphora ethrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomysa* spp., *Lucilia* spp., *Melanagromyza* spp., *Musca* ssp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;

from the order Siphonaptera, for example, *Ceratophyllus* spp. and *Xenopsylla cheopis*; and from the order Thysanura, for example, *Lepisma saccharina.*

It is envisioned that the compositions of the present invention can be incorporated within the seeds of a plant species either as a product of expression from a recombinant gene incorporated into a genome of the plant cells, or incorporated into a coating or seed treatment that is applied to the seed before planting. The plant cell containing a recombinant gene is considered herein to be a transgenic event.

The present invention also includes seeds and plants having more that one transgenic event. Such combinations are referred to as "stacked" transgenic events. These stacked transgenic events can be events that are directed at the same target pest, or they can be directed at different target pests. In one preferred method, a seed having the ability to express a Cry3 protein or insecticidal variant thereof also has the ability to express at least one other insecticidal agent including but not limited to a protein that is different from a Cry3 protein and/or an RNA molecule the sequence of which is derived from the sequence of an recombinant virus RNA expressed in a target plant and that forms silencing upon expressing in the seed or cells of a plant grown from the seed, wherein the ingestion of one or more cells of the plant by the target pest results in the suppression of expression of the RNA in the cells of the target pest.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning,* 2nd Ed. (Cold Spring Harbor Laboratory Press, Cold Spring Harbor, N.Y.); Sambrook and Russell, 2001, *Molecular Cloning,* 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology,* 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley—VCH, 2005; Engelke, *RNA Interference* (*RNAi*): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Experimental Procedures

Plant Seedlings:

Tobacco (*Nicotiana benthamiana*) and cotton (*Gossypium hirsutum* L. cv. Coker 312) seeds were propagated in Singapore and were germinated in a greenhouse. Plants of tobacco and cotton were grown in presterilized soil at 25° C. on a 16-h-day/8-h-night cycle. Tobacco seedlings with 3-5 true leaves were used for agroinjection and cotton seedlings with 2-3 true leaves were used for vacuum infiltration.

Cotton Bollworm:

Cotton bollworm (*Helicoverpa armigera*) eggs were obtained from Chinese Academy of Agricultural Sciences and reared in the laboratory at 25° C. and 70% relative humidity on a 14-h-day/10-h-night cycle. The larvae were fed on a modified artificial diet as described. Leaves of tobacco plants (1-2 weeks post-agroinjection) or cotton plants (2-3 weeks post vacuum-infiltration) were used for feeding experiments. For each feeding experiment, synchronous larvae were selected, weighed individually and divided into groups; each group contained 6-12 individuals. After feeding on different diets for indicated days, larvae were weighed and death of each individual was recorded. Statistics of data was performed with student t-test in the Excel program.

Synthetic TRV RNA1 Expression Vector:

Synthetic TRV1 vector full length (7756 bp) sequence including: SphI site, T-DNA right border sequence (152 bp), the duplicated cauliflower mosaic virus (CaMV) 35S enhancer region (752 bp) (Shi et al., 1997) the TRV Ppk20 strain RNA1 (6791 bp), Subterranean Clover Mottle Virus satellite RNA ribozyme sequence (46 bp) and SmaI site sequence. This full length sequence was divided into two parts by an endogenous SalI site. The two parts were separately synthesized and cloned into pGH vector to give two vectors pGH-YeJ-V1-1 and pGH-YeJ-V1-2. The synthetic TRV RNA1 fragments, V1-1, released from pGH-YeJ-V1-1 by treatment with SphI and SalI enzymes, and V1-2, released from pGH-YeJ-V1-2 by treatment with SalI and SmaI enzymes, were linked with the pBIN121 vector treated with SphI and EcoICRI enzymes. The new synthetic TRV RNA1 vector was named psTRV1001. The sequence of the synthetic psTRV1001 is set forth in SEQ ID NO:1. The synthetic TRV RNA1 sequence is the same as the published TRV RNA1 sequence.

Synthetic TRV RNA2 Expression Vector:

Synthetic TRV2 vector full length (2915 bp) sequence including: HindIII site, the duplicated cauliflower mosaic virus (CaMV) 35S enhancer region (752 bp) (Shi et al., 1997) the TRV strain ppk20 RNA2 5'-sequence (1639 bp), multiple cloning site (61 bp), the TRV strain ppk20 RNA2 3'-sequence (396 bp), HpaI site. The full length sequence was synthesized and cloned into pGH vector give pGH-YeJ-V2. The synthetic TRV RNA2 fragment V2 was linked into the pCAMBIA0390 by HindIII and HpaI sites. The new synthetic TRV RNA2 vector was named psTRV2001. The sequence of the synthetic psTRV2002 is set forth in SEQ ID NO:2.

Gene Cloning and Vector Construction:

Gene sequences of three genes HaGST1, HaCHT, HaCYP6AE14, were obtained from the GenBank. Another four genes were cloned by PCR using designed primers of conserved regions shared by homologous gene sequences of *Drosophila melanogaster* (HaDCR1, HaCG4572, HaTub and HaVATP) or plant (NbDCL4). For single gene VIGS, all candidate genes were amplified by PCR from cDNA products of *H. armigera* (CBM) whole body samples, and cloned into the XbaI and BamHI sites of the synthetic vector psTRV2001. For co-silencing vectors; cDNA fragment of the second gene was inserted into KpnI and XhoI sites of the vector. The primers used in cloning the genes are set forth in Table 1, which also includes reference to the sequence of the cloned gene. *Jatropha curcin* gene, encoded for *Jatropha*-specific toxin, was used as a non-insect sequence control in CBM larval feeding experiments (U.S. Provisional Patent Application No. 61/143,484, filed on 9 Jan. 2009; International Patent Application No. PCT/SG2009/000481 filed on 16 Dec. 2009 and published as WO 2010/080071). Meanwhile, the δ-cadinene synthase gene (DCS), encoded an enzyme important for biosynthsis of insect inhibitory toxic phytochemicals gossypol, was used as a positive control in feeding experiments (U.S. Provisional Patent Application No. 61/185,631 filed on 10 Jun. 2009; International Patent Application No. PCT/SG2010/000220 filed on 10 Jun. 2010).

Antisense and Hairpin Structure Construction:

Antisense sequence of HaTub, which is set forth as SEQ ID NO:29, was PCR-amplified using designed primers as set forth in SEQ ID NO:27 and SEQ ID NO:28 (see Table 1) when the psTRV2:Hatub plasmid as template. The amplified PCR product was further cloned into the XbaI and BamHI sites of the synthetic vector psTRV2001. For hpHatub hairpin structure construction, sense fragment was amplified by PCR with PCR primers set forth as SEQ ID NO:30 and SEQ ID NO:31 (see Table 1) and further cloned into the BamHI and EcoRI sites of pSK-intron (Guo et al., 2003), followed insertion of the antisense fragment amplified with PCR primers set forth as SEQ ID NO:32 and SEQ ID NO:33 (see Table 1). The hpHatub hairpin structure was subcloned into the BamHI and XhoI sites of psTRV2001 to give psTRV:hpHa Tub.

TABLE 1

Gene Primers and Gene Sequences

| Gene | Primers: Sequence (5'→3') (SEQ ID NO:) | Cloned Gene (SEQ ID NO:) |
|---|---|---|
| HaCYP6AE14 | F: aatatctagacctccgcgaagatgaagaacatgttcc (3)<br>R: ctccggatccgggaagaactccggg (4) | 859 by (5)<br>GenBank:<br>DQ986461 |
| HaVATP | F: ggaatctagacgacgctgggtatcgtgcaa (6)<br>R: gagaagttgtggggatccgccaac (7) | 763 by (8) |
| HaTub | F: ataattctagacaagcctcttacccggtcgcgc (9)<br>R: aatgcggatccagtgcctccaccgaaggagtg (10) | 506 by (11) |
| HaCG4572 | F: ctatggtacccagttcttctggtactttccygc (12)<br>R: ccatctcgagccatgtgtcccgcgttcctgaccatgayctccac (13) | 1075 by (14) |
| HaCHT1 | F: aaaatctagacctgctccgtacaccaatgctactg (15)<br>R: gtaaggatccgtaatcctcttcagaattgcagacg (16) | 693 by (17)<br>GenBank:<br>AY325496 |
| HaDCR1 | F: caatggtaccgtgccgaaggtcctcagcgacatattcga (18)<br>R: gtctctcgagcgccagtttggcggcggcgcgttt (19) | 330 by (20)<br>Co-silencing<br>with HaTub |
| NbDCL4 | F: acatggtaccaagaaaacaattgctgatatagttga (21)<br>R: atccctcgagactgatctcagatcagtcaactg (22) | 395 by (23)<br>Co-silencing<br>with HaTub |
| HaGST1 | F: aatatctagaggcacgaagggcgaatcaca (24)<br>R: gtgtggatcctttgcttcctggtatcccgggg (25) | 641 by (26)<br>GenBank:<br>EF033109 |
| HaAnti-tub | F: ctagtctagaagtgcctccaccgaaggagtggaag (27)<br>R: tcgcggatcccaagcctcttacccggtcgcgctga (28) | 506 by (29) |
| HaHp-tub | Sense fragement:<br>F: acgcggatcccaagcctcttacccggtcgcgctga (30)<br>R: tccggaattcagtgcctccaccgaaggagtggaaga (31) | 506 by (11) |

TABLE 1 -continued

| Gene Primers and Gene Sequences | | |
|---|---|---|
| Gene | Primers: Sequence (5'→3') (SEQ ID NO:) | Cloned Gene (SEQ ID NO:) |
| | Antisense fragement:<br>F: acccaagcttagtgcctccaccgaaggagtggaag (32)<br>R: tccgctcgagcaagcctcttacccggtcgcgctgaa (33) | 506 by (29) |

RNA extraction and cDNA synthesis: 100 mg leaf or CBM tissues was ground in liquid N2 and extracted with Trizol (Invitrogen). Reverse transcription (RT) reactions were performed to get cDNA as described (Qu et al., 2007).

*Agrobacterium* Infiltration:

Synthetic psTRV1, psTRV2 vectors and its derivatives were introduced into *Agrobacterium* strain AGL1 by electroporation. A 3 ml culture was grown for 24 hr at 28° C. in 50 mg/L kanamycin and 25 mg/L rifampicin. On the following day, the culture was inoculated into LB medium containing 50 mg/L kanamycin, 10 mM 2-(N-morpholino) ethanesulfonic acid (MES) and 20 μM acetosyringone and grown overnight in a 28° C. shaker. Agrobacterial cells were collected by centrifugation and resuspended in MMA solution (10 mM MES, 10 mM $MgCl_2$, 200 μM acetosyringone) to a final $OD_{600}$ of 1.5. The agrobacterial suspension was left at room temperature for 3-4 hr without shaking. Before infiltration, *Agrobacterium* culture containing the psTRV1 or psTRV2 vectors was mixed in a 1:1 ratio. Tobacco plants were infiltrated with cultures by syringe infiltration. For syringe infiltration, agrobacterial-inocula were delivered into the underside of three or four youngest fully-expanded leaf using a 1 ml needleless syringe. For cotton vacuum infiltration, whole plants were submerged into agrobacterial-inocula and subjected to 80-90 kPa vacuum for 2 min, and then quickly releasing the vacuum, letting the inoculum rapidly enter plant tissues. After vacuum infiltration, excess agrobacterial cell suspension was used to drench the root system of infiltrated plants. Infiltrated plants were grown in a growth chamber at 25° C. with 16 hr light/8 hr dark photoperiod cycle.

Example 2

Identification of Insect Target Sequence

This example illustrates the identification of nucleotide sequences that, when inserted into the VIGS vector to produce recombinant virus replicating in the host plants, which can be a diet of a cotton bollworm (CBM), are useful for controlling a CBM species insect pest. This example shows that the VIGS system can be used to rapidly screen for genes useful for controlling insects with RNAi technology.

Insect P450 monooxygenases play a central role in adaptation to plant defense compounds and in developing insecticide resistance. Cotton bollworm requires an elevated level of a gossypol-induced cytochrome P450 (HaCYP6AE14) to detoxify gossypol when they grow on cotton, downregulation of HaCYP6AE14 might reduce larval tolerance of gossypol if larvae are fed plant material that expresses VIGS vector against a target of interest.

A CYP6AE14 gene coding sequence derived from GenBank was used to construct a nucleotide sequence encoding in a single strand inserted VIGS vector. A 859 bp coding sequence as set forth in SEQ ID NO:5 encoding a part of a CYP6AE14 sequence was used to construct a primer pair for use in a thermal amplification reaction using CBM cDNA product generated as Example 1. The primer pair as set forth at SEQ ID NO:3 and SEQ ID NO:4 enabled the amplification of a double stranded coding sequence DNA amplicon, one strand of which exhibited the sequence as set forth in SEQ ID NO:5. To amplify the bollworm sense CYP6AE14 gene for functional analysis using VIGS in cotton, SEQ ID NO:3 and SEQ ID NO:4 correspond respectively to forward and reverse genome amplification primers for use in producing a fragment from cotton bollworm cDNA product. DNA fragment sequence as set forth in SEQ ID NO:5 was inserted into psTRV2 in the sense orientation to give psTRV2:HaCYP6AE14. A mixture of *Agrobacterium* cultures containing psTRV1 with psTRV2:JcCurcin (as a non-insect sequence control) or psTRV2:GhDCS (see Example 1 as a positive control) or psTRV2:HaCYP6AE14 vector was vacuum infiltrated into 2-3 true leaf cotton plants.

Figure 3:
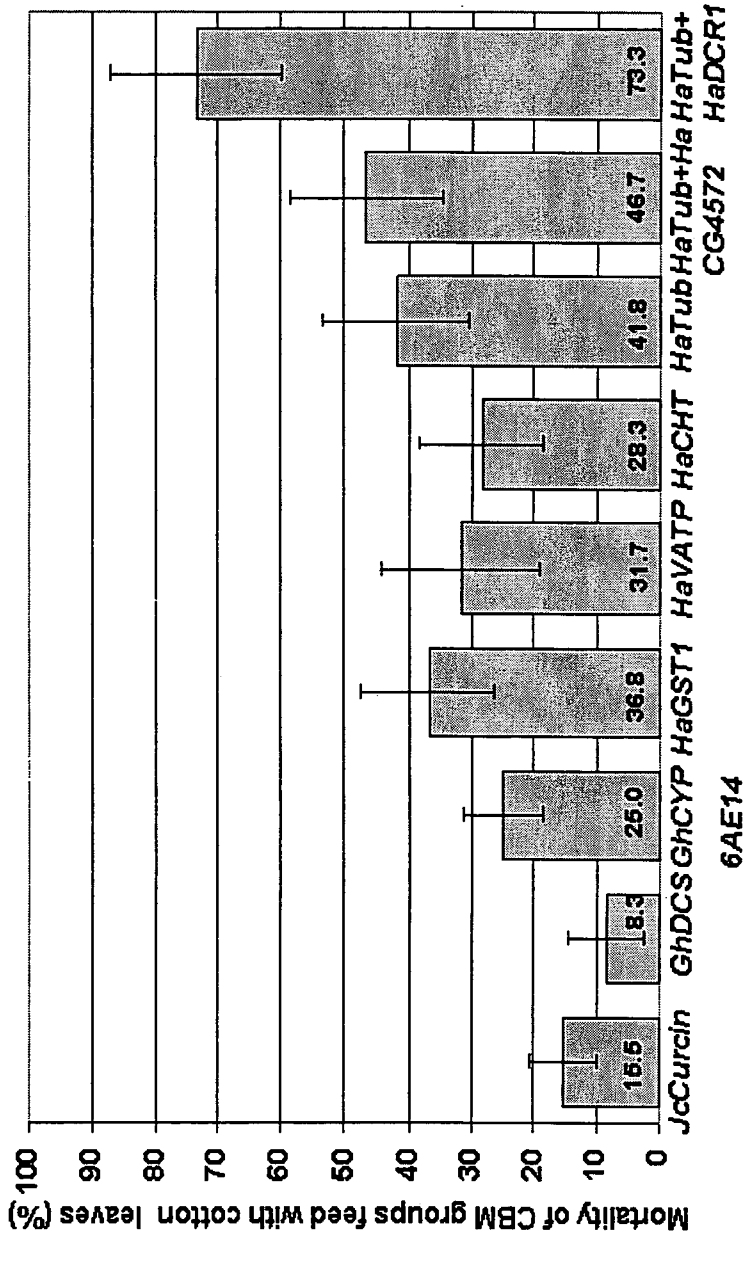
FIG. 3 shows sTRV-mediated silencing of cotton bollworm (CBM) genes and control of insect infestation on cotton. Numbers represent mean relative values average mortality after 13 day-feeding with systemic leaves of plants treated with various sTRV vectors from at least 3 independent experiments with standard error. For each feeding experiment, synchronous larvae (2-3 instar) were selected, weighed individually and divided into groups; each group contained 6-18 individuals.

After 14 days post inoculation, new systemic leaves of *agrobacterium* treated cotton plants were used to feed to CBM larvae. A significant higher larval mortality at 13 days-feeding with ($p<0.05$) was observed for larvae group feeding on leaves of cotton plants infected with sTRV:HaCYP6AE14 whose include a sense HaCYP6AE14 gene sequences as set forth in SEQ ID NO:5 compared to the non-insect sequence control (JcCurcin) (FIG. 3). In contrast with HaCYP6AE14 inhibitory role on larval mortality, a significant reduction ($p<0.05$) of larval mortality at same period was observed for larvae group feeding on leaves of cotton plants infected with sTRV:GhDCS whose include a cotton δ-cadinene synthase gene (DCS), an enzyme important for biosynthesis of insect inhibitory toxic phytochemicals gossypol. Much lower gossypol content were detected with High-performance liquid chromatography in cotton leaves infected with sTRV:GhDCS (cotton VIGS patent). Lower gossypol content leads to higher survival rate compared with JcCurcin control.

These results indicated that the synthetic sTRV-VIGS systems could be used to induce silencing of desirable endogenous insect genes to inhibit insect infestation. Because HaCYP6AE14 only leads to weak inhibitory effect on CBM larvae growth, additional screening is performed to find other useful genes which silencing can lead to a higher inhibitory effect and can be used to generate transgenic plants for biotechnological application in controlling insects.

Example 3

Identification of Insect Target Sequence

This example illustrates the identification of nucleotide sequences that, when inserted into the VIGS vector produces recombinant virus replicating in the host plants, which can be a diet of a cotton bollworm, are useful for controlling a cotton bollworm species insect pest.

Bio-energy metabolism pathway of eukaryotic systems is a basal and essential function for living organism. The vacuolar $H^+$-ATPase (V-ATPase) is one of the most fundamental enzymes in nature. It functions in maintaining sufficient levels of ATP in almost every eukaryotic cell and energizes a wide variety of organelles and membranes. Null mutations in genes encoding V-ATPase subunits are likely to be lethal for most eukaryotic cells because primary energization of the vacuolar system by this enzyme drives vital secondary transport processes across membranes of vacuolar-derived organelles. Disruption of genes encoding V-ATPase subunits in *Drosophila* is also lethal. Therefore, V-ATPase may be a useful target for VIGS mediated inhibition of insect.

V-ATPase is consisting of several subunits. Subunit A, the 68-kDa subunit A binds ATP and catalyzes its hydrolysis. In order to study the inhibition role of VATPase gene in insect growth, we first cloned putative V-ATPase subunit A cotton bollworm gene homologue. We used the amino acid sequence of known tobacco hornworm (*Manduca sexta*, GenBank accession Number: P31400) subunit A to search the GenBank cotton bollworm (*Helicoverpa armigera*) EST database using TBLASTN. Cotton bollworm EST sequences BUO38734 and EE399876 showed significant homology to hornworm V-ATPase catalytic subunit A. Based on this information, we got a contig with 896 bp encoded C terminal domain cotton bollworm V-ATPase subunit A protein. The nucleotide sequence of putative cotton bollworm VATP-A gene was listed as SEQ ID NO:34. The nucleotide sequence analysis of HaVATP-A gene show 89.4% identity in coding region. Amino acid sequence analysis of cotton bollworm V-ATPase subunit A shows 86.3% identity and 93.9% similarity to hornworm VATPase subunit A gene.

A VATP-A gene coding sequence was used to construct a nucleotide sequence encoding HaVATP-A in a single strand inserted VIGS vector. A 763 bp coding sequence as set forth in SEQ ID NO:8 encoding a part of a VATP-A sequence was used to construct a primer pair for use in a thermal amplification reaction using CBM cDNA product generated as in Example 1. The primer pair as set forth at SEQ ID NO:6 and SEQ ID NO:7 enabled the amplification of a double stranded coding sequence DNA amplicon, one strand of which exhibited the sequence as set forth in SEQ ID NO:8. To amplify the bollworm sense VATP-A gene for functional analysis using VIGS in cotton and tobacco, SEQ ID NO:6 and SEQ ID NO:7 correspond respectively to forward and reverse genome amplification primers for use in producing a fragment from cotton bollworm cDNA product. DNA fragment sequence as set forth in SEQ ID NO:8 was inserted into psTRV2 in the sense orientation to give psTRV2:HaVATP. A mixture of *Agrobacterium* cultures containing psTRV1 with psTRV2:JcCurcin (as a non-insect sequence control) or psTRV2:GhDCS (see Example 1 as a positive control) or psTRV2:HaVATP vector was vacuum infiltrated into 2-3 true leaf cotton plants or 5-6 true leaf tobacco plants.

Figure 4:
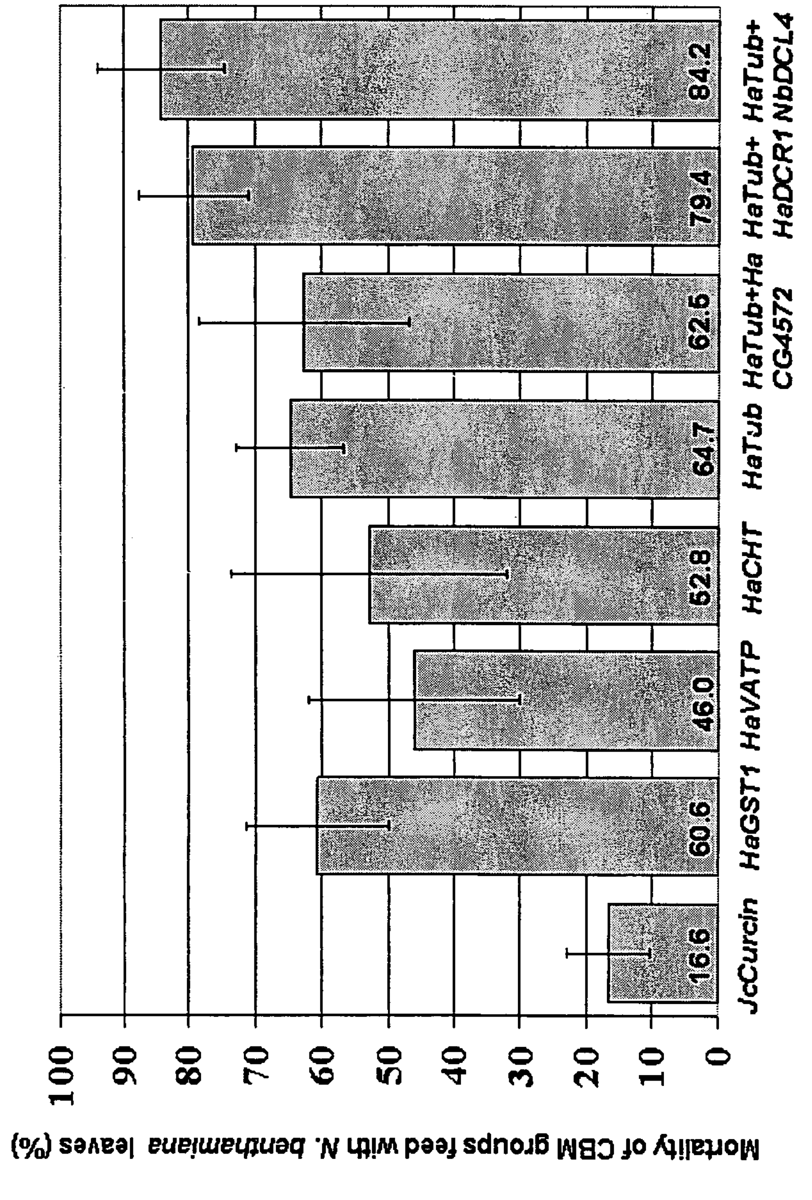
FIG. 4 shows sTRV-mediated silencing of CBM genes and control of insect infestation on *N. benthamiana*. Numbers represent mean relative values average mortality after 13 day-feeding with systemic leaves of plants treated with various sTRV vectors from at least 3 independent experiments with standard error. For each feeding experiment, synchronous larvae (2-3 instar) were selected, weighed individually and divided into groups; each group contained 6-18 individuals.

After 14 days post inoculation, new systemic leaves of *agrobacterium* treated cotton plants were used to feed to CBM larvae. For tobacco plants, after 7-10 days post inoculation, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:HaVATP whose include a sense HaVATP gene sequences as set forth in SEQ ID NO:8 compared to the non-insect sequence control (JcCurcin) (FIG. 3 and FIG. 4). Better insect inhibitory effect has been observed in HaVATP cotton treated group than that of HaCYP6AE14.

These results indicated that the synthetic sTRV-VIGS systems could be used to rapidly screen for desirable endogenous insect genes whose silencing can inhibit insect infestation both in cotton and tobacco. These results showed that the VIGS systems may also use in other important crops like Brome mosaic virus in rice and Barley Stripe Mosaic Virus in wheat for screening genes for RNAi controlling insect infestation.

Example 4

Identification of Insect Target Sequence

This example illustrates the identification of nucleotide sequences that, when inserted into the VIGS vector produces recombinant virus replicating in the host plants, which can be a diet of a cotton bollworm, are useful for controlling a cotton bollworm species insect pest.

Chitin is a β(1→4) homopolymer of N-acetylglucosamine and composes the insect exoskeletons. In insect, chitin supports the cuticles of the epidermis and trachea as well as the peritrophic matrices lining the gut epithelium. Insect growth and morphogenesis are strictly dependent on the capability to remodel chitin-containing structures. Chitin must also be degraded to some extent to mediate the steps involved in the insect molting process. Chitinases are digestive enzymes that break down glycosidic bonds in chitin. Therefore, suppression of chitinase protein formation may be a useful target for VIGS mediated inhibition of insect.

On the other hand, genes and cDNAs encoding insect chitinases have been identified and characterized from several lepidopteran, dipteran, and coleopteran insects. Even though only one (or occasionally two) chitinase gene had been previously identified in studies involving many insect species, database searches of fully sequenced genomes from *Drosophila, Anopheles*, and, more recently, *Tribolium*, have revealed that each of these insects has a rather large family of genes encoding chitinase and chitinase-like proteins with 16-23 members, depending on the species. With our rapid VIGS system in insect, we can quickly evaluate them and identify the gene's function individually. In order to study the inhibitory role of chitinase gene silencing in insect growth, we cloned one chitinase gene homologue. We searched in GenBank and found at least 5 chitinase genes in the bollworm genome. We chose one chitinase gene (GenBank accession number: AY325496) as an example. This chitin gene full length cDNA sequence set forth in SEQ ID NO:35.

A chitin gene coding sequence was used to construct a nucleotide sequence encoding in a single strand inserted VIGS vector. A 693 bp coding sequence as set forth in SEQ ID NO:17 encoding a part of a chitin sequence was used to construct a primer pair for use in a thermal amplification reaction using CBM cDNA product generated as in Example 1. The primer pair as set forth at SEQ ID NO:15 and SEQ ID NO:16 enabled the amplification of a double stranded coding sequence DNA amplicon, one strand of which exhibited the sequence as set forth in SEQ ID NO:17. To amplify the bollworm sense CHT gene for functional analysis using VIGS in cotton, SEQ ID NO:15 and SEQ ID NO:16 correspond respectively to forward and reverse genome amplification primers for use in producing a fragment from cotton bollworm cDNA product. DNA fragment sequence as set forth in SEQ ID NO:17 was inserted into psTRV2 in the sense orientation to give psTRV2:HaCHT. A mixture of *Agrobacterium* cultures containing psTRV1 with psTRV2: JcCurcin (as a non-insect sequence control) or psTRV2: GhDCS (see Example 1 as a positive control) or psTRV2: HaCHT1 vector was vacuum infiltrated into 2-3 true leaf cotton plants or 5-6 true leaf tobacco plants.

After 14 days post inoculation, new systemic leaves of *agrobacterium* treated cotton plants were used to feed to CBM larvae. For tobacco plants, after 7-10 days post inoculation, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:HaCHT whose include a sense HaCHT gene sequences as set forth in SEQ ID NO:17 compared to the non-insect sequence control (JcCurcin) (FIG. 3 and FIG. 4). Better insect inhibitory effect has been observed in HaCHT tobacco treated group than these of HaCYP6AE14 and HaVATP, while a slightly weaker inhibitory effect than that of HaVATP was also found in cotton.

Example 5

Identification of Insect Target Sequence

This example illustrates the identification of nucleotide sequences that, when inserted into the VIGS vector produces recombinant virus replicating in the host plants, which can be a diet of a cotton bollworm, are useful for controlling a cotton bollworm species insect pest.

A glutathione-S-transferase GSTs catalyse the conjugation of reduced glutathione via a sulthydryl group to electrophilic centers on a wide variety of substrates. This detoxin activity may function as a transport protein to detoxify endogenous toxin to help insect survival in the living environment filled with phytoalexin. Therefore, suppression of this protein formation may be a useful target for VIGS mediated inhibition. We chose one GST1 gene (GenBank accession number: EF033109) as an example. This GST1 gene full length cDNA sequence set forth in SEQ ID NO:36.

A GST1 gene coding sequence was used to construct a nucleotide sequence encoding in a single strand inserted VIGS vector. A 641 bp coding sequence as set forth in SEQ ID NO:26 encoding a part of a GST1 sequence was used to construct a primer pair for use in a thermal amplification reaction using CBM cDNA product generated as in Example 1. The primer pair as set forth at SEQ ID NO:24 and SEQ ID NO:25 enabled the amplification of a double stranded coding sequence DNA amplicon, one strand of which exhibited the sequence as set forth in SEQ ID NO:26. To amplify the bollworm sense GST1 gene for functional analysis using VIGS in cotton, SEQ ID NO:24 and SEQ ID NO:25 correspond respectively to forward and reverse genome amplification primers for use in producing a fragment from cotton bollworm cDNA product. DNA fragment sequence as set forth in SEQ ID NO:26 was inserted into psTRV2 in the sense orientation to give psTRV2:HaGST1. A mixture of *Agrobacterium* cultures containing psTRV1 with psTRV2: JcCurcin (as a non-insect sequence control) or psTRV2: GhDCS (see Example 1 as a positive control) or psTRV2: HaGST1 vector was vacuum infiltrated into 2-3 true leaf cotton plants or 5-6 true leaf tobacco plants.

After 14 days post inoculation, new systemic leaves of *agrobacterium* treated cotton plants were used to feed to CBM larvae. For tobacco plants, after 7-10 days post inoculation, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:HaGST1 whose include a sense HaGST1 gene sequences as set forth in SEQ ID NO:26 compared to the non-insect sequence control (JcCurcin) (FIG. 3 and FIG. 4). Better insect inhibitory effect has been observed in HaGST1 cotton and tobacco treated group than these of HaCYP6AE14, HaVATP and HaCHT.

Example 6

Identification of Insect Target Sequence

This example illustrates the identification of nucleotide sequences that, when inserted into the VIGS vector produces recombinant virus replicating in the host plants, which can be a diet of a cotton bollworm, are useful for controlling a cotton bollworm species insect pest.

The cytoskeleton is a cellular “scaffolding” or “skeleton” contained within the cytoplasm. Tubulin proteins are important structural components of many cellular structures in all eukaryote cells and principally in the formation of microtubules. Inhibition of microtubule formation in cells results in severe phenotypes, such as blocking cell division and the like, leads to stopping growth. Therefore, suppression of tubulin protein formation may be a useful target for VIGS mediated inhibition.

In order to study the inhibition role of tubulin gene in insect growth, we first cloned its alpha-tubulin putative cotton bollworm gene homologue. We used the amino acid sequence of known domestic silkworm *Bombyx mori*) alpha-tubulin (NP_001036884) to search the GenBank cotton bollworm (*Helicoverpa armigera*) EST database using TBLASTN. Cotton bollworm EST clone BU038726 showed significant homology to Bmtub. The nucleotide sequence of putative cotton bollworm Hatub gene was 689 bp and listed as SEQ ID NO:37. The nucleotide sequence anlysis of Hatub gene shows 89.4% identity in the coding region of silkworm Bmtub. Amino acid sequence analysis of cotton bollworm Hatub shows 86.3% identity and 93.9% similarity with Bmtub. The amino acid of putative Hatub gene is set forth in SEQ ID NO:38.

An alpha-tubulin coding sequence was used to construct a nucleotide sequence encoding in a single strand inserted VIGS vector. A 506 bp coding sequence as set forth in SEQ ID NO:11 including a 5' UTR and coding region encoding a partial alpha-tubulin protein was used to construct a primer pair for use in a thermal amplification reaction using CBM cDNA product generated as in Example 1. The primer pair as set forth at SEQ ID NO:9 and SEQ ID NO:10 enabled the amplification of a double stranded sequence DNA amplicon, one strand of which exhibited the sequence as set forth in SEQ ID NO:11. To amplify the bollworm sense tub gene for functional analysis using VIGS in cotton and tobacco, SEQ ID NO:9 and SEQ ID NO:10 correspond respectively to forward and reverse genome amplification primers for use in producing a fragment from cotton bollworm cDNA product. DNA fragment sequence as set forth in SEQ ID NO:11 was inserted into psTRV2 in the sense orientation to give psTRV2:Hatub. A mixture of *Agrobacterium* cultures containing psTRV1 with psTRV2:JcCurcin (as a non-insect sequence control) or psTRV2:GhDCS (see Example 1 as a positive control) or psTRV2:Hatub vector was vacuum infiltrated into 2-3 true leaf cotton plants or 5-6 true leaf tobacco plants.

After 14 days post inoculation, new systemic leaves of *agrobacterium* treated cotton plants were used to feed to CBM larvae. For tobacco plants, after 7-10 days post inoculation, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:Hatub whose include a sense Hatub gene sequences as set forth in SEQ ID NO:11 compared to the non-insect sequence control (JcCurcin) (FIG. 3 and FIG. 4). Better insect inhibitory effect has been observed in Hatub cotton and tobacco treated group than these of HaCYP6AE14, HaVATP, HaCHT and HaGST1.

Example 7

Co-Silencing of Insect Small RNA Pathway Increases the Inhibitory Efficiency This example illustrates the synergistic effects of providing in the diet of an invertebrate pest one or more pesticidally effective genes together with single ss-RNA sequences derived from the invertebrate pest.

As indicated in Example 6, providing feeding with plant materials infected with recombinant VIGS virus results in the inhibition of one or more biological functions in the pest and therefore functions to achieve a pesticidal effect, resulting in the mortality of the pest or some other measurable feature that reduces the ability of the pest to infest a particular environment or host. The addition of one or more other gene, each different from each other and each functioning to achieve its pesticidal effect by a means different from the different pathway in which the RNA functions to achieve its pesticidal effect, may result in achieving an improvement in the level of pest control and would further decrease the likelihood that the pest would develop resistance to any one or more of the pesticidal agents or RNA's when used alone to achieve inhibition of the pest.

Small RNAs (smRNAs) regulate processes as diverse as invertebrate development and differentiation. We tested the ability of the co-silencing of smRNA biosynthesis pathway for increase the inhibitory efficiency.

All RNA-silencing pathways require the genesis of 18- to 26-nt smRNAs from the cleavage of double-stranded RNA (dsRNA) or highly structured regions within single-stranded viral RNAs. MicroRNA is one important kind of smRNAs miRNAs are naturally occurring triggers of the RNAi pathway and play an important role in gene regulation in many organisms. During the biogenesis pathway of miRNA, Dicer-1 (DCR1) or its homologues in diverse organism is responsible for pre-microRNA to process into mature miRNA. When DCR1 or its homolog is mutated or down-regulated or misreguled, severe development defects, such as embryo-lethal and defects in ovule development in plants, and tumor in human being would result. We tested the ability of the VIGS system to co-silence putative DCR1 gene and also explored the possibility of increasing silencing efficiency of a candidate gene by co-silencing of HaDCR1. We used the marker gene Hatub to examine this possibility.

A DCR1 gene coding sequence was used to construct a nucleotide sequence encoding in a single strand inserted into an alpha-tubulin gene VIGS vector for co-silencing. A 330 bp coding sequence as set forth in SEQ ID NO:20 encoding a part of a DCR1 sequence was used to construct a primer pair for use in a thermal amplification reaction using CBM cDNA product generated as in Example 1. The primer pair as set forth at SEQ ID NO:18 and SEQ ID NO:19 enabled the amplification of a double stranded coding sequence DNA amplicon, one strand of which exhibited the sequence as set forth in SEQ ID NO:20. To amplify the bollworm sense HaDCR1 gene for functional analysis using VIGS in cotton and tobacco, SEQ ID NO:18 and SEQ ID NO:19 correspond respectively to forward and reverse genome amplification primers for use in producing a fragment from cotton bollworm cDNA product. DNA fragment sequence as set forth in SEQ ID NO:20 was inserted into psTRV2:Hatub in the sense orientation to give psTRV2:Hatub+HaDCR1. A mixture of *Agrobacterium* cultures containing psTRV1 with psTRV2:JcCurcin (as a non-insect sequence control) or psTRV2:GhDCS (see Example 1 as a positive control) or psTRV2:HaVATP vector or psTRV2:Hatub or psTRV2:Hatub+HaDCR1 was vacuum infiltrated into 2-3 true leaf cotton plants or 5-6 true leaf tobacco plants.

After 14 days post inoculation, new systemic leaves of *agrobacterium* treated cotton plants were used to feed to CBM larvae. For tobacco plants, after 7-10 days post inoculation, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:Hatub+HaDCR1 whose includes a sense HaDCR1 gene sequences as set forth in SEQ ID NO:20 plus a sense Hatub gene sequences as set forth in SEQ ID NO:11 compared to the sTRV:Hatub includes a sense Hatub gene sequences as set forth in SEQ ID NO:11 only (FIG. 3 and FIG. 4). The mortality rate with addition of the HaDCR1 was up to 79.4% from 64.7% of Hatub only. Beside that, mortality speed of Hatub+HaDCR1 is 2-3 days early than that of Hatub only.

These results indicate that co-silencing of two insect different pathway gene can increase the silencing efficiency at least in the case of co-silencing small RNA pathway gene DCR1. This new strategy may useful for more effective insect controlling.

Example 8

Co-Silencing of Plant Viral Resistance System Increases the Inhibitory Efficiency This example illustrates the synergistic effects of providing in the diet of an invertebrate pest one or more pesticidally effective genes RNA sequences derived from the invertebrate pest together with silencing of plant host gene.

As indicated in Example 2 to Example 7 feeding with plant materials infected with recombinant VIGS virus results in the inhibition of one or more biological functions in the pest and therefore functions to achieve a pesticidal effect, resulting in the mortality of the pest or some other measurable feature that reduces the ability of the pest to infest a particular environment or host. The addition of one or more other gene of host plant, involving in plant virus replication, insect infestation process, plant-resistance signal transduction pathway (jasmonic acid, salicylic acid), other physic resistance to insect, and so on, each different from each other and each functioning to achieve its pesticidal effect by a means different from the different pathway in which the RNA functions to achieve its pesticidal effect, may result in achieving an improvement in the level of pest control and would further decrease the likelihood that the pest would develop resistance to any one or more of the pesticidal agents or RNA's when used alone to achieve inhibition of the pest.

RNA silencing is one of the natural plant defense mechanisms against virus infection. We hypothesized that the co-silencing of the host viral resistance system using VIGS should result in more efficient VIGS in insect.

A current model for antiviral silencing in higher plants, using *Arabidopsis thaliana* as an example, suggests that dsRNA replication intermediates of viral genomic RNAs or highly structured regions within single-stranded viral RNAs are first cleaved by RNase III-type Dicer-like 4 (DCL4) or alternatively by DCL2 to produce 21- or 22-nucleotide (nt) small interfering RNAs (siRNAs) (Baulcombe, 2004). This model implies that DCL4 is an important *Arabidopsis* viral resistance gene (Deleris et al., 2006). We tested the ability of the TRV-VIGS system to silence DCL4 and also explored the possibility of increasing silencing efficiency of a candidate gene by co-silencing of DCL4, an important gene dsRNA metabolism. We used the marker gene Hatub to examine this possibility.

First, we have shown that infection with TRV:Hatub alone can result in inhibitory controlling role on *H. armigera*. Next, we investigated whether the silencing efficiency can be increased by co-silencing of tobacco DCL4.

In order to study the effect of co-silncing of tobacco DCL4 gene in insect growth, we first cloned the putative *N. benthamiana* DCL4 homologue. We used the amino acid sequence of known *Arabidopsis thaliana* DCL4 (AtDCL4) gene (At5g20320) to search the GenBank EST database limited in Solanaceae using TBLASTN. Two EST, one tomato EST (GenBank Accession number BF051638) and one common tobacco EST (GenBank Accession number AM846087), encode protein sequences containing conseved ribonuclease III domain. PCR primers for *N. benthamiana* DCL4 gene cloning were designed to target the conserved region between these two EST sequences. PCR products were cloned by pGEM-T-easy vector (Promega, U.S.A) and were further sequenced. A 395 bp coding sequence as set forth in SEQ ID NO:23 encoding a part of a NbDCL4 sequence was used to construct a primer pair for use in a thermal amplification reaction using *N. benthamiana* cDNA product generated as Example 1. The primer pair as set forth at SEQ ID NO:21 and SEQ ID NO:22 enabled the amplification of a double stranded coding sequence DNA amplicon, one strand of which exhibited the sequence as set forth in SEQ ID NO:39. We used SEQ ID NO:23 sequence to further find another EST sequence (GenBank Accession number: FM986783) from *N. benthamiana* cDNA sequence database. One contig of NbDCL4 is as forth in SEQ ID NO:39. The NbDCL4 gene coding sequence was used to construct a nucleotide sequence encoding in a single strand inserted into an alpha-tubulin gene VIGS vector for co-silencing. DNA fragment sequence as set forth in SEQ ID NO:23 was inserted into psTRV2:Hatub in the sense orientation to give psTRV2:Hatub+NbDCL4 by KpnI and XhoI sites. A mixture of *Agrobacterium* cultures containing psTRV1 with psTRV2:JcCurcin (as a non-insect sequence control) or psTRV2:GhDCS (see Example 1 as a positive control) or psTRV2:HaVATP vector or psTRV2:Hatub or psTRV2:Hatub+NbDCL4 was vacuum infiltrated into 2-3 true leaf cotton plants or 5-6 true leaf tobacco plants.

After 7-10 days post inoculation, new systemic leaves of *agrobacterium* treated *N. benthamiana* plants, new systemic leaves of *agrobacterium* treated plants were used to feed to CBM larvae. A significant higher larval mortality at 13 days-feeding with ($p<0.01$) was observed for larvae group feeding on leaves of cotton plants or tobacco infected with sTRV:Hatub+NbDCL4 whose includes a sense NbDCL4 gene sequences as set forth in SEQ ID NO:23 plus a sense Hatub gene sequences as set forth in SEQ ID NO:11 compared to the sTRV:Hatub includes a sense Hatub gene sequences as set forth in SEQ ID NO:11 only (FIG. 4). The mortality rate with addition of the NbDCL4 was up to 84.2% from 64.7% of Hatub only. Beside that, mortality speed of Hatub+NbDCL4 is 2-3 days earlier than that of Hatub only.

These results indicate that co-silencing of insect and host gene involved in dsRNA metabolism can increase the silencing. This new strategy may useful for more effective insect controlling. This can be explained that more dsRNA accumulated in plants leads to higher mortality after insect feed with these plants.

Taken together the enhancement of VIGS effect on plant with co-silencing of *Jatropha* DCL4 homolog (U.S. Provisional Patent Application No. 61/143,484), co-silencing of plant DCL4 homolog can be a general strategy to enhance VIGS effect either in plant or in insect controlling.

Example 9

The Role of Endocytosis-Mediated dsRNA Uptake in Controlling Insects by VIGS dsRNA is taken up in *Drosophila* S2 cells by an active pathway, involving receptor-mediated endocytosis. This pathway is also involved in the antiviral RNAi response against *Drosophila* C virus and Sindbis virus via a systemic spreading silencing signal that elicits protective RNAi-dependent immunity throughout the organism. To examine whether this pathway in CBM is involved in the RNA-mediated insect controlling also, we selected one gene implicated with dsRNA uptaking and important for RNAi resistance to virus infection: CG4572 by VIGS system used in previous examples.

A CG4572 gene coding sequence was used to construct a nucleotide sequence encoding in a single strand inserted into an alpha-tubulin gene VIGS vector for co-silencing. To amplify the CG4572 homolog from *H. armigera*, we used the amino acid sequence of *Drosophila melanogaster* CG4572 protein sequence as seed sequence to search the GenBank Insecta EST database using TBLASTN. Two ESTs from *Heliconius melpomene* (GE842295.1) and *Heliothis virescens* (EY122719.1) were found by this way and further used to design degenerated PCR primers to target conserved sequence motifs of CG4572 from different species of insect. A 1075 bp coding sequence as set forth in SEQ ID NO:14 encoding a part of a CG4572 gene sequence was used to construct a primer pair for use in a thermal amplification reaction using cotton bollworm cDNA product generated as in Example 1. The primer pair as set forth at SEQ ID NO:12 and SEQ ID NO:13 enabled the amplification of a double stranded coding sequence DNA amplicon, one strand of which exhibited the sequence as set forth in SEQ ID NO:14. To amplify the cotton bollworm gene for functional analysis using VIGS in cotton and tobacco, SEQ ID NO:12 and SEQ ID NO:13 correspond respectively to forward and reverse genome amplification primers for use in producing a fragment from cotton bollworm cDNA product. DNA fragment sequence as set forth in SEQ. ID NO:14 was inserted into psTRV2:Hatub in the sense orientation to give psTRV2:Hatub+HaCG4572. A mixture of *Agrobacterium* cultures containing psTRV1 with psTRV2:JcCurcin (as a non-insect sequence control) or psTRV2:GhDCS (see Example 1 as a positive control) or psTRV2:HaVATP vector or psTRV2:Hatub or psTRV2:Hatub+HaCG4572 was vacuum infiltrated into 2-3 true leaf cotton plants or 5-6 true leaf tobacco plants.

After 7-10 days post inoculation, new systemic leaves of *agrobacterium* treated *N. benthamiana* plants were used to feed to CBM larvae. No significant higher larval mortality at 13 days-feeding with ($p<0.01$) was observed for larvae group feeding on leaves of cotton or tobacco infected with sTRV:Hatub+HaCG4572 which includes a sense HaCG4572 gene sequences as set forth in SEQ ID NO:14 plus a sense Hatub gene sequences as set forth in SEQ ID NO: 11 compared to the sTRV:Hatub that includes a sense Hatub gene sequences as set forth in SEQ ID NO:11 only (FIG. 3 and FIG. 4).

It is important to mention that although it is critical to determine the potential to kill larvae by simply monitoring the mortality rate of each treated groups, it may be preferred to check whether the expression of the HaCG4572 in CBM was downregulated when feed with sTRV2:HaCG4572 plants by Northern blot or quantitative PCR.

Example 10

Viral-Expressed Antisense RNA is Inhibitory to Insects

This example illustrates the inhibitory effect of viral-expressed antisense RNA in the diet, of an invertebrate pest.

An antisense alpha-tubulin gene sequence was used to construct a nucleotide sequence encoding in a single strand inserted VIGS vector. A 506 bp sequence as set forth in SEQ ID NO:29 encoding a partial alpha-tubulin protein was used to construct a primer pair (SEQ ID NO:27 and SEQ ID NO:28) for use in a thermal amplification reaction using psTRV2:Hatub plasmid generated as in Example 1. The antisense Hatub expression viral vector was constructed as introduced as in Example 1. An antisense Hatub gene was used to construct a nucleotide sequence encoding in an antisense orientation single strand inserted into the psTRV2001 to form the psTRV2:anti-Hatub. A mixture of *Agrobacterium* cultures containing psTRV1 with psTRV2:JcCurcin (as a non-insect sequence control) or psTRV2:GhDCS (see Example 1 as a positive control) or psTRV2:Hatub vector or psTRV2:Hatub or psTRV2:anti:Hatub was vacuum infiltrated into 2-3 true leaf cotton plants or 5-6 true leaf tobacco plants.

Example 11

Viral-Expressed Hairpin RNA is Inhibitory to Insects

This example illustrates that not only single strand sense insect RNA, but also antisense insect RNA and hairpin structure dsRNA can be made as a recombinant virus which can replicate in the host plants, can be diet of an insect pest and are useful for controlling an insect pest.

Single sense strand DNA fragment sequence as set forth in SEQ ID NO:11 was inserted into psTRV2 to give psTRV2:Hatub as described in Example 6.

A similar strategy as used for the sense tubulin sequence was used to amplify the antisense tubulin sequence from CBM. The bollworm antisense tub gene for functional analysis using VIGS in cotton and tobacco was amplified from cotton bollworm cDNA using the primer pair as set forth at SEQ ID NO:27 and SEQ ID NO:28 which correspond respectively to forward and reverse genome amplification primers. The amplified DNA fragment sequence as set forth in SEQ ID NO:29 was used for producing an antisense Hatub silencing vector psTRV2:Antisense-Hatub (psTRV2:anti:Hatub) as described in Example 10.

A hairpin alpha-tubulin gene sequence was used to construct a nucleotide sequence encoding in a hairpin structure containing VIGS vector. Sense fragment was amplified by PCR with PCR primers set forth as SEQ ID NO:30 and SEQ ID NO:31 and further cloned into the BamHI and EcoRI sites of pSK-intron (Guo et al., 2003), followed insertion of the antisense fragment amplified with PCR primers set forth as SEQ ID NO:32 and SEQ ID NO:33. The Hairpin-Hatub (hpHatub) hairpin structure was subcloned into the BamHI and XhoI sites of psTRV2001 to give psTRV:Hairpin-Hatub (psTRV:hpHatub).

A mixture of *Agrobacterium* cultures containing psTRV1 with psTRV2:JcCurcin (as a non-insect sequence control) or psTRV2:Hatub or psTRV2:Antisensei-Hatub or psTRV2:Hairpin-Hatub was vacuum infiltrated into 2-3 true leaf cotton plants or 5-6 true leaf tobacco (*N. benthamiana*) plants.

Figure 5:
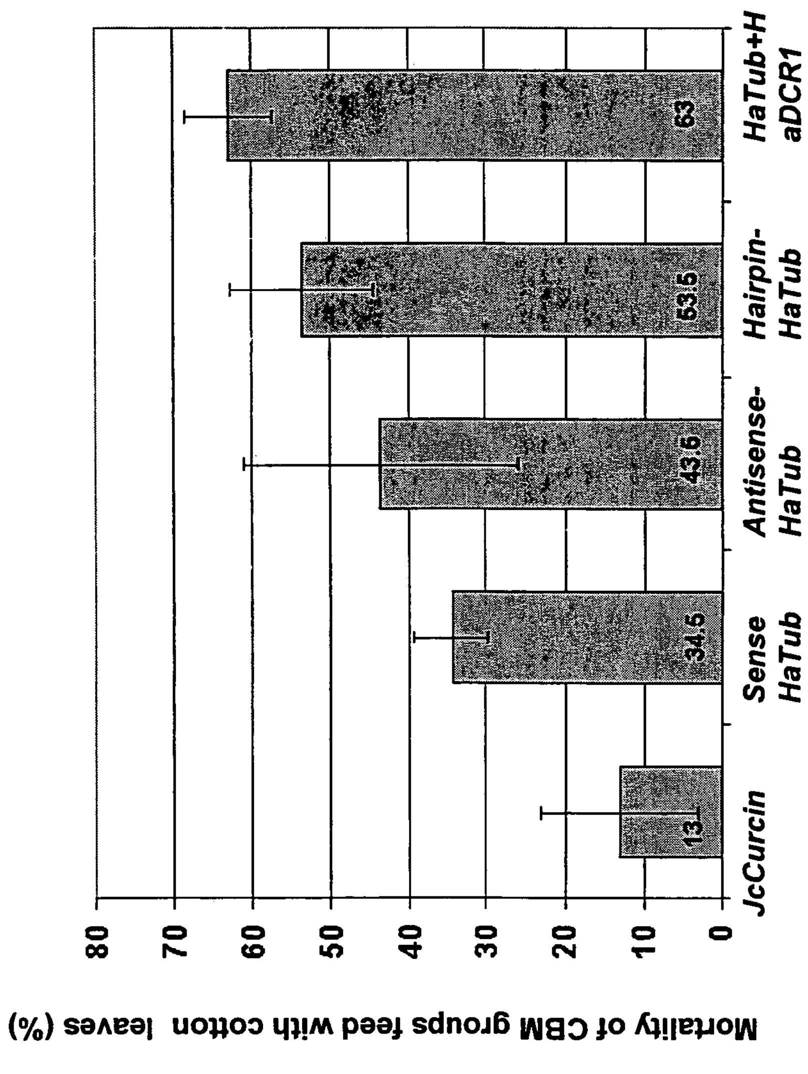
FIG. 5 shows sTRV-mediated silencing of CBM genes and control of insect infestation by sense, antisense and hairpin RNA structure on cotton. Numbers represent mean relative values average mortality after 13 day-feeding with systemic leaves of plants treated with various sTRV vectors.
Figure 6:
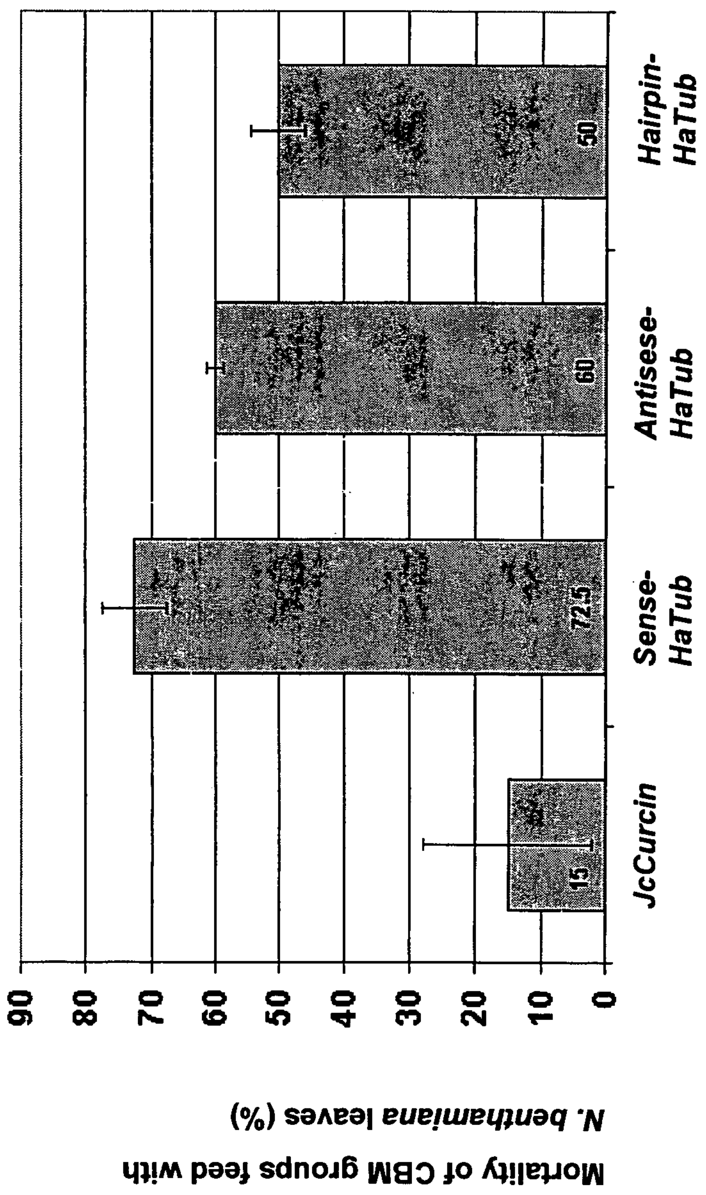
FIG. 6 shows sTRV-mediated silencing of CBM genes and control of insect infestation by sense, antisense and hairpin RNA structure on *N. benthamiana*. Numbers represent mean relative values average mortality after 13 day-feeding with systemic leaves of plants treated with various sTRV vectors.

After 14 days post inoculation, new systemic leaves of *agrobacterium* treated cotton or *N. benthamiana* plants were used to feed to CBM larvae. A significant higher larval mortality at 13 days-feeding with ($p<0.05$) was observed for larvae group feeding on leaves of cotton plants infected with sTRV:Hatub or sTRV:Antisense-Hatub or sTRV:Hairpin-Hatub compared to the non-insect sequence control (JcCurcin) (cotton shown in FIG. 5 and *N. benthamiana* shown in FIG. 6).

These results indicate that the synthetic sTRV-VIGS systems could be used to induce silencing of desirable endogenous insect genes to inhibit insect infestation by insertion of sense, antisense and hairpin structure of an insect gene.

Example 12

Conserved Insect Target Genes

This example lists target genes, sharing conservation with cDNA sequences identified by this invention, in other Insecta order organisms.

Using the method we developed in this invention, we have identified 6 insect genes that can lead to mortality when silenced by recombinant viral vector expression in cotton and tobacco plants. These cDNA sequences can be used to find potential RNAi target genes in other Insecta order organisms, especially these pests for important crops and they were those that encoded V-ATPase A subunit, alpha-tubulin, chitin, GST and DCR1 proteins, the nucleotide sequences of which are as set forth in SEQ ID NOs:8, 11, 17, 26 and 20, respectively. The homologs were defined as the most significant matches to the 6 CBM sequences, as indicated by the best expectation value of NCBI Blast searches. The CBM cDNA sequences were then matched to the sequence database containing all public cDNAs of various organisms in Insecta order from GenBank. The top 100 matches and alignments were kept. The resulting cDNA clones were further chosed as at least one cDNA contain a 21-mer consecutively perfect match with the CBM cDNA sequences.

Using the 6 CBM cDNA sequences, 30 matches were identified with a minimum of 21-mer perfect match region, from 21 distinct organisms, including several pest species, such as Asiatic Rice Borer (*Chilo suppressalis*). The results are listed in Table 2 below with coordinates of match on the query sequence and the hit, percent identity of the match, and the insect species from which the hit sequence was derived. For example, a segment from nucleotide sequence with SEQ ID NO:11 of gene named Hatub was identified to be 97% identical to a segment from a GenBank sequence with the accession number EY118187 from tobacco budworm (*Heliothis virescens*).

TABLE 2

Homologs of Cotton Bollworm Genes

| SEQ ID NO: Gene name | Genus species of hit genes | Gene Accession Number | % Identity |
|---|---|---|---|
| Seq ID NO11 Hatub, | *Heliothis virescens* | EY118187 | 97 |
| Seq ID NO: 11 Hatub, | *Agrotis ipsilon* | EU100018 | 94.9 |
| Seq ID NO: 11 Hatub, | *Spodoptera frugiperda* | DY896617 | 94.6 |
| Seq ID NO: 11 Hatub, | *Xestia c-nigrum* | EU100014 | 94.4 |
| Seq ID NO: 11 Hatub, | *Mythimna separata* | EU100016 | 94.3 |
| Seq ID NO: 11 Hatub, | *Spodoptera exigua* | EU10017 | 93.3 |
| Seq ID NO: 11 Hatub, | *Trichoplusia ni* | FF369778 | 92.3 |
| Seq ID NO: 11 Hatub, | *Danaus plexippus* | EY262486 | 88.8 |
| Seq ID NO: 11 Hatub, | *Ostrinia nubilalis* | GH994602 | 88.2 |
| Seq ID NO: 11 Hatub, | *Heliconius erato* | EL599100 | 88.0 |
| Seq ID NO: 11 Hatub, | *Heliconius melpomene* | EF207983 | 86.6 |
| Seq ID NO: 11 Hatub, | *Culex quinquefasciatus* | XM_001867913 | 85.3 |
| Seq ID NO: 11 Hatub, | *Aedes aegypti* | XM_001652094 | 78.8 |
| Seq ID NO: 11 Hatub, | *Tribolium castaneum* | XM_961399 | 78.6 |
| Seq ID NO: 11 Hatub, | *Acyrthosiphon pisum* | XR_045883 | 78.5 |
| Seq ID NO: 8 HaVATP | *Trichoplusia ni* | CF259336 | 90.1 |
| Seq ID NO: 8 HaVATP | *Bombyx mori* | BY917060 | 90.2 |
| Seq ID NO: 8 HaVATP | *Spodoptera frugiperda* | DV076251 | 90.4 |
| Seq ID NO: 8 HaVATP | *Danaus plexippus* | EY264737 | 88.8 |
| Seq ID NO: 8 HaVATP | *Epiphyas postvittana* | EV803951 | 89.4 |
| Seq ID NO: 8 HaVATP | *Drosophila pseudoobscura* | DR155248 | 83.9 |
| Seq ID NO: 8 HaVATP | *Ostrinia nubilalis* | GH997265 | 92.4 |
| Seq ID NO: 8 HaVATP | *Plodia interpunctella* | EB826765 | 89.2 |
| Seq ID NO: 8 HaVATP | *Heliconius erato* | EL599764 | 85.1 |
| Seq ID NO: 5 HaCYP6AE14 | *Heliothis virescens* | EY121794 | 83.5 |
| Seq ID NO: 17 HaCHT1 | *Mythimna separata* | AY508698 | 90.1 |
| Seq ID NO: 17 HaCHT1 | *Mamestra brassicae* | FJ436415 | 89.1 |
| Seq ID NO: 17 HaCHT1 | *Agrotis ipsilon* | EU035316 | 88.2 |
| Seq ID NO: 17 HaCHT1 | *Spodoptera frugiperda* | AY527414 | 86.3 |
| Seq ID NO: 17 HaCHT1 | *Chilo suppressalis* | AY705930 | 83.2 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

BIBLIOGRAPHY

Baulcombe, D. (2004). RNA silencing in plants. Nature 431:356-363.

Baum, J. A. et al. (2007). Control of coleopteran insect pests through RNA interference. *Nat Biotechnol* 25:1322-1326.

Bhattarai, E. E. et al. 92007). The MI-1-mediated pest resistance requires Hsp90 and Sgt1. *Plant Physiol* 144: 312-323.

Brigneti, G. et al. (2004). Virus-induced gene silencing in *Solanum* species. *Plant J* 39:264-272.

Bucher, G. et al. (2002) Parental RNAi in *Tribolium* (Coleoptera). *Curr Biol* 12:R85-86.

Burch-Smith, T. M. et al. (2004). Applications and advantages of virus-induced gene silencing for gene function studies in plants. *Plant J* 39:734-746.

Burch-Smith, T. M. (2006). Efficient virus-induced gene silencing in *Arabidopsis. Plant Physiol* 142:21-27.

Chen, J. C. et al. (2005). Silencing a prohibition alters plant development and senescence. *Plant J* 44:16-24.

Chung, E. et al. (2004). A method of high frequency virus-induced gene silencing in chili pepper (*Capsicum annuum* L. cv. Bukang). *Mol Cells* 17:377-380.

Constantin, G. D. et al. (2008). Virus-induced gene silencing (VIGS) as a reverse genetic tool to study development of symbiotic root nodules. *Mol. Plant Microbe Interact* 21:720-727.

Deleris, A. et al. (2006). Hierarchical action and inhibition of plant Dicer-like proteins in antiviral defense. *Science* 313:68-71.

Dinesh Kumar et al. (2007). Tobacco rattle virus vectors and related compositions and methods. U.S. Pat. No. 7,229, 829 B2.

Ding, X. S. et al. (2006). Characterization of a Brome mosaic virus strain and its use as a vector for gene silencing in monocotyledonous hosts. *Mol Plant Microbe Interact* 19:1229-1239.

Faivre-Rampant, O. et al. (2004). Potato virus X-induced gene silencing in leaves and tubers of potato. *Plant Physiol* 134:1308-1316.

Fu, D. Q. et al. (2005). Virus-induced gene silencing in tomato fruit. *Plant J* 43:299-308.

Fu, D. Q. et al. (2006). Enhancement of virus-induced gene silencing in tomato by low temperature and low humidity. *Mol Cells* 21:153-160.

Golenberg, E. M. et al. (2009). Development of a gene silencing DNA vector derived from a broad host range geminivirus. *Plant Methods* 5:9.

Grønlund, M. et al. (2008). Virus-induced gene silencing in *Medicago truncatula* and *Lathyrus odorata*. *Virus Res* 135:345-349.

Guo, H. S. et al. (2003). A chemical-regulated inducible RNAi system in plants. *Plant J*34:383-392

Hileman, L. C. et al. (2005). Virus-induced gene silencing is an effective tool for assaying gene function in the basal eudicot species *Papaver somniferum* (opium poppy). *Plant J* 44:334-341.

Hiriart, J. B. et al. (2003). Dynamics of the VIGS-mediated chimeric silencing of the *Nicotiana benthamiana* Ch1H gene and of the tobacco mosaic virus vector. *Mol Plant Microbe Interact* 16:99-106.

Holzberg, S. et al. (2002). Barley stripe mosaic virus-induced gene silencing in a monocot plant. *Plant J* 30:315-327.

Huang, C. et al. (2009). Efficient virus-induced gene silencing in plants using a modified geminivirus DNA1 component. *Plant Biotechnol J* 7:254-265.

Igarashi, A. et al. (2009). Apple latent spherical virus vectors for reliable and effective virus-induced gene silencing among a broad range of plants including tobacco, tomato, *Arabidopsis thaliana*, cucurbits, and legumes. *Virology* 386:407-416.

Kim, K. J. et al. (2007). Functional study of *Capsicum* annutun fatty acid desaturase 1 cDNA clone induced by Tobacco mosaic virus via microarray and virus-induced gene silencing. *Biochem Biophys Res Commun* 362:554-561.

Liu, Y. et al. (2002). Virus-induced gene silencing in tomato. *Plant J* 31:777-786.

Liu, Y. et al. (2004). Virus induced gene silencing of a DEFICIENS ortholog in *Nicotiana benthamiana. Plant Mol Biol* 54:701-711.

McGaughey, W. H. (1985). Insect Resistance to the biological insecticide *Bacillus thuringiensis. Science* 229:193-195.

Mao, Y. B. et al. (2007). Silencing a cotton bollworm P450 monooxygenase gene by plant-mediated RNAi impairs larval tolerance of gossypol. *Nat Biotechnol* 25:1307-1313.

Nagamatsu, A. et al. (2007). Functional analysis of soybean genes involved in flavonoid biosynthesis by virus-induced gene silencing. *Plant Biotechnol J* 5:778-790.

Nasir, K. H. et al. (2005). High-throughput in planta expression screening identifies a class II ethylene-responsive element binding factor-like protein that regulates plant cell death and non-host resistance. *Plant J* 43:491-505.

Prins, M. et al. (2008). Strategies for antiviral resistance in transgenic plants. *Mol Plant Pathol* 9: 73-83.

Qu, J. et al. (2007). Artificial microRNA-mediated virus resistance in plants. *J Virol* 81:6690-6699.

Ratcliff, F. et al. (2001). Tobacco rattle virus as a vector for analysis of gene function by silencing. *Plant J* 25:237-245.

Ruiz, M. T. et al. (1998). Initiation and maintenance of virus-induced gene silencing. *Plant Cell* 10:937-946.

Saitoh, H. and Terauchi, R. Virus-induced silencing of FtsH gene in *Nicotiana benthmiana* causes a striking bleached leaf phenotype. *Genes Genet Syst* 77:335-340.

Shi, B. J. et al. (1997). Plasmid vector for cloning infectious cDNAs from plant RNA viruses: high infectivity of cDNA clones of tomato aspermy cucumovirus. *J Gen Virol* 78 (Pt 5):1181-1185.

Unver, T. and Budak, H. (2009). Virus-induced gene silencing, a post transcriptional gene silencing method. *Int'l J Plant Genomics* 2009:Article ID 198680:8 pages.

Valentine, T. et al. (2004). Efficient virus-induced gene silencing in roots using a modified tobacco rattle virus vector. *Plant Physiol* 136:3999-4009.

Wingard, S. A. (1928). Hosts and symptoms of ring spot, a virus disease of plants. *J Agric Res* 37:127-153

Yamagishi, N. and Yoshikawa, N. Virus-induced gene silencing in soybean seeds and the emergence stage of soybean plants with Apple latent spherical virus vectors. *Plant Mol Biol* 71:15-24.

Zhang, C. and Ghabrial, S. A. (2006). Development of Bean pod mottle virus-based vectors for stable protein expression and sequence-specific virus-induced gene silencing in soybean. *Virology* 344:401-411.

The invention claimed is:

1. A method of screening a cotton insect pest gene to determine whether the cotton insect pest gene can lead to mortality of the cotton insect pest when expression of the cotton insect pest gene is silenced in the cotton insect pest, the method comprising:

(a) inserting a first nucleic acid comprising a target sequence of a cotton insect pest gene to be silenced and a second nucleic acid comprising a target sequence of a cotton insect pest Dicer-1 gene to be silenced into a vector of a virus-induced gene silencing (VIGS) system wherein the vector comprises a tobacco rattle virus (TRV) RNA2 sequence to produce a modified vector comprising a modified TRV RNA2 sequence, wherein the cotton insect pest gene is selected from the group consisting of a gene in a metabolic pathway, a gene in an energy metabolism pathway, a gene encoding a detoxification protein, a gene involved in organ or tissue differentiation, a gene involved in development regulation, a gene involved in molting processing and a gene encoding a cytoskeleton protein, wherein the target sequence in the first nucleic acid is 200 to 1200 nucleotides in length and wherein the target sequence of the cotton insect pest Dicer-1 gene is part of the coding sequence set forth in SEQ ID NO:20;

(b) preparing a mixed culture of *Agrobacterium* comprising *Agrobacterium* containing a vector comprising a TRV RNA1 sequence and *Agrobacterium* containing the modified vector comprising the modified TRV RNA2 sequence;

(c) inoculating the cotton plant host with the mixed culture of *Agrobacterium* to produce an infected cotton plant host;

(d) growing the infected cotton plant host under conditions in which the modified vector comprising the modified TRV RNA2 sequence is replicated and systemically spreads in the infected cotton plant host to produce RNA of the cotton insect pest gene which accumulates in tissue of the infected cotton plant host and to produce RNA of the cotton insect pest Dicer-1 gene which accumulates in tissue of the infected cotton host plant;

(e) feeding the infected cotton plant host tissue with the accumulated RNA of the cotton insect pest gene and RNA of the cotton insect pest Dicer-1 gene to cotton insect pests;

(f) feeding infected cotton plant host tissue with accumulated RNA of the cotton insect pest gene to be silenced to cotton insect pests;

(g) feeding infected cotton plant host tissue with accumulated RNA of the cotton insect pest Dicer-1 gene to cotton insect pests:

(h) comparing mortality rate and/or mortality speed of the cotton insect pests of step (e) to mortality rate and/or mortality speed of the cotton insect pests of step (f) and step (g) and (i) selecting the cotton insect pest gene as a cotton insect pest gene that leads to mortality of the cotton insect pest if the mortality rate and/or mortality speed of the cotton insect pests of step (e) is greater than the mortality rate and/or mortality speed of the cotton insect pests of step (f) and step (g), and the difference between the mortality rates and/or mortality speed from the cotton insect pests of step (e) and step (f) is statistically significant as measured by having a p-value of less than 0.01.

2. The method of claim 1, wherein the infected cotton plant host tissue is a new, systemically infected cotton plant leaf.

3. The method of claim 1, wherein the RNA of the cotton insect pest gene and/or the RNA of the cotton insect pest Dicer-1 gene that is produced is dsRNA.

4. The method of claim 3, wherein the dsRNA is an siRNA or modified to form an siRNA.

5. The method of claim 4, wherein the first nucleic acid and/or the second nucleic acid is inserted into the vector as a hairpin structure.

6. The method of claim 1, wherein the RNA of the cotton insect pest gene and/or the RNA of the cotton insect pest Dicer-1 gene that is produced is ssRNA.

7. The method of claim 6, wherein the first nucleic acid and second nucleic acid are independently inserted into the vector in a sense orientation or an antisense orientation.

8. The method of claim 1, wherein each target sequence is independently selected from the group consisting of (a) a part of a 5' UTR of the gene, (b) a part of a 3' UTR of the gene, (c) a part of a coding sequence of the gene, (d) a part of a 5' UTR of the gene and a part of a coding sequence of the gene and (e) a part of a coding sequence of the gene and part of a 3' UTR of the gene.

9. A method of increasing larval mortality in larvae of cotton insect pests by viral expression of target cotton insect pest sequences in a cotton plant host to modify endogenous expression of the cotton insect pest genes in cells or tissues of the cotton insect pest, the method comprising:

(a) inserting a first nucleic acid comprising a target sequence of a cotton insect pest gene to be silenced and a second nucleic acid comprising a target sequence of a cotton insect pest Dicer-1 gene to be silenced into a vector of a virus-induced gene silencing (VIGS) system wherein the vector comprises a tobacco rattle virus (TRV) RNA2 sequence to produce a modified vector comprising a modified TRV RNA2 sequence, wherein the cotton insect pest gene is selected from the group consisting of a gene in a metabolic pathway, a gene in an energy metabolism pathway, a gene encoding a detoxification protein, a gene involved in organ or tissue differentiation, a gene involved in development regulation, a gene involved in molting processing and a gene encoding a cytoskeleton protein, wherein the target sequence in the first nucleic acid is 200 to 1200 nucleotides in length and wherein the target sequence of the cotton insect pest Dicer-1 gene is part of the coding sequence set forth in SEQ ID NO:20;

(b) preparing a mixed culture of *Agrobacterium* comprising *Agrobacterium* containing a vector comprising a TRV RNA1 sequence and *Agrobacterium* containing the modified vector comprising the modified TRV RNA2 sequence;

(c) inoculating cotton plant host with the mixed culture of *Agrobacterium* to produce an infected cotton plant host; and (d) growing the infected cotton plant host under conditions in which the modified vector comprising the modified TRV RNA2 sequence is replicated and systemically spreads in the infected cotton plant host to produce RNA of the cotton insect pest gene which accumulates in tissue of the infected cotton plant host and to produce RNA of the cotton insect pest Dicer-1 gene which accumulates in tissue of the infected cotton host plant;

wherein the target sequence of the first nucleic acid has been shown to silence the cotton insect pest gene;

wherein the accumulated RNA of the cotton insect pest gene and the accumulated RNA of the cotton insect pest Dicer-1 gene causes gene silencing in the cotton insect pest upon ingestion of the RNA produced in the infected cotton plant host.

10. The method of claim 9, wherein the infected cotton plant host tissue is a new, systemically infected cotton plant leaf.

11. The method of claim 9, wherein the RNA of the cotton insect pest gene and/or the RNA of the cotton insect pest Dicer-1 gene that is produced is dsRNA.

12. The method of claim 11, wherein the dsRNA is an siRNA or modified to form an siRNA.

13. The method of claim 12, wherein the first nucleic acid and/or the second nucleic acid is inserted into the vector as a hairpin structure.

14. The method of claim 9, wherein the RNA of the cotton insect pest gene and/or the RNA of the cotton pest Dicer-1 gene that is produced is ssRNA.

15. The method of claim 14, wherein the first nucleic acid and second nucleic acid are independently inserted into the vector in a sense orientation or an antisense orientation.

16. The method of claim 9, wherein the cotton insect pest gene is selected from the group consisting of a gene with the sequence of SEQ ID NO: 5 (CYP6AE14 gene), SEQ ID NO:

8 (VATP-A gene), SEQ ID NO: 29 (DCR1), SEQ ID NO: 35 (chitinase), SEQ ID NO: 36 (GST gene), and SEQ ID NO: 37 (tubulin).

17. The method of claim 9, wherein each target sequence is independently selected from the group consisting of (a) a part of a 5' UTR of the gene, (b) a part of a 3' UTR of the gene, (c) a part of a coding sequence of the gene, (d) a part of a 5' UTR of the gene and a part of a coding sequence of the gene and (e) a part of a coding sequence of the gene and part of a 3' UTR of the gene.

18. The method of claim 1, wherein the cotton insect pest gene is selected from the group consisting of a gene with the sequence of SEQ ID NO: 5 (CYP6AE14 gene), SEQ ID NO: 8 (VATP-A gene), SEQ ID NO: 29 (DCR1), SEQ ID NO: 35 (chitinase), SEQ ID NO: 36 (GST gene), and SEQ ID NO: 37 (tubulin).

19. The method of claim 1, wherein the target sequence in the first nucleic acid is 300 to 1000 nucleotides in length.

20. The method of claim 9, wherein the target sequence in the first nucleic acid is 300 to 1000 nucleotides in length.

21. The method of claim 1, wherein the cotton insect pest is cotton bollworm.

22. The method of claim 9, wherein the cotton insect pest is cotton bollworm.

* * * * *

SEQUENCE LISTING

```
<160> NUMBER OF SEQ ID NOS: 39

<210> SEQ ID NO 1
<211> LENGTH: 17164
<212> TYPE: DNA
<213> ORGANISM: Artificial
<220> FEATURE:
<223> OTHER INFORMATION: sequence of synthetic psTRV1001 vector

<400> SEQUENCE: 1
```

-continued

```
ctcgaatttc cccgatcgtt caaacatttg gcaataaagt ttcttaagat tgaatcctgt     60
tgccggtctt gcgatgatta tcatataatt tctgttgaat tacgttaagc atgtaataat    120
taacatgtaa tgcatgacgt tatttatgag atgggttttt atgattagag tcccgcaatt    180
atacatttaa tacgcgatag aaaacaaaat atagcgcgca aactaggata aattatcgcg    240
cgcggtgtca tctatgttac tagatcggga attcactggc cgtcgtttta caacgtcgtg    300
actgggaaaa ccctggcgtt acccaactta atcgccttgc agcacatccc cctttcgcca    360
gctggcgtaa tagcgaagag gcccgcaccg atcgcccttc ccaacagttg cgcagcctga    420
atggcgcccg ctcctttcgc tttcttccct tcctttctcg ccacgttcgc cggctttccc    480
cgtcaagctc taaatcgggg gctcccttta gggttccgat ttagtgcttt acggcacctc    540
gaccccaaaa aacttgattt gggtgatggt tcacgtagtg ggccatcgcc ctgatagacg    600
gtttttcgcc ctttgacgtt ggagtccacg ttctttaata gtggactctt gttccaaact    660
ggaacaacac tcaaccctat ctcgggctat tcttttgatt tataagggat tttgccgatt    720
tcggaaccac catcaaacag gattttcgcc tgctggggca aaccagcgtg gaccgcttgc    780
tgcaactctc tcagggccag gcggtgaagg gcaatcagct gttgcccgtc tcactggtga    840
aaagaaaaac caccccagta cattaaaaac gtccgcaatg tgttattaag ttgtctaagc    900
gtcaatttgt ttacaccaca atatatcctg ccaccagcca gccaacagct ccccgaccgg    960
cagctcggca caaaatcacc actcgataca ggcagcccat cagtccggga cggcgtcagc   1020
gggagagccg ttgtaaggcg gcagactttg ctcatgttac cgatgctatt cggaagaacg   1080
gcaactaagc tgccgggttt gaaacacgga tgatctcgcg gagggtagca tgttgattgt   1140
aacgatgaca gagcgttgct gcctgtgatc aaatatcatc tccctcgcag agatccgaat   1200
tatcagcctt cttattcatt tctcgcttaa ccgtgacagg ctgtcgatct tgagaactat   1260
gccgacataa taggaaatcg ctggataaag ccgctgagga agctgagtgg cgctatttct   1320
ttagaagtga acgttgacga tatcaactcc cctatccatt gctcaccgaa tggtacaggt   1380
cggggacccg aagttccgac tgtcggcctg atgcatcccc ggctgatcga ccccagatct   1440
ggggctgaga aagcccagta aggaaacaac tgtaggttcg agtcgcgaga tccccccggaa  1500
ccaaaggaag taggttaaac ccgctccgat caggccgagc cacgccaggc cgagaacatt   1560
ggttcctgta ggcatcggga ttggcggatc aaacactaaa gctactggaa cgagcagaag   1620
tcctccggcc gccagttgcc aggcggtaaa ggtgagcaga ggcacgggag gttgccactt   1680
gcgggtcagc acggttccga acgccatgga aaccgccccc gccaggcccg ctgcgacgcc   1740
gacaggatct agcgctgcgt ttggtgtcaa caccaacagc gccacgcccg cagttccgca   1800
aatagccccc aggaccgcca tcaatcgtat cgggctacct agcagagcgg cagagatgaa   1860
cacgaccatc agcggctgca cagcgcctac cgtcgccgcg accccgcccg gcaggcggta   1920
gaccgaaata aacaacaagc tccagaatag cgaaatatta agtgcgccga ggatgaagat   1980
gcgcatccac cagattcccg ttggaatctg tcggacgatc atcacgagca ataaacccgc   2040
cggcaacgcc cgcagcagca taccggcgac ccctcggcct cgctgttcgg gctccacgaa   2100
aacgccggac agatgcgcct tgtgagcgtc cttggggccg tcctcctgtt tgaagaccga   2160
cagcccaatg atctcgccgt cgatgtaggc gccgaatgcc acggcatctc gcaaccgttc   2220
agcgaacgcc tccatgggct ttttctcctc gtgctcgtaa acggacccga acatctctgg   2280
agctttcttc agggccgaca atcggatctc gcggaaatcc tgcacgtcgg ccgctccaag   2340
ccgtcgaatc tgagccttaa tcacaattgt caattttaat cctctgttta tcggcagttc   2400
```

-continued

```
gtagagcgcg ccgtgcgtcc cgagcgatac tgagcgaagc aagtgcgtcg agcagtgccc   2460
gcttgttcct gaaatgccag taaagcgctg gctgctgaac ccccagccgg aactgacccc   2520
acaaggccct agcgtttgca atgcaccagg tcatcattga cccaggcgtg ttccaccagg   2580
ccgctgcctc gcaactcttc gcaggcttcg ccgacctgct cgcgccactt cttcacgcgg   2640
gtggaatccg atccgcacat gaggcggaag gtttccagct tgagcgggta cggctcccgg   2700
tgcgagctga aatagtcgaa catccgtcgg gccgtcggcg acagcttgcg gtacttctcc   2760
catatgaatt tcgtgtagtg gtcgccagca aacagcacga cgatttcctc gtcgatcagg   2820
acctggcaac gggacgtttt cttgccacgg tccaggacgc ggaagcggtg cagcagcgac   2880
accgattcca ggtgcccaac gcggtcggac gtgaagccca tcgccgtcgc ctgtaggcgc   2940
gacaggcatt cctcggcctt cgtgtaatac cggccattga tcgaccagcc caggtcctgg   3000
caaagctcgt agaacgtgaa ggtgatcggc tcgccgatag gggtgcgctt cgcgtactcc   3060
aacacctgct gccacaccag ttcgtcatcg tcggcccgca gctcgacgcc ggtgtaggtg   3120
atcttcacgt ccttgttgac gtggaaaatg accttgtttt gcagcgcctc gcgcgggatt   3180
ttcttgttgc gcgtggtgaa cagggcagag cgggccgtgt cgtttggcat cgctcgcatc   3240
gtgtccggcc acggcgcaat atcgaacaag gaaagctgca tttccttgat ctgctgcttc   3300
gtgtgtttca gcaacgcggc ctgcttggcc tcgctgacct gttttgccag gtcctcgccg   3360
gcggtttttc gcttcttggt cgtcatagtt cctcgcgtgt cgatggtcat cgacttcgcc   3420
aaacctgccg cctcctgttc gagacgacgc gaacgctcca cggcggccga tggcgcgggc   3480
agggcagggg gagccagttg cacgctgtcg cgctcgatct tggccgtagc ttgctggacc   3540
atcgagccga cggactggaa ggtttcgcgg ggcgcacgca tgacggtgcg gcttgcgatg   3600
gtttcggcat cctcggcgga aaaccccgcg tcgatcagtt cttgcctgta tgccttccgg   3660
tcaaacgtcc gattcattca ccctccttgc gggattgccc cgactcacgc cggggcaatg   3720
tgcccttatt cctgatttga cccgcctggt gccttggtgt ccagataatc caccttatcg   3780
gcaatgaagt cggtcccgta gaccgtctgg ccgtccttct cgtacttggt attccgaatc   3840
ttgccctgca cgaataccag cgaccccttg cccaaatact tgccgtgggc ctcggcctga   3900
gagccaaaac acttgatgcg gaagaagtcg gtgcgctcct gcttgtcgcc ggcatcgttg   3960
cgccacatct aggtactaaa acaattcatc cagtaaaata taatatttta ttttctccca   4020
atcaggcttg atccccagta agtcaaaaaa tagctcgaca tactgttctt ccccgatatc   4080
ctccctgatc gaccggacgc agaaggcaat gtcataccac ttgtccgccc tgccgcttct   4140
cccaagatca ataaagccac ttactttgcc atctttcaca aagatgttgc tgtctcccag   4200
gtcgccgtgg gaaaagacaa gttcctcttc gggcttttcc gtctttaaaa aatcatacag   4260
ctcgcgcgga tctttaaatg gagtgtcttc ttcccagttt tcgcaatcca catcggccag   4320
atcgttattc agtaagtaat ccaattcggc taagcggctg tctaagctat tcgtataggg   4380
acaatccgat atgtcgatgg agtgaaagag cctgatgcac tccgcataca gctcgataat   4440
cttttcaggg ctttgttcat cttcatactc ttccgagcaa aggacgccat cggcctcact   4500
catgagcaga ttgctccagc catcatgccg ttcaaagtgc aggacctttg gaacaggcag   4560
ctttccttcc agccatagca tcatgtcctt ttcccgttcc acatcatagg tggtcccttt   4620
ataccggctg tccgtcattt ttaaatatag gttttcattt tctcccacca gcttatatac   4680
cttagcagga gacattcctt ccgtatcttt tacgcagcgg tatttttcga tcagtttttt   4740
```

-continued

```
caattccggt gatattctca ttttagccat ttattatttc cttcctcttt tctacagtat   4800
ttaaagatac cccaagaagc taattataac aagacgaact ccaattcact gttccttgca   4860
ttctaaaacc ttaaatacca gaaaacagct ttttcaaagt tgttttcaaa gttggcgtat   4920
aacatagtat cgacggagcc gattttgaaa ccacaattat gggtgatgct gccaacttac   4980
tgatttagtg tatgatggtg tttttgaggt gctccagtgg cttctgtgtc tatcagctgt   5040
ccctcctgtt cagctactga cggggtggtg cgtaacggca aaagcaccgc cggacatcag   5100
cgctatctct gctctcactg ccgtaaaaca tggcaactgc agttcactta caccgcttct   5160
caacccggta cgcaccagaa aatcattgat atggccatga atggcgttgg atgccgggca   5220
acagcccgca ttatgggcgt tggcctcaac acgattttac gtcacttaaa aaactcaggc   5280
cgcagtcggt aacctcgcgc atacagccgg gcagtgacgt catcgtctgc gcggaaatgg   5340
acgaacagtg gggctatgtc ggggctaaat cgcgccagcg ctggctgttt tacgcgtatg   5400
acagtctccg gaagacggtt gttgcgcacg tattcggtga acgcactatg gcgacgctgg   5460
ggcgtcttat gagcctgctg tcacccttg acgtggtgat atggatgacg gatggctggc   5520
cgctgtatga atcccgcctg aagggaaagc tgcacgtaat cagcaagcga tatacgcagc   5580
gaattgagcg gcataacctg aatctgaggc agcacctggc acggctggga cggaagtcgc   5640
tgtcgttctc aaaatcggtg gagctgcatg acaaagtcat cgggcattat ctgaacataa   5700
aacactatca ataagttgga gtcattaccc aattatgata gaatttacaa gctataaggt   5760
tattgtcctg ggtttcaagc attagtccat gcaagttttt atgctttgcc cattctatag   5820
atatattgat aagcgcgctg cctatgcctt gccccctgaa atccttacat acggcgatat   5880
cttctatata aaagatatat tatcttatca gtattgtcaa tatattcaag gcaatctgcc   5940
tcctcatcct cttcatcctc ttcgtcttgg tagcttttta aatatggcgc ttcatagagt   6000
aattctgtaa aggtccaatt ctcgttttca tacctcggta taatcttacc tatcacctca   6060
aatggttcgc tgggtttatc gcacccccga acacgagcac ggcacccgcg accactatgc   6120
caagaatgcc caaggtaaaa attgccggcc ccgccatgaa gtccgtgaat gccccgacgg   6180
ccgaagtgaa gggcaggccg ccacccaggc cgccgccctc actgcccggc acctggtcgc   6240
tgaatgtcga tgccagcacc tgcggcacgt caatgcttcc gggcgtcgcg ctcgggctga   6300
tcgcccatcc cgttactgcc ccgatcccgg caatggcaag gactgccagc gctgccattt   6360
ttggggtgag gccgttcgcg gccgaggggc gcagcccctg gggggatggg aggcccgcgt   6420
tagcgggccg ggagggttcg agaagggggg gcaccccccct tcggcgtgcg cggtcacgcg   6480
cacagggcgc agccctggtt aaaaacaagg tttataaata ttggtttaaa agcaggttaa   6540
aagacaggtt agcggtggcc gaaaaacggg cggaaaccct tgcaaatgct ggattttctg   6600
cctgtggaca gcccctcaaa tgtcaatagg tgcgcccctc atctgtcagc actctgcccc   6660
tcaagtgtca aggatcgcgc ccctcatctg tcagtagtcg cgcccctcaa gtgtcaatac   6720
cgcagggcac ttatccccag gcttgtccac atcatctgtg ggaaactcgc gtaaaatcag   6780
gcgttttcgc cgatttgcga ggctggccag ctccacgtcg ccggccgaaa tcgagcctgc   6840
ccctcatctg tcaacgccgc gccgggtgag tcggcccctc aagtgtcaac gtccgcccct   6900
catctgtcag tgagggccaa gttttccgcg aggtatccac aacgccggcg gccgcggtgt   6960
ctcgcacacg gcttcgacgg cgtttctggc gcgtttgcag ggccatagac ggccgccagc   7020
ccagcggcga gggcaaccag cccggtgagc gtcgcaaagg cgctcggtct tgccttgctc   7080
gtcggtgatg tacttcacca gctccgcgaa gtcgctcttc ttgatggagc gcatggggac   7140
```

-continued

```
gtgcttggca atcacgcgca ccccccggcc gttttagcgg ctaaaaaagt catggctctg   7200
ccctcgggcg gaccacgccc atcatgacct tgccaagctc gtcctgcttc tcttcgatct   7260
tcgccagcag ggcgaggatc gtggcatcac cgaaccgcgc cgtgcgcggg tcgtcggtga   7320
gccagagttt cagcaggccg cccaggcggc ccaggtcgcc attgatgcgg gccagctcgc   7380
ggacgtgctc atagtccacg acgcccgtga ttttgtagcc ctggccgacg gccagcaggt   7440
aggccgacag gctcatgccg gccgccgccg ccttttcctc aatcgctctt cgttcgtctg   7500
gaaggcagta caccttgata ggtgggctgc ccttcctggt tggcttggtt tcatcagcca   7560
tccgcttgcc ctcatctgtt acgccggcgg tagccggcca gcctcgcaga gcaggattcc   7620
cgttgagcac cgccaggtgc gaataaggga cagtgaagaa ggaacacccg ctcgcgggtg   7680
ggcctacttc acctatcctg cccggctgac gccgttggat acaccaagga aagtctacac   7740
gaaccctttg gcaaaatcct gtatatcgtg cgaaaaagga tggatatacc gaaaaaatcg   7800
ctataatgac cccgaagcag ggttatgcag cggaaaagcg ccacgcttcc cgaagggaga   7860
aaggcggaca ggtatccggt aagcggcagg gtcggaacag gagagcgcac gagggagctt   7920
ccagggggaa acgcctggta tctttatagt cctgtcgggt ttcgccacct ctgacttgag   7980
cgtcgatttt tgtgatgctc gtcagggggg cggagcctat ggaaaaacgc cagcaacgcg   8040
gcctttttac ggttcctggc cttttgctgg ccttttgctc acatgttctt tcctgcgtta   8100
tcccctgatt ctgtggataa ccgtattacc gcctttgagt gagctgatac cgctcgccgc   8160
agccgaacga ccgagcgcag cgagtcagtg agcgaggaag cggaagagcg ccagaaggcc   8220
gccagagagg ccgagcgcgg ccgtgaggct tggacgctag ggcagggcat gaaaaagccc   8280
gtagcgggct gctacgggcg tctgacgcgg tggaaagggg gaggggatgt tgtctacatg   8340
gctctgctgt agtgagtggg ttgcgctccg gcagcggtcc tgatcaatcg tcaccctttc   8400
tcggtccttc aacgttcctg acaacgagcc tccttttcgc caatccatcg acaatcaccg   8460
cgagtccctg ctcgaacgct gcgtccggac cggcttcgtc gaaggcgtct atcgcggccc   8520
gcaacagcgg cgagagcgga gcctgttcaa cggtgccgcc gcgctcgccg gcatcgctgt   8580
cgccggcctg ctcctcaagc acggccccaa cagtgaagta gctgattgtc atcagcgcat   8640
tgacggcgtc cccggccgaa aaacccgcct cgcagaggaa gcgaagctgc gcgtcggccg   8700
tttccatctg cggtgcgccc ggtcgcgtgc cggcatggat gcgcgcgcca tcgcggtagg   8760
cgagcagcgc ctgcctgaag ctgcgggcat tcccgatcag aaatgagcgc cagtcgtcgt   8820
cggctctcgg caccgaatgc gtatgattct ccgccagcat ggcttcggcc agtgcgtcga   8880
gcagcgcccg cttgttcctg aagtgccagt aaagcgccgg ctgctgaacc cccaaccgtt   8940
ccgccagttt gcgtgtcgtc agaccgtcta cgccgacctc gttcaacagg tccagggcgg   9000
cacggatcac tgtattcggc tgcaactttg tcatgcttga cactttatca ctgataaaca   9060
taatatgtcc accaacttat cagtgataaa gaatccgcgc gttcaatcgg accagcggag   9120
gctggtccgg aggccagacg tgaaacccaa catacccctg atcgtaattc tgagcactgt   9180
cgcgctcgac gctgtcggca tcggcctgat tatgccggtg ctgccgggcc tcctgcgcga   9240
tctggttcac tcgaacgacg tcaccgccca ctatggcatt ctgctggcgc tgtatgcgtt   9300
ggtgcaattt gcctgcgcac ctgtgctggg cgcgctgtcg gatcgtttcg ggcggcggcc   9360
aatcttgctc gtctcgctgg ccggcgccag atctggggaa ccctgtggtt ggcatgcaca   9420
tacaaatgga cgaacggata aaccttttca cgccctttta aatatccgat tattctaata   9480
```

-continued

```
aacgctcttt tctcttaggt ttacccgcca atatatcctg tcaaacactg atagtttaaa   9540
ctgaaggcgg gaaacgacaa tctgctagcg gtcaacatgg tggagcacga cactctcgtc   9600
tactccaaga atatcaaaga tacagtctca gaagaccaga gggctattga gacttttcaa   9660
caaagggtaa tatcgggaaa cctcctcgga ttccattgcc cagctatctg tcacttcatc   9720
gaaaggacag tagaaaagga agatggcttc tacaaatgcc atcattgcga taaaggaaag   9780
gctatcgttc aagatgcctc taccgacagt ggtcccaaag atggaccccc acccacgagg   9840
aacatcgtgg aaaaagaaga cgttccaacc acgtcttcaa agcaagtgga ttgatgtgat   9900
ggtcaacatg gtggagcacg acactctcgt ctactccaag aatatcaaag atacagtctc   9960
agaagaccag agggctattg agacttttca acaaagggta atatcgggaa acctcctcgg  10020
attccattgc ccagctatct gtcacttcat cgaaaggaca gtagaaaagg aagatggctt  10080
ctacaaatgc catcattgcg ataaaggaaa ggctatcgtt caagatgcct ctaccgacag  10140
tggtcccaaa gatggacccc cacccacgag gaacatcgtg gaaaaagaag acgttccaac  10200
cacgtcttca aagcaagtgg attgatgtga tatctccact gacgtaaggg atgacgcaca  10260
atcccactat ccttcgcaag acccttcctc tatataagga agttcatttc atttggagag  10320
gataaaacat ttcaatcctt tgaacgcggt agaacgtgct aattggattt tggtgagaac  10380
gcggtagaac gtacttatca cctacagttt tattttgttt ttctttttgg tttaatctat  10440
ccagcttagt accgagtggg ggaaagtgac tggtgtgcct aaaacctttt ctttgatact  10500
ttgtaaaaat acatacagat acaatggcga acggtaactt caagttgtct caattgctca  10560
atgtggacga gatgtctgct gagcagagga gtcatttctt tgacttgatg ctgactaaac  10620
ctgattgtga gatcgggcaa atgatgcaaa gagttgttgt tgataaagtc gatgacatga  10680
ttagagaaag aaagactaaa gatccagtga ttgttcatga agttctttct cagaaggaac  10740
agaacaagtt gatggaaatt tatcctgaat tcaatatcgt gtttaaagac gacaaaaaca  10800
tggttcatgg gtttgcggct gctgagcgaa aactacaagc tttattgctt ttagatagag  10860
ttcctgctct gcaagaggtg gatgacatcg gtggtcaatg gtcgttttgg gtaactagag  10920
gtgagaaaag gattcattcc tgttgtccaa atctagatat tcgggatgat cagagagaaa  10980
tttctcgaca gatatttctt actgctattg gtgatcaagc tagaagtggt aagagacaga  11040
tgtcggagaa tgagctgtgg atgtatgacc aatttcgtga aaatattgct gcgcctaacg  11100
cggttaggtg caataataca tatcagggtt gtacatgtag ggtttttct gatggtaaga  11160
agaaaggcgc gcagtatgcg atagctcttc acagcctgta tgacttcaag ttgaaagact  11220
tgatggctac tatggttgag aagaaaacta aagtggttca tgctgctatg ctttttgctc  11280
ctgaaagtat gttagtggac gaaggtccat taccttctgt tgacggttac tacatgaaga  11340
agaacgggaa gatctatttc ggttttgaga aagatccttc cttttcttac attcatgact  11400
gggaagagta caagaagtat ctactgggga agccagtgag ttaccaaggg aatgtgttct  11460
acttcgaacc gtggcaggtg agaggagaca caatgctttt ttcgatctac aggatagctg  11520
gagttccgag gaggtctcta tcatcgcaag agtactaccg aagaatatat atcagtagat  11580
gggaaaacat ggttgttgtc ccaattttcg atctggtcga atcaacgcga gagttggtca  11640
agaaagacct gtttgtagag aaacaattca tggacaagtg tttggattac atagctaggt  11700
tatctgacca gcagctgacc ataagcaatg ttaaatcata cttgagttca aataattggg  11760
tcttattcat aaacggggcg gccgtgaaga acaagcaaag tgtagattct cgagatttac  11820
agttgttggc tcaaactttg ctagtgaagg aacaagtggc gagacctgtc atgagggagt  11880
```

-continued

```
tgcgtgaagc aattctgact gagacgaaac ctatcacgtc attgactgat gtgctgggtt  11940
taatatcaag aaaactgtgg aagcagtttg ctaacaagat cgcagtcggc ggattcgttg  12000
gcatggttgg tactctaatt ggattctatc caaagaaggt actaacctgg gcgaaggaca  12060
caccaaatgg tccagaacta tgttacgaga actcgcacaa aaccaaggtg atagtatttc  12120
tgagtgttgt gtatgccatt ggaggaatca cgcttatgcg tcgagacatc cgagatggac  12180
tggtgaaaaa actatgtgat atgtttgata tcaaacgggg ggcccatgtc ttagacgttg  12240
agaatccgtg ccgctattat gaaatcaacg atttctttag cagtctgtat tcggcatctg  12300
agtccggtga gaccgtttta ccagatttat ccgaggtaaa agccaagtct gataagctat  12360
tgcagcagaa gaaagaaatc gctgacgagt ttctaagtgc aaaattctct aactattctg  12420
gcagttcggt gagaacttct ccaccatcgg tggtcggttc atctcgaagc ggactgggtc  12480
tgttgttgga agacagtaac gtgctgaccc aagctagagt tggagtttca agaaaggtag  12540
acgatgagga gatcatggag cagtttctga gtggtcttat tgacactgaa gcagaaattg  12600
acgaggttgt tccagccttt tcagctgaat gtgaaagagg ggaaacaagc ggtacaaagg  12660
tgttgtgtaa acctttaacg ccaccaggat ttgagaacgt gttgccagct gtcaaacctt  12720
tggtcagcaa aggaaaaacg gtcaaacgtg tcgattactt ccaagtgatg ggaggtgaga  12780
gattaccaaa aaggccggtt gtcagtggag acgattctgt ggacgctaga agagagtttc  12840
tgtactactt agatgcggag agagtcgctc aaaatgatga aattatgtct ctgtatcgtg  12900
actattcgag aggagttatt cgaactggag gtcagaatta cccgcacgga ctgggagtgt  12960
gggatgtgga gatgaagaac tggtgcatac gtccagtggt cactgaacat gcttatgtgt  13020
tccaaccaga caaacgtatg gatgattggt cgggatactt agaagtggct gtttgggaac  13080
gaggtatgtt ggtcaacgac ttcgcggtcg aaaggatgag tgattatgtc atagtttgcg  13140
atcagacgta tctttgcaat aacaggttga tcttggacaa tttaagtgcc ctggatctag  13200
gaccagttaa ctgttctttt gaattagttg acggtgtacc tggttgtggt aagtcgacaa  13260
tgattgtcaa ctcagctaat ccttgtgtcg atgtggttct ctctactggg agagcagcaa  13320
ccgacgactt gatcgagaga ttcgcgagca aaggttttcc atgcaaattg aaaaggagag  13380
tgaagacggt tgattctttt ttgatgcatt gtgttgatgg ttctttaacc ggagacgtgt  13440
tgcatttcga tgaagctctc atggcccatg ctggtatggt gtacttttgc gctcagatag  13500
ctggtgctaa acgatgtatc tgtcaaggag atcagaatca aatttctttc aagcctaggg  13560
tatctcaagt tgatttgagg ttttctagtc tggtcggaaa gtttgacatt gttacagaaa  13620
aaagagaaac ttacagaagt ccagcagatg tggctgccgt attgaacaag tactatactg  13680
gagatgtcag aacacataac gcgactgcta attcgatgac ggtgaggaag attgtgtcta  13740
aagaacaggt ttctttgaag cctggtgctc agtacataac tttccttcag tctgagaaga  13800
aggagttggt aaatttgttg gcattgagga aagtggcagc taaagtgagt acagtacacg  13860
agtcgcaagg agagacattc aaagatgtag tcctagtcag gacgaaacct acggatgact  13920
caatcgctag aggtcgggag tacttaatcg tggcgttgtc gcgtcacaca caatcacttg  13980
tgtatgaaac tgtgaaagag gacgatgtaa gcaaagagat cagggaaagt gccgcgctta  14040
cgaaggcggc tttggcaaga ttttttgtta ctgagaccgt cttatgacgg tttcggtcta  14100
ggtttgatgt ctttagacat catgaagggc cttgcgccgt tccagattca ggtacgatta  14160
cggacttgga gatgtggtac gacgctttgt ttccgggaaa ttcgttaaga gactcaagcc  14220
```

-continued

```
tagacgggta tttggtggca acgactgatt gcaatttgcg attagacaat gttacgatca  14280
aaagtggaaa ctggaaagac aagtttgctg aaaaagaaac gtttctgaaa ccggttattc  14340
gtactgctat gcctgacaaa aggaagacta ctcagttgga gagtttgtta gcattgcaga  14400
aaaggaacca agcggcaccc gatctacaag aaaatgtgca cgcaacagtt ctaatcgaag  14460
agacgatgaa gaagttgaaa tctgttgtct acgatgtggg aaaaattcgg gctgatccta  14520
ttgtcaatag agctcaaatg gagagatggt ggagaaatca aagcacagcg gtacaggcta  14580
aggtagtagc agatgtgaga gagttacatg aaatagacta ttcgtcttac atgtatatga  14640
tcaaatctga cgtgaaacct aagactgatt taacaccgca atttgaatac tcagctctac  14700
agactgttgt gtatcacgag aagttgatca actcgttgtt cggtccaatt ttcaaagaaa  14760
ttaatgaacg caagttggat gctatgcaac cacattttgt gttcaacacg agaatgacat  14820
cgagtgattt aaacgatcga gtgaagttct taaatacgga agcggcttac gactttgttg  14880
agatagacat gtctaaattc gacaagtcgg caaatcgctt ccatttacaa ctgcagctgg  14940
agatttacag gttatttggg ctagatgagt gggcggcctt cctttgggag gtgtcgcaca  15000
ctcaaactac tgtgagagat attcaaaatg gtatgatggc gcatatttgg taccaacaaa  15060
agagtggaga tgctgatact tataatgcaa attcagatag aacactgtgt gcactcttgt  15120
ctgaattacc attggagaaa gcagtcatgg ttacatatgg aggagatgac tcactgattg  15180
cgtttcctag aggaacgcag tttgttgatc cgtgtccaaa gttggctact aagtggaatt  15240
tcgagtgcaa gatttttaag tacgatgtcc caatgttttg tgggaagttc ttgcttaaga  15300
cgtcatcgtg ttacgagttc gtgccagatc cggtaaaagt tctgacgaag ttggggaaaa  15360
agagtataaa ggatgtgcaa catttagccg agatctacat ctcgctgaat gattccaata  15420
gagctcttgg gaactacatg gtggtatcca aactgtccga gtctgtttca gaccggtatt  15480
tgtacaaagg tgattctgtt catgcgcttt gtgcgctatg gaagcatatt aagagtttta  15540
cagctctgtg tacattattc cgagacgaaa acgataagga attgaacccg gctaaggttg  15600
attggaagaa ggcacagaga gctgtgtcaa acttttacga ctggtaatat ggaagacaag  15660
tcattggtca ccttgaagaa gaagactttc gaagtctcaa aattctcaaa tctaggggcc  15720
attgaattgt ttgtggacgg taggaggaag agaccgaagt attttcacag aagaagagaa  15780
actgtcctaa atcatgttgg tgggaagaag agtgaacaca agttagacgt ttttgaccaa  15840
agggattaca aaatgattaa atcttacgcg tttctaaaga tagtaggtgt acaactagtt  15900
gtaacatcac atctacctgc agatacgcct gggttcattc aaatcgatct gttggattcg  15960
agacttactg agaaaagaaa gagaggaaag actattcaga gattcaaagc tcgagcttgc  16020
gataactgtt cagttgcgca gtacaaggtt gaatacagta tttccacaca ggagaacgta  16080
cttgatgtct ggaaggtggg ttgtatttct gagggcgttc cggtctgtga cggtacatac  16140
cctttcagta tcgaagtgtc gctaatatgg gttgctactg attcgactag gcgcctcaat  16200
gtggaagaac tgaacagttc ggattacatt gaaggcgatt ttaccgatca agaggttttc  16260
ggtgagttca tgtctttgaa acaagtggag atgaagacga ttgaggcgaa gtacgatggt  16320
ccttacagac cagctactac tagacctaag tcattattgt caagtgaaga tgttaagaga  16380
gcgtctaata agaaaaactc gtcttaatgc ataaagaaat ttattgtcaa tatgacgtgt  16440
gtactcaagg gttgtgtgaa tgaagtcact gttcttggtc acgagacgtg tagtatcggt  16500
catgctaaca aattgcgaaa gcaagttgct gacatggttg gtgtcacacg taggtgtgcg  16560
gaaaataatt gtggatggtt tgtctgtgtt gttatcaatg attttacttt tgatgtgtat  16620
```

aattgttgtg gccgtagtca ccttgaaaag tgtcgtaaac gtgttgaaac aagaaatcga 16680
gaaatttgga aacaaattcg acgaaatcaa gctgaaaaca tgtctgcgac agctaaaaag 16740
tctcataatt cgaagacctc taagaagaaa ttcaaagagg acagagaatt tgggacacca 16800
aaaagatttt taagagatga tgttcctttc gggattgatc gtttgtttgc tttttgattt 16860
tattttatat tgttatctgt ttctgtgtat agactgtttg agattggcgc ttggccgact 16920
cattgtctta ccatagggga acggactttg tttgtgttgt tattttattt gtattttatt 16980
aaaattctca atgatctgaa aaggcctcga ggctaagaga ttattggggg gtgagtaagt 17040
acttttaaag tgatgatggt tacaaaggca aaaggggtaa aacccctcgc ctacgtaagc 17100
gttattacgc ccgtctgtac ttatatcagt acactgacga gtccctaaag gacgaaacgg 17160
gccc 17164

<210> SEQ ID NO 2
<211> LENGTH: 9696
<212> TYPE: DNA
<213> ORGANISM: Artificial
<220> FEATURE:
<223> OTHER INFORMATION: sequence of synthetic psTRV2001 vector

<400> SEQUENCE: 2
gggaattcta agaggagtcc accatggtag atctgactag tgttaacgct agccaccacc 60
accaccacca cgtgtgaatt acaggtgacc agctcgaatt tccccgatcg ttcaaacatt 120
tggcaataaa gtttcttaag attgaatcct gttgccggtc ttgcgatgat tatcatataa 180
tttctgttga attacgttaa gcatgtaata attaacatgt aatgcatgac gttatttatg 240
agatgggttt ttatgattag agtcccgcaa ttatacattt aatacgcgat agaaaacaaa 300
atatagcgcg caaactagga taaattatcg cgcgcggtgt catctatgtt actagatcgg 360
gaattaaact atcagtgttt gacaggatat attggcgggt aaacctaaga gaaaagagcg 420
tttattagaa taacggatat ttaaaagggc gtgaaaaggt ttatccgttc gtccatttgt 480
atgtgcatgc caaccacagg gttcccctcg ggatcaaagt actttgatcc aacccctccg 540
ctgctatagt gcagtcggct tctgacgttc agtgcagccg tcttctgaaa acgacatgtc 600
gcacaagtcc taagttacgc gacaggctgc cgccctgccc ttttcctggc gttttcttgt 660
cgcgtgtttt agtcgcataa agtagaatac ttgcgactag aaccggagac attacgccat 720
gaacaagagc gccgccgctg gcctgctggg ctatgcccgc gtcagcaccg acgaccagga 780
cttgaccaac caacgggccg aactgcacgc ggccggctgc accaagctgt tttccgagaa 840
gatcaccggc accaggcgcg accgcccgga gctggccagg atgcttgacc acctacgccc 900
tggcgacgtt gtgacagtga ccaggctaga ccgcctggcc cgcagcaccc gcgacctact 960
ggacattgcc gagcgcatcc aggaggccgg cgcgggcctg cgtagcctgg cagagccgtg 1020
ggccgacacc accacgccgg ccggccgcat ggtgttgacc gtgttcgccg gcattgccga 1080
gttcgagcgt tccctaatca tcgaccgcac ccggagcggg cgcgaggccg ccaaggcccg 1140
aggcgtgaag tttggccccc gccctaccct caccccggca cagatcgcgc acgcccgcga 1200
gctgatcgac caggaaggcc gcaccgtgaa agaggcggct gcactgcttg gcgtgcatcg 1260
ctcgaccctg taccgcgcac ttgagcgcag cgaggaagtg acgcccaccg aggccaggcg 1320
gcgcggtgcc ttccgtgagg acgcattgac cgaggccgac gccctggcgg ccgccgagaa 1380
tgaacgccaa gaggaacaag catgaaaccg caccaggacg gccaggacga accgtttttc 1440

-continued

```
attaccgaag agatcgaggc ggagatgatc gcggccgggt acgtgttcga gccgcccgcg   1500
cacgtctcaa ccgtgcggct gcatgaaatc ctggccggtt tgtctgatgc caagctggcg   1560
gcctggccgg ccagcttggc cgctgaagaa accgagcgcc gccgtctaaa aaggtgatgt   1620
gtatttgagt aaaacagctt gcgtcatgcg gtcgctgcgt atatgatgcg atgagtaaat   1680
aaacaaatac gcaaggggaa cgcatgaagg ttatcgctgt acttaaccag aaaggcgggt   1740
caggcaagac gaccatcgca acccatctag cccgcgccct gcaactcgcc ggggccgatg   1800
ttctgttagt cgattccgat ccccagggca gtgcccgcga ttgggcggcc gtgcgggaag   1860
atcaaccgct aaccgttgtc ggcatcgacc gcccgacgat tgaccgcgac gtgaaggcca   1920
tcggccggcg cgacttcgta gtgatcgacg gagcgcccca ggcggcggac ttggctgtgt   1980
ccgcgatcaa ggcagccgac ttcgtgctga ttccggtgca gccaagccct tacgacatat   2040
gggccaccgc cgacctggtg gagctggtta agcagcgcat tgaggtcacg gatggaaggc   2100
tacaagcggc ctttgtcgtg tcgcgggcga tcaaaggcac gcgcatcggc ggtgaggttg   2160
ccgaggcgct ggccgggtac gagctgccca ttcttgagtc ccgtatcacg cagcgcgtga   2220
gctacccagg cactgccgcc gccggcacaa ccgttcttga atcagaaccc gagggcgacg   2280
ctgcccgcga ggtccaggcg ctggccgctg aaattaaatc aaaactcatt tgagttaatg   2340
aggtaaagag aaaatgagca aaagcacaaa cacgctaagt gccggccgtc cgagcgcacg   2400
cagcagcaag gctgcaacgt tggccagcct ggcagacacg ccagccatga agcgggtcaa   2460
ctttcagttg ccggcggagg atcacaccaa gctgaagatg tacgcggtac gccaaggcaa   2520
gaccattacc gagctgctat ctgaatacat cgcgcagcta ccagagtaaa tgagcaaatg   2580
aataaatgag tagatgaatt ttagcggcta aaggaggcgg catggaaaat caagaacaac   2640
caggcaccga cgccgtggaa tgccccatgt gtggaggaac gggcggttgg ccaggcgtaa   2700
gcggctgggt tgtctgccgg ccctgcaatg gcactggaac ccccaagccc gaggaatcgg   2760
cgtgacggtc gcaaaccatc cggcccggta caaatcggcg cggcgctggg tgatgacctg   2820
gtggagaagt tgaaggccgc gcaggccgcc cagcggcaac gcatcgaggc agaagcacgc   2880
cccggtgaat cgtggcaagc ggccgctgat cgaatccgca aagaatcccg gcaaccgccg   2940
gcagccggtg cgccgtcgat taggaagccg cccaagggcg acgagcaacc agattttttc   3000
gttccgatgc tctatgacgt gggcacccgc gatagtcgca gcatcatgga cgtggccgtt   3060
ttccgtctgt cgaagcgtga ccgacgagct ggcgaggtga tccgctacga gcttccagac   3120
gggcacgtag aggtttccgc agggccggcc ggcatggcca gtgtgtggga ttacgacctg   3180
gtactgatgg cggtttccca tctaaccgaa tccatgaacc gataccggga agggaaggga   3240
gacaagcccg gccgcgtgtt ccgtccacac gttgcggacg tactcaagtt ctgccggcga   3300
gccgatggcg gaaagcagaa agacgacctg gtagaaacct gcattcggtt aaacaccacg   3360
cacgttgcca tgcagcgtac gaagaaggcc aagaacggcc gcctggtgac ggtatccgag   3420
ggtgaagcct tgattagccg ctacaagatc gtaaagagcg aaaccgggcg gccggagtac   3480
atcgagatcg agctagctga ttggatgtac cgcgagatca cagaaggcaa gaacccggac   3540
gtgctgacgg ttcaccccga ttactttttg atcgatcccg gcatcggccg ttttctctac   3600
cgcctggcac gccgcgccgc aggcaaggca gaagccagat ggttgttcaa gacgatctac   3660
gaacgcagtg gcagcgccgg agagttcaag aagttctgtt tcaccgtgcg caagctgatc   3720
gggtcaaatg acctgccgga gtacgatttg aaggaggagg cggggcaggc tggcccgatc   3780
ctagtcatgc gctaccgcaa cctgatcgag ggcgaagcat ccgccggttc ctaatgtacg   3840
```

```
gagcagatgc tagggcaaat tgccctagca ggggaaaaag gtcgaaaagg tctctttcct   3900
gtggatagca cgtacattgg gaacccaaag ccgtacattg ggaaccggaa cccgtacatt   3960
gggaacccaa agccgtacat tgggaaccgg tcacacatgt aagtgactga tataaaagag   4020
aaaaaaggcg atttttccgc ctaaaactct ttaaaactta ttaaaactct taaaacccgc   4080
ctggcctgtg cataactgtc tggccagcgc acagccgaag agctgcaaaa agcgcctacc   4140
cttcggtcgc tgcgctccct acgccccgcc gcttcgcgtc ggcctatcgc ggccgctggc   4200
cgctcaaaaa tggctggcct acggccaggc aatctaccag ggcgcggaca agccgcgccg   4260
tcgccactcg accgccggcg cccacatcaa ggcaccctgc ctcgcgcgtt tcggtgatga   4320
cggtgaaaac ctctgacaca tgcagctccc ggagacggtc acagcttgtc tgtaagcgga   4380
tgccgggagc agacaagccc gtcagggcgc gtcagcgggt gttggcgggt gtcggggcgc   4440
agccatgacc cagtcacgta gcgatagcgg agtgtatact ggcttaacta tgcggcatca   4500
gagcagattg tactgagagt gcaccatatg cggtgtgaaa taccgcacag atgcgtaagg   4560
agaaaatacc gcatcaggcg ctcttccgct tcctcgctca ctgactcgct gcgctcggtc   4620
gttcggctgc ggcgagcggt atcagctcac tcaaaggcgg taatacggtt atccacagaa   4680
tcaggggata acgcaggaaa gaacatgtga gcaaaaggcc agcaaaaggc caggaaccgt   4740
aaaaaggccg cgttgctggc gtttttccat aggctccgcc cccctgacga gcatcacaaa   4800
aatcgacgct caagtcagag gtggcgaaac ccgacaggac tataaagata ccaggcgttt   4860
ccccctggaa gctccctcgt gcgctctcct gttccgaccc tgccgcttac cggatacctg   4920
tccgcctttc tcccttcggg aagcgtggcg ctttctcata gctcacgctg taggtatctc   4980
agttcggtgt aggtcgttcg ctccaagctg ggctgtgtgc acgaaccccc cgttcagccc   5040
gaccgctgcg ccttatccgg taactatcgt cttgagtcca acccggtaag acacgactta   5100
tcgccactgg cagcagccac tggtaacagg attagcagag cgaggtatgt aggcggtgct   5160
acagagttct tgaagtggtg gcctaactac ggctacacta gaaggacagt atttggtatc   5220
tgcgctctgc tgaagccagt taccttcgga aaaagagttg gtagctcttg atccggcaaa   5280
caaaccaccg ctggtagcgg tggttttttt gtttgcaagc agcagattac gcgcagaaaa   5340
aaaggatctc aagaagatcc tttgatcttt tctacggggt ctgacgctca gtggaacgaa   5400
aactcacgtt aagggatttt ggtcatgcat tctaggtact aaaacaattc atccagtaaa   5460
atataatatt ttattttctc ccaatcaggc ttgatcccca gtaagtcaaa aaatagctcg   5520
acatactgtt cttccccgat atcctccctg atcgaccgga cgcagaaggc aatgtcatac   5580
cacttgtccg ccctgccgct tctcccaaga tcaataaagc cacttacttt gccatctttc   5640
acaaagatgt tgctgtctcc caggtcgccg tgggaaaaga caagttcctc ttcgggcttt   5700
tccgtcttta aaaaatcata cagctcgcgc ggatctttaa atggagtgtc ttcttcccag   5760
ttttcgcaat ccacatcggc cagatcgtta ttcagtaagt aatccaattc ggctaagcgg   5820
ctgtctaagc tattcgtata gggacaatcc gatatgtcga tggagtgaaa gagcctgatg   5880
cactccgcat acagctcgat aatcttttca gggctttgtt catcttcata ctcttccgag   5940
caaaggacgc catcggcctc actcatgagc agattgctcc agccatcatg ccgttcaaag   6000
tgcaggacct ttggaacagg cagctttcct tccagccata gcatcatgtc cttttcccgt   6060
tccacatcat aggtggtccc tttataccgg ctgtccgtca tttttaaata taggttttca   6120
ttttctccca ccagcttata taccttagca ggagacattc cttccgtatc ttttacgcag   6180
```

-continued

```
cggtattttt cgatcagttt tttcaattcc ggtgatattc tcattttagc catttattat   6240
ttccttcctc ttttctacag tatttaaaga taccccaaga agctaattat aacaagacga   6300
actccaattc actgttcctt gcattctaaa accttaaata ccagaaaaca gctttttcaa   6360
agttgttttc aaagttggcg tataacatag tatcgacgga gccgattttg aaaccgcggt   6420
gatcacaggc agcaacgctc tgtcatcgtt acaatcaaca tgctaccctc cgcgagatca   6480
tccgtgtttc aaacccggca gcttagttgc cgttcttccg aatagcatcg gtaacatgag   6540
caaagtctgc cgccttacaa cggctctccc gctgacgccg tcccggactg atgggctgcc   6600
tgtatcgagt ggtgattttg tgccgagctg ccggtcgggg agctgttggc tggctggtgg   6660
caggatatat tgtggtgtaa acaaattgac gcttagacaa cttaataaca cattgcggac   6720
gtttttaatg tactgaatta acgccgaatt aattcctagg ccaccatgtt gggcccggcg   6780
cgccaagctt ggtcaacatg gtggagcacg acactctcgt ctactccaag aatatcaaag   6840
atacagtctc agaagaccag agggctattg agacttttca acaaagggta atatcgggaa   6900
acctcctcgg attccattgc ccagctatct gtcacttcat cgaaaggaca gtagaaaagg   6960
aagatggctt ctacaaatgc catcattgcg ataaaggaaa ggctatcgtt caagatgcct   7020
ctaccgacag tggtcccaaa gatggacccc cacccacgag gaacatcgtg gaaaaagaag   7080
acgttccaac cacgtcttca aagcaagtgg attgatgtga tggtcaacat ggtggagcac   7140
gacactctcg tctactccaa gaatatcaaa gatacagtct cagaagacca gagggctatt   7200
gagacttttc aacaaagggt aatatcggga aacctcctcg gattccattg cccagctatc   7260
tgtcacttca tcgaaaggac agtagaaaag gaagatggct tctacaaatg ccatcattgc   7320
gataaaggaa aggctatcgt tcaagatgcc tctaccgaca gtggtcccaa agatggaccc   7380
ccacccacga ggaacatcgt ggaaaaagaa gacgttccaa ccacgtcttc aaagcaagtg   7440
gattgatgtg atatctccac tgacgtaagg gatgacgcac aatcccacta tccttcgcaa   7500
gacccttcct ctatataagg aagttcattt catttggaga ggataaaaca ttgcacctat   7560
ggtgttgccc tggctggggt atgtcagtga tcgcagtaga atgtactaat tgacaagttg   7620
gagaatacgg tagaacgtcc ttatccaaca cagcctttat ccctctccct gacgaggttt   7680
ttgtcagtgt aatatttctt tttgaactat ccagcttagt accgtacggg aaagtgactg   7740
gtgtgcttat ctttgaaatg ttactttggg tttcggttct ttaggttagt aagaaagcac   7800
ttgtcttctc atacaaagga aaacctgaga cgtatcgctt acgaaagtag caatgaaaga   7860
aaggtggtgg ttttaatcgc taccgcaaaa acgatggggt cgttttaatt aacttctcct   7920
acgcaagcgt ctaaacggac gttggggttt tgctagtttc tttagagaaa actagctaag   7980
tctttaatgt tatcattaga gatggcataa atataatact tgtgtctgct gataagatca   8040
ttttaatttg gacgattaga cttgttgaac tacaggttac tgaatcactt gcgctaatca   8100
acatgggaga tatgtacgat gaatcatttg acaagtcggg cggtcctgct gacttgatgg   8160
acgattcttg ggtggaatca gtttcgtgga aagatctgtt gaagaagtta cacagcataa   8220
aatttgcact acagtctggt agagatgaga tcactgggtt actagcggca ctgaatagac   8280
agtgtcctta ttcaccatat gagcagtttc cagataagaa ggtgtatttc cttttagact   8340
cacgggctaa cagtgctctt ggtgtgattc agaacgcttc agcgttcaag agacgagctg   8400
atgagaagaa tgcagtggcg ggtgttacaa atattcctgc gaatccaaac acaacggtta   8460
cgacgaacca agggagtact actactacca aggcgaacac tggctcgact ttggaagaag   8520
acttgtacac ttattacaaa ttcgatgatg cctctacagc tttccacaaa tctctaactt   8580
```

```
cgttagagaa catggagttg aagagttatt accgaaggaa ctttgagaaa gtattcggga   8640

ttaagtttgg tggagcagct gctagttcat ctgcaccgcc tccagcgagt ggaggtccga   8700

tacgtcctaa tccctaggga tttaaggacg tgaactctgt tgagatctct gtgaaattca   8760

gagggtgggt gataccatat tcactgatgc cattagcgac atctaaatag ggctaattgt   8820

gactaatttg agggaatttc ctttaccatt gacgtcagtg tcgttggtag catttgagtt   8880

tcgcaatgca cgaattactt aggaagtggc ttgacgacac taatgtgtta ttgttagata   8940

atggtttggt ggtcaaggta cgtagtagag tcccacatat tcgcacgtat gaagtaattg   9000

gaaagttgtc agtttttgat aattcactgg gagatgatac gctgtttgag ggaaaagtag   9060

agaacgtatt tgtttttatg ttcaggcggt tcttgtgtgt caacaaagat ggacattgtt   9120

actcaaggaa gcacgatgag ctttattatt acggacgagt ggacttagat tctgtgagta   9180

aggttaccga attctctaga aggcctccat ggggatccgg taccgagctc acgcgtctcg   9240

aggcccgggc atgtcccgaa gacattaaac tacggttctt taagtagatc cgtgtctgaa   9300

gttttaggtt caatttaaac ctacgagatt gacattctcg actgatcttg attgatcggt   9360

aagtcttttg taatttaatt ttctttttga ttttatttta aattgttatc tgtttctgtg   9420

tatagactgt ttgagatcgg cgtttggccg actcattgtc ttaccatagg ggaacggact   9480

ttgtttgtgt tgttatttta tttgtatttt attaaaattc tcaacgatct gaaaaagcct   9540

cgcggctaag agattgttgg ggggtgagta agtactttta aagtgatgat ggttacaaag   9600

gcaaaagggg taaaacccct cgcctacgta agcgttatta cgcccgtctg tacttatatc   9660

agtacactga cgagtcccta aaggacgaaa cgggtt                            9696
```

```
<210> SEQ ID NO 3
<211> LENGTH: 37
<212> TYPE: DNA
<213> ORGANISM: Helicoverpa armigera

<400> SEQUENCE: 3

aatatctaga cctccgcgaa gatgaagaac atgttcc                             37
```

```
<210> SEQ ID NO 4
<211> LENGTH: 25
<212> TYPE: DNA
<213> ORGANISM: Helicoverpa armigera

<400> SEQUENCE: 4

ctccggatcc gggaagaact ccggg                                          25
```

```
<210> SEQ ID NO 5
<211> LENGTH: 859
<212> TYPE: DNA
<213> ORGANISM: Helicoverpa armigera

<400> SEQUENCE: 5

cctccgcgaa gatgaagaac atgttccatt tgatcgaaaa gtgttctcac gtgttcgaag     60

attttctcga taaggaagcc aaaagcaacg aggtcgaaat gagggctctt gtagcgagat    120

acactatgga ctgcatagga acctgtgcat ttggcgttga aacaaaaacc atgaatgtga    180

cggaaaataa tccgtttaca gcagtaggta acagcatttt catgttaagc cgggtccaag    240

gatttaaatt tgttttgaga ggtatctacc cttcactttt ctacttgttg ggattcagaa    300

ctcttccacc agaagttaat gcattcttct ccaatttaat gactggagtt tttaagggac    360
```

gcaactatac gcccacatct cggaatgact ttgtcgattt cgtattgaag tggaaacaaa 420
ataaaactat gacaggggac agtctgacta acatgaaata tgattcacag aaaaaagtga 480
ctttagaagt cgacgatgat ctcttagtgg cacagtgctt tatatttttt gctgctggat 540
atgaaacttc ggccaccact ttgagtttta ctttgtatga gttggcgaaa cacccagaag 600
ctcagaagag agctatagcc gaggtggacg attatctgcg gcgacacaac aatgagctga 660
agtacgagtg cctttcggag atgccatttg tagaagcgtg ctttgatgag actcttcgta 720
aatatccagt tttaagtttg ttaactcgcg aagtggtaga ggattacact ttcccttcgg 780
gattgaaggt agagaaaggt ctccgtatat tcctgcctct gtatcacttg caccataacc 840
cggagttctt cccggatcc 859

<210> SEQ ID NO 6
<211> LENGTH: 30
<212> TYPE: DNA
<213> ORGANISM: Helicoverpa armigera

<400> SEQUENCE: 6
ggaatctaga cgacgctggg tatcgtgcaa 30

<210> SEQ ID NO 7
<211> LENGTH: 24
<212> TYPE: DNA
<213> ORGANISM: Helicoverpa armigera

<400> SEQUENCE: 7
gagaagttgt ggggatccgc caac 24

<210> SEQ ID NO 8
<211> LENGTH: 763
<212> TYPE: DNA
<213> ORGANISM: Helicoverpa armigera

<400> SEQUENCE: 8
cgacgctggg tatcgtgcaa gtgttctggg gtctggacaa gaagctggcg cagcgcaagc 60
acttcccgtc catcaactgg ctcatctcct acagcaagta catgcgagcc ctcgacgact 120
tctacgacaa gaactacgtc gagttcgtgc ctcttaggac taaggtcaag gagatcctac 180
aggaggagga ggatctgtca gaaatcgtgc agctggtcgg caaagcgtcg ctcgctgaga 240
ccgacaagat caccctcgag gtcgccaagc tgctcaagga cgacttcttg cagcagaaca 300
gctactcggc atacgatcgc ttctgtccgt tctacaagac ggtgggcatg ctgaagaaca 360
tcatcgcgtt ctacgacatg tcgcgccacg ccgtggagtc caccgcgcag tccgacaaca 420
aggtcacgtg gaacgtcatc cgcgacgcca tgggcaacgt gctctaccag ctcttcttca 480
tgaagttcaa ggaccccgtg aaagatggcg aagctaagat caaggcagat ttcgaccagc 540
tgctcgagga catggcggcc gccttccgca acctcgaaga ctagacccgc acactgtaac 600
ataatgtcgt acaatgtact acgcagacgc gtattgttaa tacactaata gatgtcttgt 660
ctacgtagtg tgaataggtt taattatatt attactcgta tttcaatgca gaattcgtga 720
ttccaattgt tgaaatcggt cgtcggcggc cgttggcgga tcc 763

<210> SEQ ID NO 9
<211> LENGTH: 33
<212> TYPE: DNA
<213> ORGANISM: Helicoverpa armigera

<400> SEQUENCE: 9
ataattctag acaagcctct tacccggtcg cgc 33

<210> SEQ ID NO 10
<211> LENGTH: 32
<212> TYPE: DNA
<213> ORGANISM: Helicoverpa armigera

<400> SEQUENCE: 10
aatgcggatc cagtgcctcc accgaaggag tg 32

<210> SEQ ID NO 11
<211> LENGTH: 506
<212> TYPE: DNA
<213> ORGANISM: Helicoverpa armigera
<220> FEATURE:
<221> NAME/KEY: misc_feature
<222> LOCATION: (128)..(128)
<223> OTHER INFORMATION: n is a, c, g, or t

<400> SEQUENCE: 11
caagcctctt acccggtcgc gctgaacgac gactgatatt ctacattaag ttcaacaaaa 60
ctcaattcaa aatgcgtgag tgcatctccg tacacgttgg acaagccgga gtccagatcg 120
gtaatgcntg ctgggaatta tactgccttg agcatggaat ccagcccgat ggccagatgc 180
ccacagacaa gaccgtgggt ggtggcgatg actccttcaa caccttcttc agcgagaccg 240
gtgccggcaa acacgtgccc agggctgtgt ttgttgactt ggaacccact gtagtcgatg 300
aggtccgcac tggcacatac agacagttgt ttcatccaga acaacttatc actggtaagg 360
aagatgcggc caacaactac gcccgtggtc actacaccat cggcaaggag atcgtagacc 420
tagtcctcga ccgcatccgc aagctggccg accagtgcac tggcctgcag ggcttcctca 480
tcttccactc cttcggtgga ggcact 506

<210> SEQ ID NO 12
<211> LENGTH: 33
<212> TYPE: DNA
<213> ORGANISM: Helicoverpa armigera

<400> SEQUENCE: 12
ctatggtacc cagttcttct ggtactttcc ygc 33

<210> SEQ ID NO 13
<211> LENGTH: 44
<212> TYPE: DNA
<213> ORGANISM: Helicoverpa armigera

<400> SEQUENCE: 13
ccatctcgag ccatgtgtcc cgcgttcctg accatgayct ccac 44

<210> SEQ ID NO 14
<211> LENGTH: 1075
<212> TYPE: DNA
<213> ORGANISM: Helicoverpa armigera

<400> SEQUENCE: 14
cagttcttct ggtactttcc tgcgatgata ccaaacaata aggacgcgcc agtcgtcgtg 60
tggctgcagg gcgggcctgg tgccacctct ttgtacggtc tgttcactga aaatggtccg 120
ataagagtgc gcaacgacaa atttgagaga aggaagtata actgggcctt gagccaccac 180
atgatctaca tagacaaccc cgtcggtaca gggttcagct tcacaaacga cagccgcggc 240

```
tactgcacca acgagacgca ggttggagag cagctgtact ccaccttgat acagttcttc    300

cagctcttcc ctgaactgca acagaacaag ttctttgtaa ccggagagtc ttatggaggg    360

aagtatgtgc ctgctctggc ttacaccata cacaagaaga accccactgc aaaattgaaa    420

atcaacatga aaggaattgc cattggcaat ggtctgagtg accccgaaca ccagttggtg    480

tacggcaaat atttgtatca aataggtctc attgattgga atggagctca acaatttgag    540

ctttatgaaa ataagactaa aaactatatc aaacaaggca aatgggatga ggccttcaat    600

acatttgatt cacttttaaa tggtgatatg attgctggca aaagtttgtt caccaacctg    660

acaggcttca acttctattt caacttcttg cataccaagg attacactaa atatgaggac    720

tttggcccaa tgctgcagaa gactgcagtc cgtagaatga ttcatgtagg aaacctgact    780

ttcaataatg ggtcgatagt tgaaaagcat ctgaagcaag atgtaatgaa gtctgtggct    840

ccatggatat ctgagctcct agaccattac tacgtggtca tctacaatgg tcaactggac    900

atcattgtag cctacccctt aactgtaaac tacctcagaa acctcaactt tactggtgct    960

gcagaataca agtctgcaaa gcggtatgtt tggaaggtgg acggagaagt ggctggctat   1020

gtgaaacagg ctgggaagct ggtggagatc atggtcagga acgcgggaca catgg        1075


<210> SEQ ID NO 15
<211> LENGTH: 35
<212> TYPE: DNA
<213> ORGANISM: Helicoverpa armigera

<400> SEQUENCE: 15

aaaatctaga cctgctccgt acaccaatgc tactg                                35


<210> SEQ ID NO 16
<211> LENGTH: 35
<212> TYPE: DNA
<213> ORGANISM: Helicoverpa armigera

<400> SEQUENCE: 16

gtaaggatcc gtaatcctct tcagaattgc agacg                                35


<210> SEQ ID NO 17
<211> LENGTH: 693
<212> TYPE: DNA
<213> ORGANISM: Helicoverpa armigera

<400> SEQUENCE: 17

cctgctccgt acaccaatgc tactggattc tgggcttatt atgagatctg taccgaagtc     60

gacaaagaag gctcgggctg gaccaagaaa tgggacgacg ccggcaaatg tccctacgcc    120

tacaagggca cccagtgggt cggctatgaa gaccctcgca gtgtcgagat caagatgaac    180

tggatcaagg agaagggcta cctgggtgcc atgacctggg ccattgacat ggatgacttc    240

aaggggctct gtggagacga aaatcctctg attaagctcc tgcataagca tatgagcact    300

tatactgtcc caccacctcg ttctggaaat actactccta cgcctgaatg ggcgcggccg    360

ccgtcaacaa cgtccgaccc ggctgagggg gagatcgtca ctactgtcaa gcccacgact    420

gcgaagccag ctacgacgaa accaactacg gccaagccaa cgacggccaa gcctacgaca    480

gccaagccaa caacggccaa gcctacgacc accaaggctc ctcaagtcgt aacaatccct    540

gacgatgaga atgacatcgc tgtgagacct gaacctccga aaaaacctgt aactccagaa    600

acccctgtgg tacctgaagt tcctgaatct gctgaaacac caactgaaaa tgaaatagat    660

aaccacgacg tctgcaattc tgaagaggat tac                                 693
```

<210> SEQ ID NO 18
<211> LENGTH: 39
<212> TYPE: DNA
<213> ORGANISM: Helicoverpa armigera

<400> SEQUENCE: 18
caatggtacc gtgccgaagg tcctcagcga catattcga 39

<210> SEQ ID NO 19
<211> LENGTH: 34
<212> TYPE: DNA
<213> ORGANISM: Helicoverpa armigera

<400> SEQUENCE: 19
gtctctcgag cgccagtttg gcggcggcgc gttt 34

<210> SEQ ID NO 20
<211> LENGTH: 330
<212> TYPE: DNA
<213> ORGANISM: Helicoverpa armigera

<400> SEQUENCE: 20
gtgccgaagg tcctcagcga catattcgaa gcgctagtgg gcgcgatata tttggactgc 60
ggcggcgacc tacaagttgt atggtcggta gtttaccgta taatgtgtaa ggaaatacat 120
gacttctcgt gccgtatacc gcaacagccc gttaagatat tgtacgagaa aatacacgcg 180
tgccccactt tcaggaaacc agaagtcatc gatcctgaca ttccaaagat acggataggg 240
gttacaatca cgaagaatga ctggcaacac acagtctatg gcattggtcg aaacaaggct 300
caagcaaaac gcgccgccgc caaactggcg 330

<210> SEQ ID NO 21
<211> LENGTH: 36
<212> TYPE: DNA
<213> ORGANISM: Nicotiana benthamiana

<400> SEQUENCE: 21
acatggtacc aagaaaacaa ttgctgatat agttga 36

<210> SEQ ID NO 22
<211> LENGTH: 33
<212> TYPE: DNA
<213> ORGANISM: Nicotiana benthamiana

<400> SEQUENCE: 22
atccctcgag actgatctca gatcagtcaa ctg 33

<210> SEQ ID NO 23
<211> LENGTH: 395
<212> TYPE: DNA
<213> ORGANISM: Nicotiana benthamiana

<400> SEQUENCE: 23
aagaaaacaa ttgctgatat agttgaagcc cttgttggcg cttttgtagt tgacagtggc 60
ttcaaagcgg caattgcatt tcttaaatgg attggtatct atacagattt cgaagaatca 120
caagtaaaga gtatttgtgc tgcaagcaaa atctttattc cacttgctga tgaaatagat 180
attccggcca ttgaaaattt attaggttat tcattcgtcc ataagggttt gctcattcag 240
gccttcatcc atccatctta taacaaccac ggaggaggtt gctatcagag actggagttt 300

-continued cttggagatg ctgccctcga ttatttgatc acatcctatc tatactctgt gtacccaaaa 360
ctgaagcctg gccagttgac tgatctgaga tcagt 395

<210> SEQ ID NO 24
<211> LENGTH: 30
<212> TYPE: DNA
<213> ORGANISM: Helicoverpa armigera

<400> SEQUENCE: 24
aatatctaga ggcacgaagg gcgaatcaca 30

<210> SEQ ID NO 25
<211> LENGTH: 32
<212> TYPE: DNA
<213> ORGANISM: Helicoverpa armigera

<400> SEQUENCE: 25
gtgtggatcc tttgcttcct ggtatcccgg gg 32

<210> SEQ ID NO 26
<211> LENGTH: 641
<212> TYPE: DNA
<213> ORGANISM: Helicoverpa armigera

<400> SEQUENCE: 26
ggcacgaagg gcgaatcaca gtgtgagata gaacaattca gaatgtcctt agacttgtat 60
tacgcccctg ggtcggcacc gtgccgagtg gtcctgctcg tagcagcagc cctcgacgtc 120
cattttaatc cccacatctt aaacttaaga aatggcgaac acctcacacc agaatttttg 180
aagctgaatc cccaacacac agtgcccaca ctagtcgacg gcgacttctc tctatgggag 240
tcgagagcca tcggcaaata cttggtgaac aaatatggcg gcgagaacaa cgacttgtat 300
cctagtgatc ctaaagccag ggcgatcgtc gaccagagac tagacttcga cttgggaacg 360
ctttacccaa gatttggaaa ctacatctat cctcaaatct tcggtggagc gaaagcagat 420
gaggctctgc tcaagaagct ggaggaagct ctgcacttcc tcaacacatt cctcgaaggt 480
cagaagtacg ctgcgggtga caaactgacc ttggcagacc tcagtctcgt ggcgactgtg 540
tccactatag acgccgtcga catcagcctg aaggaatatc ccaatgttga aaagtggttc 600
gagctggtga aagcgactgc cccgggatac caggaagcaa a 641

<210> SEQ ID NO 27
<211> LENGTH: 35
<212> TYPE: DNA
<213> ORGANISM: Helicoverpa armigera

<400> SEQUENCE: 27
ctagtctaga agtgcctcca ccgaaggagt ggaag 35

<210> SEQ ID NO 28
<211> LENGTH: 35
<212> TYPE: DNA
<213> ORGANISM: Helicoverpa armigera

<400> SEQUENCE: 28
tcgcggatcc caagcctctt acccggtcgc gctga 35

<210> SEQ ID NO 29
<211> LENGTH: 506
<212> TYPE: DNA
<213> ORGANISM: Helicoverpa armigera

<400> SEQUENCE: 29
agtgcctcca ccgaaggagt ggaagatgag gaagccctgc aggccagtgc actggtcggc 60
cagcttgcgg atgcggtcga ggactaggtc tacgatctcc ttgccgatgg tgtagtgacc 120
acgggcgtag ttgttggccg catcttcctt accagtgata agttgttctg gatgaaacaa 180
ctgtctgtat gtgccagtgc ggacctcatc gactacagtg ggttccaagt caacaaacac 240
agccctgggc acgtgtttgc cggcaccggt ctcgctgaag aaggtgttga aggagtcatc 300
gccaccaccc acggtcttgt ctgtgggcat ctggccatcg ggctggattc catgctcaag 360
gcagtataat tcccagcagg cattaccgat ctggactccg gcttgtccaa cgtgtacgga 420
gatgcactca cgcattttga attgagtttt gttgaactta atgtagaata tcagtcgtcg 480
ttcagcgcga ccgggtaaga ggcttg 506

<210> SEQ ID NO 30
<211> LENGTH: 35
<212> TYPE: DNA
<213> ORGANISM: Helicoverpa armigera

<400> SEQUENCE: 30
acgcggatcc caagcctctt acccggtcgc gctga 35

<210> SEQ ID NO 31
<211> LENGTH: 36
<212> TYPE: DNA
<213> ORGANISM: Helicoverpa armigera

<400> SEQUENCE: 31
tccggaattc agtgcctcca ccgaaggagt ggaaga 36

<210> SEQ ID NO 32
<211> LENGTH: 35
<212> TYPE: DNA
<213> ORGANISM: Helicoverpa armigera

<400> SEQUENCE: 32
acccaagctt agtgcctcca ccgaaggagt ggaag 35

<210> SEQ ID NO 33
<211> LENGTH: 36
<212> TYPE: DNA
<213> ORGANISM: Helicoverpa armigera

<400> SEQUENCE: 33
tccgctcgag caagcctctt acccggtcgc gctgaa 36

<210> SEQ ID NO 34
<211> LENGTH: 896
<212> TYPE: DNA
<213> ORGANISM: Helicoverpa armigera

<400> SEQUENCE: 34
ctgtaacggc cgcgacgctg ggtatcgtgc aagtgttctg gggtctggac aagaagctgg 60
cgcagcgcaa gcacttcccg tccatcaact ggctcatctc ctacagcaag tacatgcgag 120
ccctcgacga cttctacgac aagaactacg tcgagttcgt gcctcttagg actaaggtca 180
aggagatcct acaggaggag gaggatctgt cagaaatcgt gcagctggtc ggcaaagcgt 240
cgctcgctga gaccgacaag atcaccctcg aggtcgccaa gctgctcaag gacgacttct 300

-continued

```
tgcagcagaa cagctactcg gcatacgatc gcttctgtcc gttctacaag acggtgggca    360

tgctgaagaa catcatcgcg ttctacgaca tgtcgcgcca cgccgtggag tccaccgcgc    420

agtccgacaa caaggtcacg tggaacgtca tccgcgacgc catgggcaac gtgctctacc    480

agctcttctt catgaagttc aaggaccccg tgaaagatgg cgaagctaag atcaaggcag    540

atttcgacca gctgctcgag gacatggcgg ccgccttccg caacctcgaa gactagaccc    600

gcacactgta acataatgtc gtacaatgta ctacgcagac gcgtattgtt aatacactaa    660

tagatgtctt gtctacgtag tgtgaatagg tttaattata ttattactcg tatttcaatg    720

cagaattcgt gattccaatt gttgaaatcg gtcgtcggcg gccgttggcg gatccccaca    780

actctccatt tgtaaatata cgaacaaatg ccgccggccc gccgcgacta cagttaatta    840

gttgttattt atataaaata tatactattt atacactaaa aaaaaaaaaa aaaaaa        896
```

<210> SEQ ID NO 35
<211> LENGTH: 2870
<212> TYPE: DNA
<213> ORGANISM: Helicoverpa armigera

<400> SEQUENCE: 35

```
gacaatcgca cgccggccgc ccgccgcgac accgcgactg ttcaaaatga gagtgatact     60

agcgacgttg gccgtcctgg cggtcgcaac gactgcaatt gaagcggaca gcaaagcgcg    120

catagtatgc tacttcagca actgggcggt gtaccggccc ggcgtgggtc gctacggcat    180

cgaggacatc cccgtggacc tctgcacgca catcatctac tccttcatcg gcgtcactga    240

gaagagcaat gaagttctca tcattgatcc tgagctggac gtagacaaga acggtttcag    300

gaacttcaca gctcttcgga agtcgcaccc taacgtgaag ttcacagtgg ctgtgggtgg    360

ctgggccgag ggtggctcta aatactcgca catggttgcg cagaaacaaa ccagaatggc    420

tttcgttagg agcgttgtag acttcctgaa gaaatacgac tttgatggtt tggacttgga    480

ttgggagtac cctggtgctg ctgaccgtgg tggctccttc tcagacaagg atcggttcct    540

cttcctcgtc caggagttga ggagagcctt catcagggag aagaggggat gggaactgac    600

tgctgctgtg cctctcgcta acttcagact gatggaagga taccacgtac cggatctttg    660

ccaagagctg gatgctatcc acgtgatgtc gtacgatttg cgcggcaact gggccggctt    720

tgcagatgtg cactcacctt tatataagcg tcctcatgat caatgggctt atgagaaatt    780

gaatgtgaat gatggcttag cgctctggga agagaagggc tgtcccagca acaagctcgt    840

cgtcggcatt ccgttctacg gtcgctcatt cactctgtca gctggtaaca acaactacgg    900

acttggtact tacatcaaca aggaggctgg aggtggcgat cctgctccgt acaccaatgc    960

tactggattc tgggcttatt atgagatctg taccgaagtc gacaaagaag gctcgggctg   1020

gaccaagaaa tgggacgacg ccggcaaatg tccctacgcc tacaagggca cccagtgggt   1080

cggctatgaa gaccctcgca gtgtcgagat caagatgaac tggatcaagg agaagggcta   1140

cctgggtgcc atgacctggg ccattgacat ggatgacttc aaggggctct gtggagacga   1200

aaatcctctg attaagctcc tgcataagca tatgagcact tatactgtcc caccacctcg   1260

ttctggaaat actactccta cgcctgaatg ggcgcggccg ccgtcaacaa cgtccgaccc   1320

ggctgagggg gagatcgtca ctactgtcaa gcccacgact gcgaagccag ctacgacgaa   1380

accaactacg gccaagccaa cgacggccaa gcctacgaca gccaagccaa caacggccaa   1440

gcctacgacc accaaggctc ctcaagtcgt aacaatccct gacgatgaga atgacatcgc   1500

tgtgagacct gaacctccga aaaaacctgt aactccagaa acccctgtgg tacctgaagt   1560
```

```
tcctgaatct gctgaaacac caactgaaaa tgaaatagat aaccacgacg tctgcaattc   1620
tgaagaggat tacgtgcctg acaagaaaaa gtgcgataag tactggcgat gcgtcaacgg   1680
acaaggaatg ctgttcacat gccaaccagg aactgtgttc aacgtgaagc tgaatgtttg   1740
cgactggccc gacaatgccg accgtaagcg actgcgagcc ctaaactgcc ggctcatgaa   1800
caggacgcct tagtggtcat tgcacagata ccgtttgatt gaaatcgcat tcgccttgca   1860
agacagctga taaattatgt tgctccgttg cgggttgcat ctcagttcaa tctggcgtct   1920
cgcccgacat tggtatgcgg ggaaacaagg ctgtcaatgc aatagcaatt agcaaatgag   1980
ggttcgacta aatgagacaa cacttggaga cgtcttgaag tactggtctc aaaacttcaa   2040
cagcaaaatc tagatttatt cgctttaatt aaattcaata tagaagtgaa ccgtgcgagg   2100
tcccctcgct ttgtgtggtc tagcttgcgg cttgattttg ataaaccggt atctttcctc   2160
ttcgcaatga atcacaataa tgttcgtatt tacgatgttt taggttactg aacaatattg   2220
tcgtattttg ttatgctgca acataatacg ccaatgtttt ctcgtgtctc tatattataa   2280
ttgggtaggt ttgtgatgtt taggctgtat ctacttatgt acatagtgag tttcttacat   2340
aaatcatgat gcattttatt gggaatacga tgaacacaaa ttaatcccag ataaagcaca   2400
atttggtaag aaatcggcga atttaaaatg agattattag tgtatcactt atataatgcc   2460
ttagattgtg tacaagactg catcgaatag atttaaatat aaaataagga actaattatt   2520
aagttcatct ttgtttccat cttatataca aacaacataa aatatttgcg aaagttctag   2580
aagcatggac atttttattt gctcatttta gtttgttaag aactgttgca gtttccgccg   2640
ataactctat tcagctgtta taaagttatg gcagaaattg tgtttatttt ataaattttg   2700
tttcgactgg aagccaatta gactggtccc ggctttagga gatttaaatg aatttccccc   2760
gcacttgtcg cgggtggtcg ctcgcttaaa caaacccagt gtaatttatt tatttttaat   2820
aattttaaga caataaatta tggtaaaaat ctaaaaaaaa aaaaaaaaaa              2870
```

<210> SEQ ID NO 36
<211> LENGTH: 840
<212> TYPE: DNA
<213> ORGANISM: Helicoverpa armigera

<400> SEQUENCE: 36

```
ggcacgaagg gcgaatcaca gtgtgagata gaacaattca gaatgtcctt agacttgtat     60
tacgcccctg ggtcggcacc gtgccgagtg gtcctgctcg tagcagcagc cctcgacgtc    120
cattttaatc cccacatctt aaacttaaga aatggcgaac acctcacacc agaatttttg    180
aagctgaatc cccaacacac agtgcccaca ctagtcgacg gcgacttctc tctatgggag    240
tcgagagcca tcggcaaata cttggtgaac aaatatggcg gcgagaacaa cgacttgtat    300
cctagtgatc ctaaagccag ggcgatcgtc gaccagagac tagacttcga cttgggaacg    360
ctttacccaa gatttggaaa ctacatctat cctcaaatct tcggtggagc gaaagcagat    420
gaggctctgc tcaagaagct ggaggaagct ctgcacttcc tcaacacatt cctcgaaggt    480
cagaagtacg ctgcgggtga caaactgacc ttggcagacc tcagtctcgt ggcgactgtg    540
tccactatag acgccgtcga catcagcctg aaggaatatc ccaatgttga aaagtggttc    600
gagctggtga aagcgactgc cccgggatac caggaagcaa atgaagctgg ccttaaagca    660
ttcagagcta tggtagcgca gttaaaagct aaaactgaat tgtaagtgta gcagcataat    720
gcaatattgt atttagaggt acagaagtaa gagagcattt gctcgcagta taatagtaat    780
```

-continued

```
actcgcattt tgtaagaaat tgtcgttaag taaaaatatt tatatttgaa aaaaaaaaaa    840


<210> SEQ ID NO 37
<211> LENGTH: 689
<212> TYPE: DNA
<213> ORGANISM: Helicoverpa armigera
<220> FEATURE:
<221> NAME/KEY: CDS
<222> LOCATION: (88)..(687)

<400> SEQUENCE: 37

caagcctctt aaccggtcgc gctgaacgac gactgatatt taaattaatt tatattctac     60

attaagttca acaaaactca attcaaa atg cgt gag tgc atc tcc gta cac gtt    114
                              Met Arg Glu Cys Ile Ser Val His Val
                              1               5

gga caa gcc gga gtc cag atc ggt aac gcc tgc tgg gaa tta tac tgc      162
Gly Gln Ala Gly Val Gln Ile Gly Asn Ala Cys Trp Glu Leu Tyr Cys
10                  15                  20                  25

ctt gag cat gga atc cag ccc gat ggc cag atg ccc aca gac aag acc      210
Leu Glu His Gly Ile Gln Pro Asp Gly Gln Met Pro Thr Asp Lys Thr
                30                  35                  40

gtg ggt ggt ggc gat gac tcc ttc aac acc ttc ttc agc gag acc ggt      258
Val Gly Gly Gly Asp Asp Ser Phe Asn Thr Phe Phe Ser Glu Thr Gly
            45                  50                  55

gcc ggc aaa cac gtg ccc agg gct gtg ttt gtt gac ttg gaa ccc act      306
Ala Gly Lys His Val Pro Arg Ala Val Phe Val Asp Leu Glu Pro Thr
        60                  65                  70

gta gtc gat gag gtc cgc act ggc aca tac aga cag ttg ttt cat cca      354
Val Val Asp Glu Val Arg Thr Gly Thr Tyr Arg Gln Leu Phe His Pro
    75                  80                  85

gaa caa ctt atc act ggt aag gaa gat gcg gcc aac aac tac gcc cgt      402
Glu Gln Leu Ile Thr Gly Lys Glu Asp Ala Ala Asn Asn Tyr Ala Arg
90                  95                  100                 105

ggt cac tac acc atc ggc aag gag atc gtt gac cta gtc ctc gac cgc      450
Gly His Tyr Thr Ile Gly Lys Glu Ile Val Asp Leu Val Leu Asp Arg
                110                 115                 120

atc cgc aag ctg gcc gac cag tgc act ggc ctg cag ggc ttc ctc atc      498
Ile Arg Lys Leu Ala Asp Gln Cys Thr Gly Leu Gln Gly Phe Leu Ile
            125                 130                 135

ttc cac tcc ttc ggt gga ggc act gga tcc ggt ttc acc tcc ctc ctt      546
Phe His Ser Phe Gly Gly Gly Thr Gly Ser Gly Phe Thr Ser Leu Leu
        140                 145                 150

atg gag cga ctc tcc gtg gac tac ggc aag aag tcc aag ctg gag ttc      594
Met Glu Arg Leu Ser Val Asp Tyr Gly Lys Lys Ser Lys Leu Glu Phe
    155                 160                 165

gcc atc tac ccg gcg cct cag tgt cac cgg cgt cgt aaa gcc cta caa      642
Ala Ile Tyr Pro Ala Pro Gln Cys His Arg Arg Arg Lys Ala Leu Gln
170                 175                 180                 185

ctt cat tct acc acc cca cac cac ctg gag cac ttc gac tgt gcc tt       689
Leu His Ser Thr Thr Pro His His Leu Glu His Phe Asp Cys Ala
                190                 195                 200


<210> SEQ ID NO 38
<211> LENGTH: 200
<212> TYPE: PRT
<213> ORGANISM: Helicoverpa armigera

<400> SEQUENCE: 38

Met Arg Glu Cys Ile Ser Val His Val Gly Gln Ala Gly Val Gln Ile
1               5                   10                  15

Gly Asn Ala Cys Trp Glu Leu Tyr Cys Leu Glu His Gly Ile Gln Pro
```

-continued

```
            20                  25                  30

Asp Gly Gln Met Pro Thr Asp Lys Thr Val Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Val Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Val Asp Leu Val Leu Asp Arg Ile Arg Lys Leu Ala Asp Gln
        115                 120                 125

Cys Thr Gly Leu Gln Gly Phe Leu Ile Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ala Ile Tyr Pro Ala Pro Gln
                165                 170                 175

Cys His Arg Arg Arg Lys Ala Leu Gln Leu His Ser Thr Thr Pro His
            180                 185                 190

His Leu Glu His Phe Asp Cys Ala
        195                 200


<210> SEQ ID NO 39
<211> LENGTH: 570
<212> TYPE: DNA
<213> ORGANISM: Nicotiana benthamiana

<400> SEQUENCE: 39

acaggcatat atacgtgatc aatcatttta tcccaacaac ttctacgcag taggccgtcc      60

gtgcccagaa atctgtaaca aacaaacaga aaacagcata cacggtcaat gtggtaatgt     120

aacagatggt gcaaagactg aagttaggtg tagcaaatgt catcagtggt tgcgtaagaa     180

aacaattgct gatatagttg aagcccttgt tggcgctttt atagttgaca gtggcttcaa     240

agcggcaatt gcatttctta aatggattgg tatctataca gatttcgaag aatcacaagt     300

aaagagtatt tgtgctgcaa gcaaaatctt tattccactt gctgatgaaa tagatattcc     360

ggccattgaa aatttattag gttattcatt cgtccataag ggtttgctca ttcaggcctt     420

catccatcca tcttataaca accacggagg aggttgctat cagagactgg agtttcttgg     480

agatgctgcc ctcgattatt tgatcacatc ctatctatac tctgtgtacc caaaactgaa     540

gcctggccag ttgactgatc tgagatcagt                                      570
```